United States Patent
Okamoto et al.

(10) Patent No.: US 10,172,600 B2
(45) Date of Patent: Jan. 8, 2019

(54) INSERTION APPARATUS

(71) Applicant: OLYMPUS CORPORATION, Tokyo (JP)

(72) Inventors: Yasuhiro Okamoto, Hino (JP); Hiroki Moriyama, Akishima (JP); Hiroaki Miyoshi, Fuchu (JP); Yutaka Masaki, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 809 days.

(21) Appl. No.: 14/282,041

(22) Filed: May 20, 2014

(65) Prior Publication Data

US 2014/0309625 A1  Oct. 16, 2014

Related U.S. Application Data

(63) Continuation of application No. PCT/JP2013/050651, filed on Jan. 16, 2013.

(30) Foreign Application Priority Data

Jan. 16, 2012 (JP) ................................. 2012-006301
Jan. 23, 2012 (JP) ................................. 2012-011326
(Continued)

(51) Int. Cl.
*A61B 17/00* (2006.01)
*A61B 19/00* (2006.01)
(Continued)

(52) U.S. Cl.
CPC ...... *A61B 17/00234* (2013.01); *A61B 1/0016* (2013.01); *A61B 1/0052* (2013.01);
(Continued)

(58) Field of Classification Search
None
See application file for complete search history.

(56) References Cited

U.S. PATENT DOCUMENTS 4,688,555 A * 8/1987 Wardle ................ A61B 1/0052
600/149
4,832,473 A * 5/1989 Ueda .................... A61B 1/0053
359/367
(Continued)

FOREIGN PATENT DOCUMENTS

EP 2 006 565 A1 12/2008
EP 2 229 868 A1 9/2010
(Continued)

OTHER PUBLICATIONS

International Search Report dated Mar. 19, 2013 issued in PCT/JP2013/050651.

*Primary Examiner* — Carl H Layno
*Assistant Examiner* — Manolis Pahakis
(74) *Attorney, Agent, or Firm* — Scully, Scott, Murphy & Presser, P.C.

(57) ABSTRACT

An insertion apparatus according to an aspect of the present invention includes: an insertion portion to be inserted into a subject; a bending operation apparatus to be moved by an operator to input an operation instruction; a bending drive section that generates a drive force based on the movement of the bending operation apparatus; a pulling member to be pulled by the drive force from the bending drive section; a bending portion provided in the insertion portion, the bending portion being connected to the pulling member and being bent upon the pulling member being pulled; and a haptic section that connects the pulling member and the bending operation apparatus via an elastic portion.

5 Claims, 36 Drawing Sheets

(30) Foreign Application Priority Data

Feb. 6, 2012 (JP) ................................ 2012-023182
Feb. 6, 2012 (JP) ................................ 2012-023183

(51) Int. Cl.
    *A61B 34/30*     (2016.01)
    *A61B 34/00*     (2016.01)
    *A61B 1/005*     (2006.01)
    *A61B 1/00*     (2006.01)

(52) U.S. Cl.
    CPC ............ *A61B 1/0057* (2013.01); *A61B 34/30* (2016.02); *A61B 34/71* (2016.02)

(56) References Cited

U.S. PATENT DOCUMENTS

| | | | |
|---|---|---|---|
| 5,179,934 A * | 1/1993 | Nagayoshi | A61B 1/00183 600/152 |
| 5,209,747 A * | 5/1993 | Knoepfler | A61B 17/29 604/22 |
| 5,299,559 A * | 4/1994 | Bruce | A61B 1/0052 600/141 |
| 5,405,344 A * | 4/1995 | Williamson | A61B 17/1285 606/1 |
| 5,482,029 A * | 1/1996 | Sekiguchi | A61B 1/00039 600/109 |
| 5,650,704 A * | 7/1997 | Pratt | B25J 9/10 318/560 |
| 5,785,663 A * | 7/1998 | Sarvazyan | A61B 1/0052 600/561 |
| 5,944,690 A * | 8/1999 | Falwell | A61M 25/0136 600/146 |
| 7,524,301 B2 * | 4/2009 | Dubois | A61M 25/0147 604/523 |
| 7,670,334 B2 * | 3/2010 | Hueil | A61B 17/07207 227/175.1 |
| 8,137,308 B2 * | 3/2012 | Schultz | A61M 25/0136 600/434 |
| 8,308,634 B2 * | 11/2012 | Torii | A61B 1/0052 600/146 |
| 8,747,351 B2 * | 6/2014 | Schultz | A61B 5/04 600/381 |
| 8,808,169 B2 * | 8/2014 | Macnamara | A61B 1/0052 600/144 |
| 8,961,402 B2 * | 2/2015 | Okamoto | A61B 1/0052 600/139 |
| 2004/0010245 A1 * | 1/2004 | Cerier | A61B 17/00234 606/1 |
| 2005/0119527 A1 * | 6/2005 | Banik | A61B 1/00059 600/117 |
| 2005/0277874 A1 * | 12/2005 | Selkee | A61M 25/0136 604/95.04 |
| 2006/0116692 A1 * | 6/2006 | Ward | A61B 17/221 606/113 |
| 2007/0021737 A1 * | 1/2007 | Lee | A61B 17/062 606/1 |
| 2008/0087871 A1 * | 4/2008 | Schena | B25J 9/1045 254/226 |
| 2008/0103520 A1 * | 5/2008 | Selkee | A61M 25/0136 606/195 |
| 2008/0188868 A1 * | 8/2008 | Weitzner | A61B 1/0014 606/130 |
| 2008/0287862 A1 * | 11/2008 | Weitzner | A61M 25/0136 604/28 |
| 2008/0308607 A1 * | 12/2008 | Timm | A61B 17/07207 227/176.1 |
| 2008/0319265 A1 | 12/2008 | Masaki | |
| 2009/0192357 A1 * | 7/2009 | Torii | A61B 1/0052 600/149 |
| 2010/0082041 A1 * | 4/2010 | Prisco | B25J 9/1045 606/130 |
| 2010/0331820 A1 * | 12/2010 | Prisco | A61B 1/0052 604/528 |
| 2011/0065994 A1 | 3/2011 | Kudoh et al. | |
| 2011/0282491 A1 * | 11/2011 | Prisco | A61B 34/71 700/258 |
| 2012/0123441 A1 * | 5/2012 | Au | A61B 19/2203 606/130 |
| 2013/0102960 A1 * | 4/2013 | Miyoshi | A61B 1/00066 604/95.04 |
| 2013/0218005 A1 * | 8/2013 | Desai | A61B 19/2203 600/424 |
| 2013/0321262 A1 * | 12/2013 | Schecter | G06F 3/041 345/156 |
| 2014/0031626 A1 * | 1/2014 | Schwarz | A61B 1/00114 600/149 |
| 2014/0135580 A1 * | 5/2014 | Omoto | A61B 1/00039 600/148 |
| 2014/0171741 A1 * | 6/2014 | Okamoto | A61B 1/0057 600/149 |
| 2015/0173731 A1 * | 6/2015 | Lohmeier | A61B 19/2203 606/1 |
| 2015/0313447 A1 * | 11/2015 | Arai | G02B 23/2476 600/146 |
| 2016/0213438 A1 * | 7/2016 | Jogasaki | A61B 1/0016 |

FOREIGN PATENT DOCUMENTS

| | | |
|---|---|---|
| JP | 03-236824 A | 10/1991 |
| JP | 2000-279376 B2 | 10/2000 |
| JP | 2009-002387 A | 1/2009 |
| JP | 2010-213969 A | 9/2010 |

\* cited by examiner

180° (down)     180° (up)

INSERTION APPARATUS

CROSS REFERENCE TO RELATED APPLICATIONS

This application is a continuation application of PCT/JP2013/050651 filed on Jan. 16, 2013 and claims benefit of Japanese Applications No. 2012-006301 filed in Japan on Jan. 16, 2012, No. 2012-011326 filed in Japan on Jan. 23, 2012, No. 2012-023182 filed in Japan on Feb. 6, 2012, No. 2012-023183 filed in Japan on Feb. 6, 2012, the entire contents of each of which are incorporated herein by their reference.

BACKGROUND OF THE INVENTION

1. Field of the Invention

The present invention relates to an insertion apparatus including a drive section that electrically pulls a pulling member inside an endoscope operation portion including a bending operation apparatus, the pulling member making a bending portion provided in an insertion portion bend.

2. Description of the Related Art

In recent years, in a medical field or an industrial field, endoscopes including an elongated insertion portion have been used. With the endoscopes in the medical field, i.e., the insertion portion is inserted into a body from, e.g., the oral cavity or the anus to perform, e.g., observation. On the other hand, with the endoscopes in the industrial field, the insertion portion is inserted into, e.g., a piping or an engine to perform, e.g., observation.

In the endoscopes, in general, an observation optical system is provided in a distal end portion of the insertion portion. Also, on the distal end side of the insertion portion, a bending portion that bends, for example, upward, downward, leftward and rightward is provided. Furthermore, at a proximal end of the insertion portion, an operation portion including a bending operation apparatus is provided.

Then, for example, bending knobs, which provide the bending operation apparatus, and, for example, distal end bending pieces included in the bending portion are joined via wires, which are pulling members. An endoscope configured as described above enables an operator to operate the bending knobs via the fingers of his hand grasping the operation portion to pull or slacken the wires to bend the bending portion.

In recent years, motorized bending endoscopes that include drive means provided inside an operation portion of the endoscopes and enable a bending portion to be bent by operating one manipulator via fingers, the manipulator being a bending operation apparatus provided in a standing manner on the operation portion have been proposed. For example, Japanese Patent No. 3549434 indicates a motorized bending-type endoscope that is excellent in operability and independently detects a bending angle of a bending tube portion of an insertion portion and an external force applied to the bending tube portion, enabling correct recognition of the state of the bending tube portion.

The motorized bending-type endoscope includes a tensile force sensor that detects a tensile force of an angle wire, which is a pulling member, and a displacement sensor that detects a displacement of the angle wire. Also, the motorized bending-type endoscope includes means for calculating a difference value between the detected tensile force of the angle wire and a tensile force set in advance for the detected displacement of the angle wire in a state where a distal end portion of the insertion portion is not subjected to an external force. The motorized bending-type endoscope is configured so that if the distal end portion of the insertion portion is subjected to an external force when a bending portion is bent, the bending operation apparatus is actuated according to an amount of force corresponding to the difference value to make an operator aware of the reception of the external force.

SUMMARY OF THE INVENTION

An insertion apparatus according to an aspect of the present invention includes:

BRIEF DESCRIPTION OF THE DRAWINGS

FIG. 1 is a block diagram illustrating a configuration of a motorized bending endoscope including a haptic section;

FIGS. 2 and 3 relate to a motorized bending endoscope that includes a bending portion that bends in two directions, i.e., upward and downward, the motorized bending endoscope allowing provision of an instruction to bend the bending portion by operating a manipulator, and FIG. 2 is a top view illustrating a configuration of a haptic section of the endoscope;

FIG. 3 is a side view of the endoscope in FIG. 2;

FIG. 4 is a diagram illustrating a configuration of an endoscope with protection springs provided in partway of respective bending wires;

FIG. 5 is a diagram illustrating a configuration of an endoscope with ends of transmission wires fixed to respective bending wires at respective positions on the operation portion side relative to a bending portion in an insertion portion;

FIG. 6 is a top view illustrating a configuration of a haptic section of the endoscope;

FIG. 7 is a side view of the endoscope in FIG. 6;

FIG. 8 is a diagram illustrating a relationship between the manipulator and transmission wires from the back side of the endoscope in FIG. 6;

FIG. 9 is a top view illustrating another configuration of a haptic section of the endoscope;

FIG. 10 is a side view of the endoscope in FIG. 9;

FIG. 13 is a side view illustrating the endoscope including a haptic section;

FIG. 14 is a diagram illustrating a configuration of the haptic section;

FIG. 15 is a cross-sectional view along line Y15-Y15 in FIG. 14 and is a diagram illustrating a relationship among hooked springs, a pulley and a rotating shaft portion;

FIG. 16 includes a diagram illustrating a configuration of a distal end face of a rotating shaft portion integrated with the bending operation knob included in the haptic section and a diagram illustrating a configuration of one face of the pulley arranged so as to face the distal end face;

FIG. 17 is a diagram illustrating an operation of the haptic section of the endoscope;

FIGS. 18 to 20D relate to a third embodiment, and FIG. 18 is a side view illustrating a configuration of a motorized bending endoscope that senses external resistance exerted on the distal end side of an insertion portion during a bending operation of a bending portion;

FIG. 19 is a top view of the motorized bending endoscope in FIG. 18;

FIG. 20D is a diagram illustrating a relationship among the first pulling member, the winding portion and the second pulling member where a distal end portion of the insertion portion comes into contact with an inner wall during a bending operation of the bending portion included in the insertion portion;

FIGS. 21 to 26C relate to a first embodiment of appendices, and FIG. 21 is a diagram illustrating an endoscope with a manipulator provided in a standing manner at an operation portion, the manipulator providing a bending operation apparatus;

FIG. 22 is a diagram illustrating the endoscope, which includes a suspension frame to be operated via the manipulator, pulleys with bending wires fixed thereto, drive sections and drive force transmission sections in the operation portion;

FIG. 23 is a diagram illustrating a relationship among the manipulator, the suspension frames, the pulleys with the bending wires fixed thereto, the drive sections and the drive force transmission sections as the operation portion of the endoscope in FIG. 22 is viewed from a top of the manipulator;

FIG. 24 is a diagram illustrating a relationship between the suspension frame, the pulleys with the bending wires fixed thereto, disc springs, a drive gear portion and driven gears;

FIG. 25 is a diagram illustrating an operation to bend the bending portion upward;

FIG. 26C is a diagram illustrating a state in which the bending wire is pulled maximally as a result of the pulley being depressed to a predetermined position;

FIGS. 27 to 31D relate to a second embodiment of the appendices, and FIG. 27 is a diagram illustrating an endoscope including an up/down operation dial and a left/right operation dial at an operation portion, the up/down operation dial and the left/right operation dial providing a bending operation apparatus;

FIG. 28 is a diagram illustrating a relationship among a shaft portion of an up/down bending knob and a shaft portion of a left/right bending knob, an up/down cam shaft and a left/right cam shaft, a cam shaft gear, an up/down pulley section, a left/right pulley section, a drive force transmission section, a motor and a plurality of bending wires, which are provided in the operation portion;

FIG. 29 is a side view illustrating a configuration of the endoscope and is a diagram illustrating a relationship among the up/down bending knob and the left/right bending knob, an up/down wire fixing pulley and a left/right wire fixing pulley, and the bending wires;

FIG. 30 is an enlarged view of the inside of the operation portion in FIG. 8;

FIG. 31D is a diagram illustrating a relationship among the shaft portion of the left/right bending knob, the left/right cam shaft, the left/right pulley section, the drive force transmission section, the motor and a right bending wire when the bending portion is bent rightward;

FIGS. 33 to 36B relate to a modification of the second embodiment of the appendices, and FIG. 33 is a side view illustrating a configuration of an endoscope, which is a diagram illustrating an operation dial included in an operation portion, and an up pulley with an up bending wire fixed thereto, a friction plate and a pulley moving body provided in the operation portion;

FIG. 34 is a diagram of the operation portion of the endoscope in FIG. 33 as viewed in an arrow Y34 direction, which is a diagram illustrating a relationship among the up pulley with the up bending wire fixed thereto, the friction plate, the pulley moving body and a shaft portion of the operation dial;

FIG. 36B is a diagram illustrating a relationship among the up pulley, the friction plate, the pulley moving body and the shaft portion of the operation dial when the bending portion is in a maximal bending state;

FIG. 37 is a diagram illustrating an endoscope including a drive section and a drive force transmission section in an operation portion;

FIG. 38 is a diagram illustrating a relationship among a manipulator, a drive force transmission section including a suspension frame, operation input transmission wires and a pressing plate and a pulley;

FIG. 39 is a diagram illustrating operations of a drive force transmission section and a pulley;

FIG. 40 is a diagram illustrating an endoscope including a belt, which serves as a drive section, in an operation portion;

FIG. 42 is a diagram illustrating an endoscope including an operation dial, which provides a bending operation apparatus, in an operation portion;

FIG. 43 is a diagram illustrating a relationship among the operation dial, a drive force transmission section and an ultrasound motor;

DETAILED DESCRIPTION OF THE PREFERRED EMBODIMENTS

A first embodiment of the present invention will be described below with reference to FIGS. 1 to 5.

Figure 1:
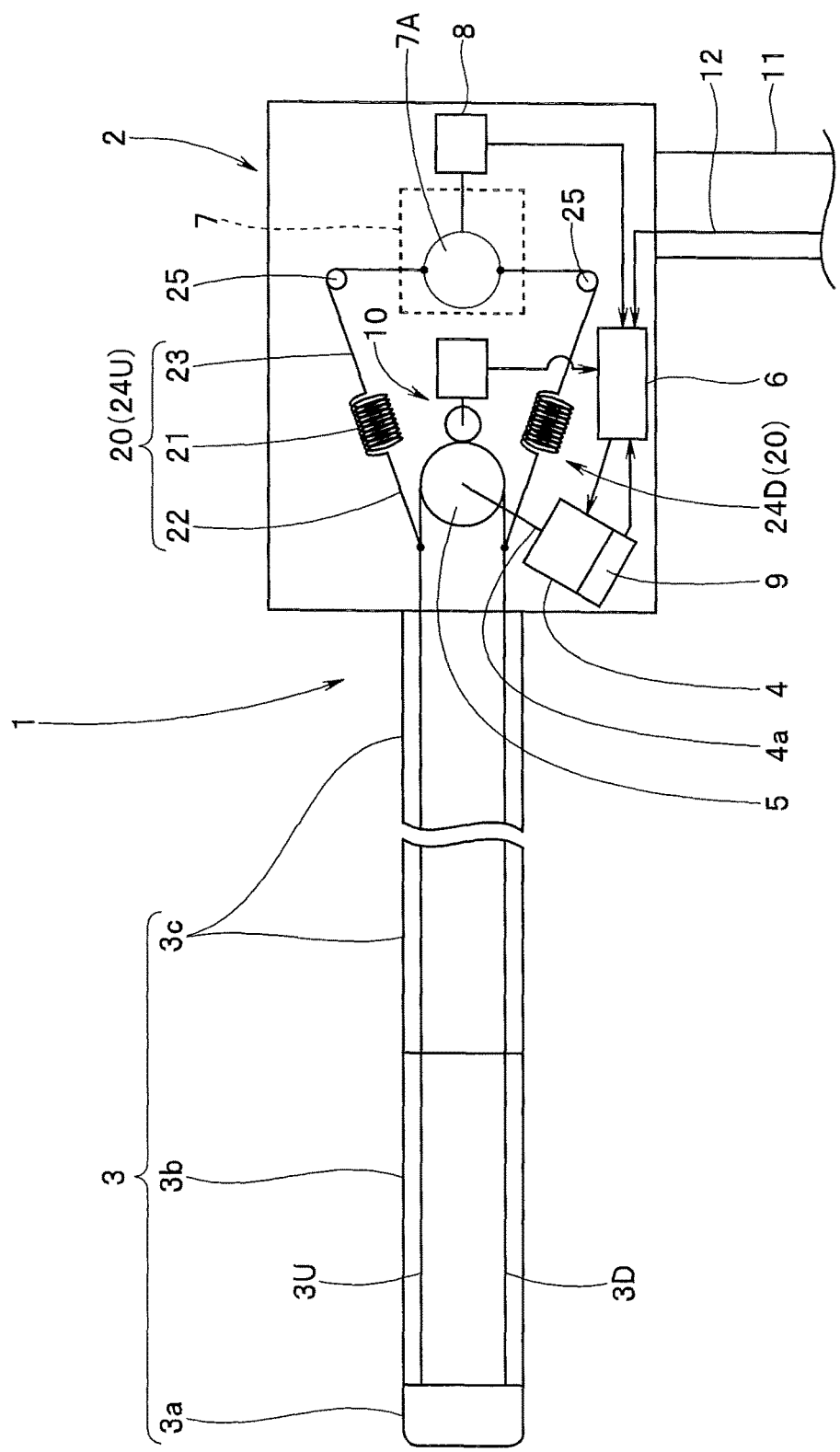
FIGS. 1 to 5 relate to a first embodiment.

An endoscope 1, which is illustrated in FIG. 1, is a medical device as well as an insertion apparatus. The endoscope 1 is a motorized bending endoscope including, for example, a motor 4 that drives a later-described bending portion 3*b* of an insertion portion 3 to bend, in, for example, an operation portion 2.

The motor 4, which is a bending drive section, is, for example, a pulse motor. A pulley 5, which serves as a pivoting member, is fixed integrally to a drive shaft 4*a* of the motor 4. The motor 4 is driven and controlled by a bending control section 6.

The insertion portion 3 is configured in such a manner that a rigid distal end portion 3*a*, a bendable bending portion 3*b* and a flexible tube portion 3*c* having a long length and flexibility are continuously provided in this order from the distal end side. In a non-illustrated distal end face of the distal end portion 3*a*, i.e., an observation window, an illumination window and a treatment instrument opening are provided. An image pickup apparatus including an image pickup device such as a CCD or C-MOS is incorporated inside the distal end portion 3*a*.

The bending portion 3*b* is configured to bend in two or four directions as a result of, for example, a plurality of non-illustrated bending pieces being pivotally joined to one another. The bending portion 3*b* in FIG. 1 is configured to bend, for example, upward/downward. A distal end (hereinafter referred to as "first end"), which is an end of an up bending wire (hereinafter abbreviated as "up wire") 3U and a first end of a down bending wire (hereinafter abbreviated as "down wire") 3D are fixed at respective predetermined positions on a distalmost end bending piece (not illustrated).

A proximal end (hereinafter, a proximal end on the opposite side of a distal end is referred to as "second end"), which is the other end of the up wire 3U, is fixed at a predetermined position on the pulley 5, and a second end of the down wire 3D is fixed at a predetermined position on the pulley 5.

The operation portion 2 includes a grasping portion (not illustrated) to be grasped by, for example, a surgeon and an operation portion body (not illustrated). In the operation portion body, a bending operation apparatus 7 such as a later-described manipulator or a bending operation knob is provided.

Inside the operation portion 2, a shaft portion 7A of the bending operation apparatus 7, a later-described input instruction detecting section 8, an encoder 9, a potentiometer 10 and a later-described haptic section 20 are provided in addition to the motor 4, the pulley 5 and the bending control section 6.

The bending operation apparatus 7, which is an apparatus for providing an operation instruction to bend the bending portion 3*b*, is operated by a surgeon. If a surgeon operates the bending operation apparatus 7 in order to bend the bending portion 3*b*, the shaft portion 7A operates integrally with the bending operation apparatus 7.

The input instruction detecting section 8 detects an amount of operation of the shaft portion 7A that operates upon the bending operation apparatus 7 being operated. The input instruction detecting section 8 outputs a result of the detection to the bending control section 6 as an operation input instruction signal. The encoder 9 detects a rotational position of the motor 4, and outputs the rotational position to the bending control section 6 as motor position information. The potentiometer 10 detects a rotational position of the pulley 5 and outputs the rotational position to the bending control section 6 as pulley position information.

In other words, the operation input instruction signal, the motor position information and the pulley position information are inputted to the bending control section 6.

The bending control section 6 performs arithmetic processing based on the operation input instruction signal, the motor position information and the pulley position information to calculate a motor drive signal, and outputs the drive signal to the motor 4. The motor 4 is driven and controlled by the motor drive signal. As a result, the bending wire 3U or 3D corresponding to the operation input instruction signal is moved to advance/retract, whereby the bending portion 3*b* bends.

The haptic section 20 is a notification mechanism that, during a bending operation performed by a surgeon, makes the surgeon sensuously aware of, e.g., the distal end portion 3*a* of the insertion portion 3 coming into contact with, e.g., a body wall, through a hand of the surgeon that is operating the bending operation apparatus 7.

The haptic section 20 includes haptic transmission wires (hereinafter also abbreviated as "transmission wires") 24. Each transmission wire 24 includes a spring 21, a first joining wire 22 and a second joining wire 23. The spring 21 is an elastic portion that elastically extends and provides a predetermined elastic force. The joining wires 22 and 23 each have predetermined flexibility and stiffness.

In the present embodiment, the haptic section 20 includes an up transmission wire 24U and a down transmission wire 24D.

Each first joining wire 22 provides the first end side of the respective transmission wire 24. A first end of each first joining wire 22 is fixed at a predetermined position on the respective bending wire 3U or 3D. Each second joining wire 23 provides the second end side of the respective transmission wire 24. A second end of each second joining wire 23 is fixed at a respective predetermined position on the shaft portion 7A of the bending operation apparatus 7.

The transmission wires 24U and 24D are arranged so as to run in such a manner that the transmission wires 24U and 24D are tightened with a predetermined tensile force via at least one idler 25 when the bending portion 3b is in a straightened state. In such arrangement, the respective spring 21 is in a predetermined expanded state.

Note that a second end of the first joining wire 22 is joined to the first end side of the spring 21, and a first end of the second joining wire 23 is joined to the second end side of the spring 21.

Reference numeral 11 denotes a universal cord. At an end portion of the universal cord 11, a connector (not illustrated) is provided. The connector is detachably connected to, e.g., a light source apparatus (not illustrated), which is an external apparatus.

Reference numeral 12 denotes an electric wire. The electric wire 12 is inserted through the universal cord. The electric wire 12 supplies power to, e.g., the motor 4 via the bending control section 6.

In the above-described embodiment, it is assumed that the bending control section 6 is provided inside the operation portion 2. However, e.g., a configuration in which the bending control section 6 is provided inside the light source apparatus or a configuration in which the bending control section 6 is provided inside a video processor (not illustrated), which is an apparatus external to the endoscope 1, may be employed. In this configuration, a signal wire is inserted through the universal cord to output the motor drive signal calculated by the bending control section 6 to the motor 4.

Furthermore, in the present embodiment, a diameter dimension of the pulley 5 is set to a predetermined dimension. A gear ratio of the motor 4 that rotates the pulley 5 is set to a predetermined value. More specifically, the gear ratio is set so that if, during a bending operation of the distal end portion 3a of the bending portion 3b, a predetermined force is externally provided to the distal end portion 3a of the bending portion 3b in a direction opposite to a direction of the bending, the bending of the bending portion 3b is halted by the external force and if a force exceeding that force is provided, the bending portion 3b rotates in the opposite direction.

Figure 3:
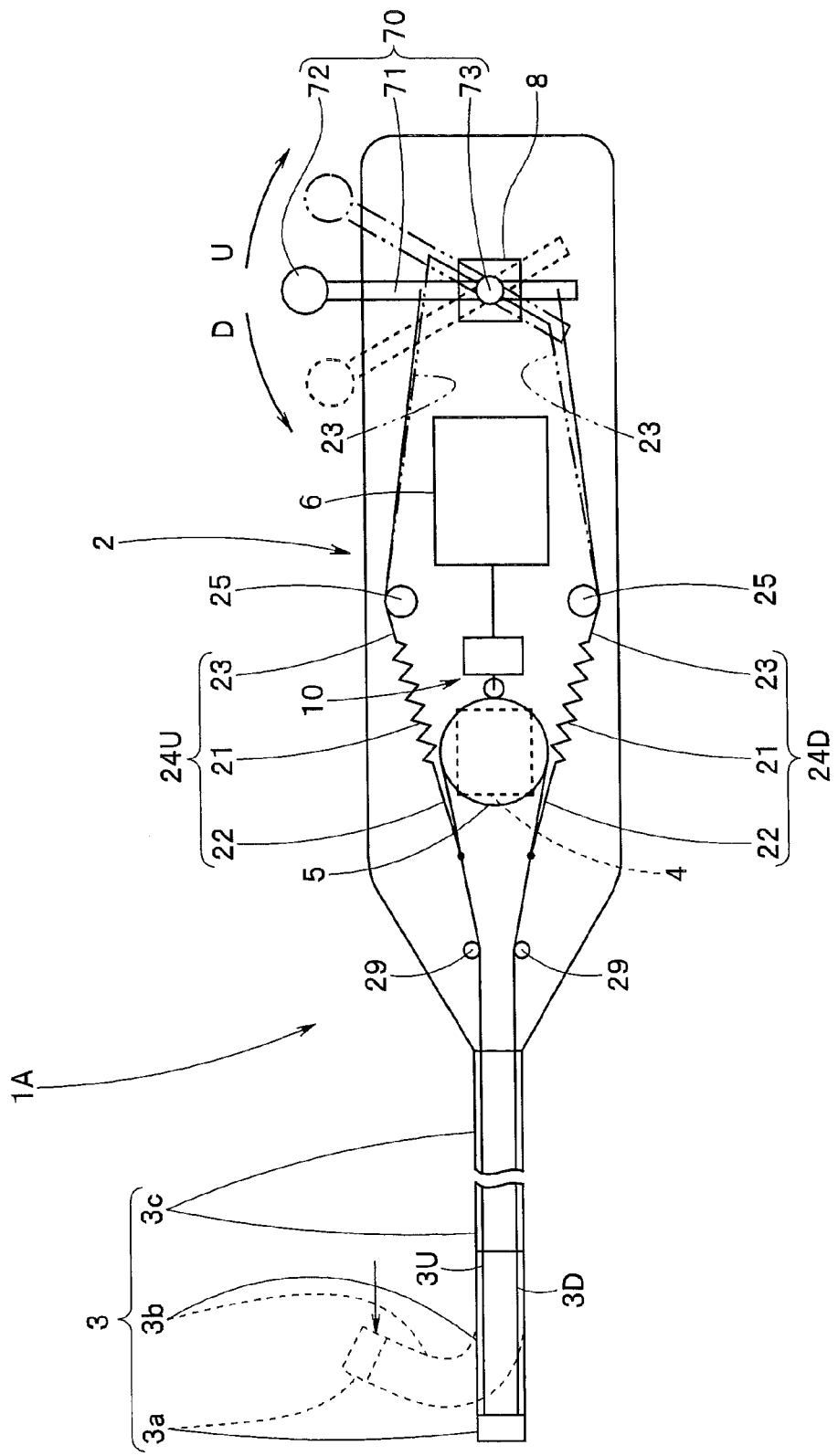

In other words, as indicated by alternate the long and two short dashes lines in FIG. 3, if, during upward bending of the bending portion 3b, an external force in the F1 direction that interrupts the bending of the bending portion 3b is exerted on the bending portion 3b, a rotation torque in a direction opposite to that of the motor 4 that pulls the up wire 3U inside the insertion portion 3 is generated at a rotating shaft of the pulley 5. Then, if the rotation torque for the rotating shaft of the pulley 5, which is provided by the external force in the F1 direction, becomes larger than the rotation torque of the motor 4, a rotating shaft of the motor 4 passively makes reverse rotation. Then, the transmission wire 24U expands, whereby such state change is transmitted to the bending operation apparatus 7 via the transmission wire 24U to give a haptic sensation.

A configuration and operation of an endoscope including a bending portion that bends in two directions, i.e., upward and downward, the endoscope allowing provision of an instruction to bend the bending portion by operating a manipulator, which serves as a bending operation apparatus, will be described with reference to FIGS. 2 and 3.

Figure 2:
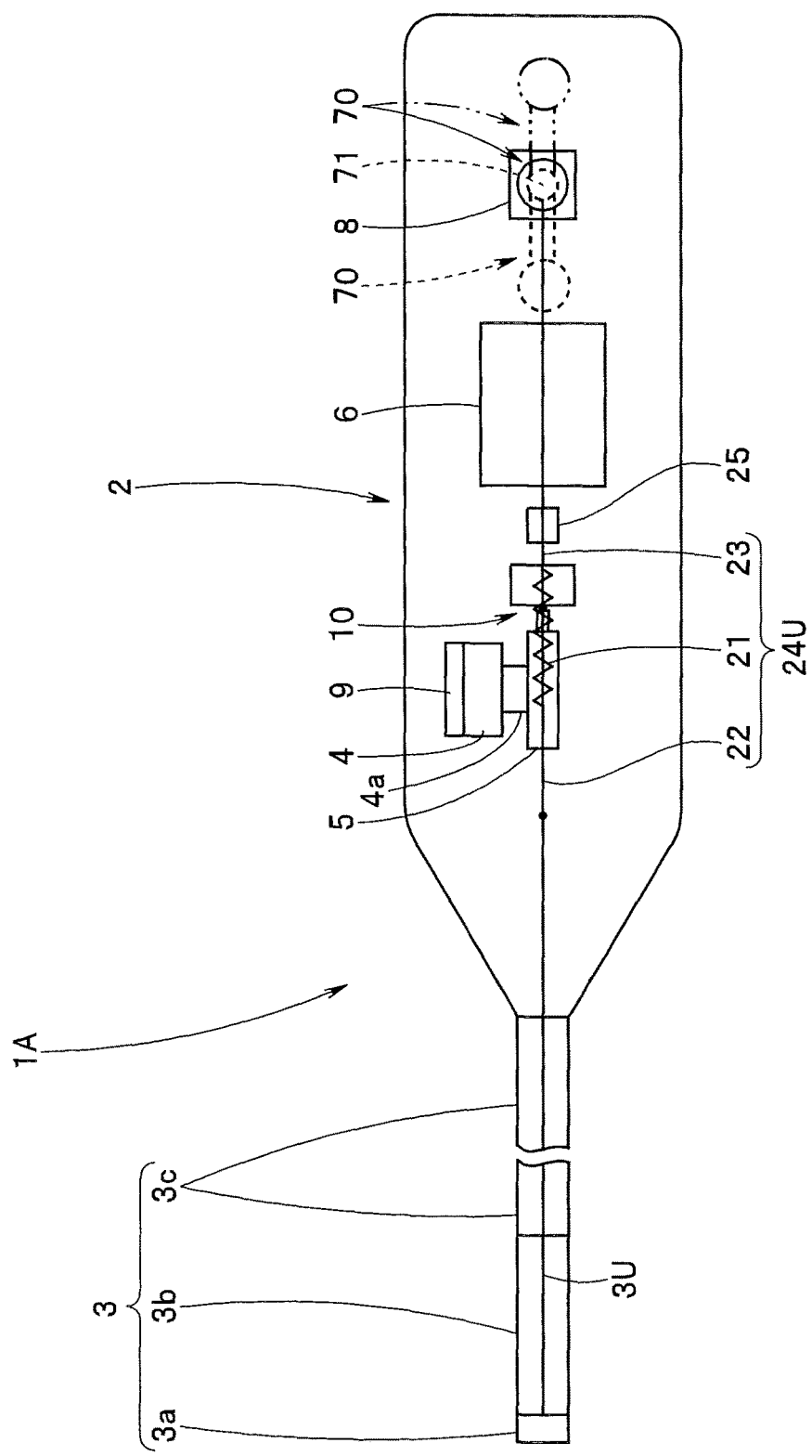

An endoscope 1A according to the present embodiment, which is illustrated in FIGS. 2 and 3, includes a manipulator 70, which serves as a bending operation apparatus 7, in an operation portion 2. The manipulator 70 includes an elongated shaft portion 71 and a knob 72. The shaft portion 71 is configured so as to be pivotable about a pivot axis 73. The manipulator 70 can be tilted in two directions, i.e., the arrow U direction and the arrow D direction in FIG. 3.

An input instruction detecting section 8 is a tilting operation amount detection apparatus. The input instruction detecting section 8 detects a direction and an angle of tilting of the shaft portion 71 as a tilting operation amount and outputs a result of the detection to the bending control section 6 as an operation input instruction signal.

A first joining wire 22 on the first end side of an up transmission wire 24U is fixed at a predetermined position on the insertion portion 3 side of an up wire 3U relative to the pulley 5. A second joining wire 23 on the second end side of the up transmission wire 24U is fixed at, for example, a position a distance L away from the pivot axis 73 of the shaft portion 71 to the knob 72 side. The distance L is set in consideration of a diameter dimension of the pulley 5.

On the other hand, a first joining wire 22 on the first end side of a down transmission wire 24D is fixed at a predetermined position on the insertion portion 3 side of a down wire 3D relative to the pulley 5. A second joining wire 23 on the second end side of the down transmission wire 24D is fixed at a position the distance L away from the pivot axis 73 of the shaft portion 71 to the shaft end side.

Note that in the above description, it is assumed that the first joining wires 22 are fixed at the respective predetermined positions on the insertion portion 3 side of the wires 3U and 3D relative to the pulley 5. However, the first joining wires 22 may be joined to the pulley.

The transmission wires 24U and 24D are arranged so as to run inside the operation portion 2 in such a manner that the transmission wires 24U and 24D are tightened with a predetermined tensile force via an idler 25 when the bending portion 3b is in a straightened state. Here, the spring 21 is in a predetermined expanded state.

Note that the up wire 3U and the down wire 3D run so as to be guided to the pulley 5 via, e.g., respective guide rollers 29.

When a surgeon tilts the manipulator 70 as indicated by the alternate long and two short dashes lines, the up transmission wire 24U is pulled and the down transmission wire 24D is slackened with the tilting of the manipulator 70. As a result, the straightened bending portion 3b is bent upward.

Also, with the tilting of the manipulator 70, an operation input instruction signal corresponding to an amount of the tilting is outputted from the input instruction detecting section 8 to the bending control section 6.

The bending control section 6 calculates a motor drive signal from the inputted operation input instruction signal and outputs the calculated motor drive signal to the motor 4.

The motor 4 is driven and controlled by the motor drive signal. With the driving of the motor 4, the pulley 5 is rotated clockwise in FIG. 3. As a result, the up wire 3U is pulled by the rotation of the pulley 5 and the down wire 3D is slackened by the rotation of the pulley 5. In other words, the bending portion 3b gradually bends upward. At this time, with the bending of the bending portion 3b, the slackened down wire 3D is pulled in a direction opposite to that of the up wire 3U by elasticity of the corresponding spring 21.

The first end of the up transmission wire 24U is fixed to the up wire 3U. On the other hand, the first end of the down transmission wire 24D is fixed to the down wire 3D. As a result, the first end of the up transmission wire 24U moves toward the pulley 5 together with the up wire 3U pulled by the pulley 5. On the other hand, the first end of the down transmission wire 24D moves toward the insertion portion 3 together with the down wire 3D pulled as a result of the bending of the bending portion 3b.

In the present embodiment, a first movement distance of movement of the first end side of the up transmission wire 24U accompanying the up wire 3U is set to be shorter than a second movement distance of movement of the second end side of the up transmission wire 24U accompanying the tilting of the manipulator 70. As a result, during the bending operation, the up transmission wire 24U, which runs via the corresponding idler 25 described above, maintains the state of running with the predetermined tensile force by means of the corresponding spring 21 in an expanded state being expanded.

On the other hand, a third movement distance of movement of the first end side of the down transmission wire 24D accompanying the down wire 3D is set to be shorter than a fourth movement distance of movement of the second end side of the down transmission wire 24D accompanying the tilting of the manipulator 70. As a result, during the bending operation, the down transmission wire 24D, which runs via the corresponding idler 25 described above, maintains the state of running with the predetermined tensile force by means of the corresponding spring 21 in an expanded state being further compressed.

Accordingly, as the surgeon increases the tilting angle of the manipulator 70 to the up direction, whereby the bending portion 3b continuously bends upward. At this time, the spring 21 of the up transmission wire 24U continuously expands and the spring 21 of the down transmission wire 24D continuously compresses. As a result, the transmission wires 24U and 24D are maintained in the state of running with the predetermined tensile force.

During the bending operation, if the distal end portion 3a abuts against, e.g., a body wall, a reactive force applied to the bending portion 3b increases, which causes a change in the bending operation. Then, when the reactive force applied to the bending portion 3b reaches a predetermined strength amount, the pulling of the up wire 3U is halted despite the state in which the up wire 3U is continuously pulled by the rotation of the pulley 5. As a result, the upward bending operation of the bending portion 3b is halted. Also, with the halt of the upward bending operation of the bending portion 3b, the pulling of the down wire 3D resulting from the bending of the bending portion 3b is also halted. Then, continuous expansion of the spring 21 of the down transmission wire 24D is halted.

At this time, the tilting operation by the surgeon is continued. Accordingly, the spring 21 of the up transmission wire 24U is further expanded. On the other hand, the continuous compression of the spring 21 of the down transmission wire 24D is halted and the spring 21 is further expanded because of the tilting operation being continued. Then, a load for moving the shaft portion 71 in the up direction is transmitted from the spring 21 of the up transmission wire 24U to the shaft portion 71 via the corresponding second joining wire 23. As a result, a change is generated in operational feeling such as an increase in amount of tilting operation strength of a hand of the surgeon that is performing the tilting operation of the manipulator 70. In other words, during a bending operation, the surgeon can become aware that, e.g., the distal end portion 3a of the bending portion 3b abuts against, e.g., a body wall.

As described above, in the endoscope 1A that allows the bending portion 3b to bend upward/downward by driving the motor 4 to tilt the manipulator 70 without the up wire 3U or the down wire 3D being directly pulled, the up transmission wire 24U including the spring 21 is joined to the up wire 3U and also to the manipulator 70, and the down transmission wire 24D is joined to the down wire 3D and also to the manipulator 70. Then, the transmission wires 24U and 24D are brought into a running state in which the transmission wires are tightened with a predetermined tensile force via the respective idlers 25.

As a result, upon a tilting operation of the manipulator 70, the up wire 3U or the down wire 3D is pulled by a drive force from the motor 4, whereby the bending portion 3b can be bent. Then, in case where the distal end portion 3a abuts, e.g., a body wall and thereby a change occurs in bending operation of the bending portion 3b or the bending operation halts, a load is provided to the manipulator 70 from the spring 21 included in the transmission wire whose first end is joined to the bending wire pulled as a result of the bending operation via the corresponding second joining wire 23. Upon the load being provided on the manipulator 70, a change in operation feeling occurs in the hand of the surgeon that is tilting the manipulator 70 as if the surgeon directly pulls the bending wire 3U or 3D via the bending operation apparatus. As a result, during a bending operation by the motor 4, the surgeon sensuously determines that, e.g., the distal end portion 3a of the bending portion 3b abuts against, e.g., a body wall, through the manipulator 70 the surgeon is tilting.

Note that in a bending state in which the manipulator 70 is tilted to bend the bending portion 3b downward, if a reactive force applied to the bending portion 3b as a result of the distal end portion 3a abutting, e.g., a body wall reaches a predetermined strength amount, the pulling of the down wire 3D is halted, whereby the downward bending operation of the bending portion 3b is halted. As a result, a load that makes the shaft portion 71 move in a direction opposite to the down direction is transmitted from the spring 21 of the up transmission wire 24U to the shaft portion 71 via the corresponding second joining wire 23. As a result, the surgeon becomes aware of a trouble such as the distal end portion 3a of the bending portion 3b abutting, e.g., a body wall during a bending operation.

Also, in the above-described embodiment, it is assumed that as a result of the gear ratio of the motor 4 that rotates the pulley 5 being arbitrarily set, if a predetermined force is externally received, the rotating shaft of the motor 4 passively makes reverse rotation. However, the gear ratio of the motor 4 that if a predetermined force is externally received, makes the pulley 5 continuously rotate may be used.

Figure 4:
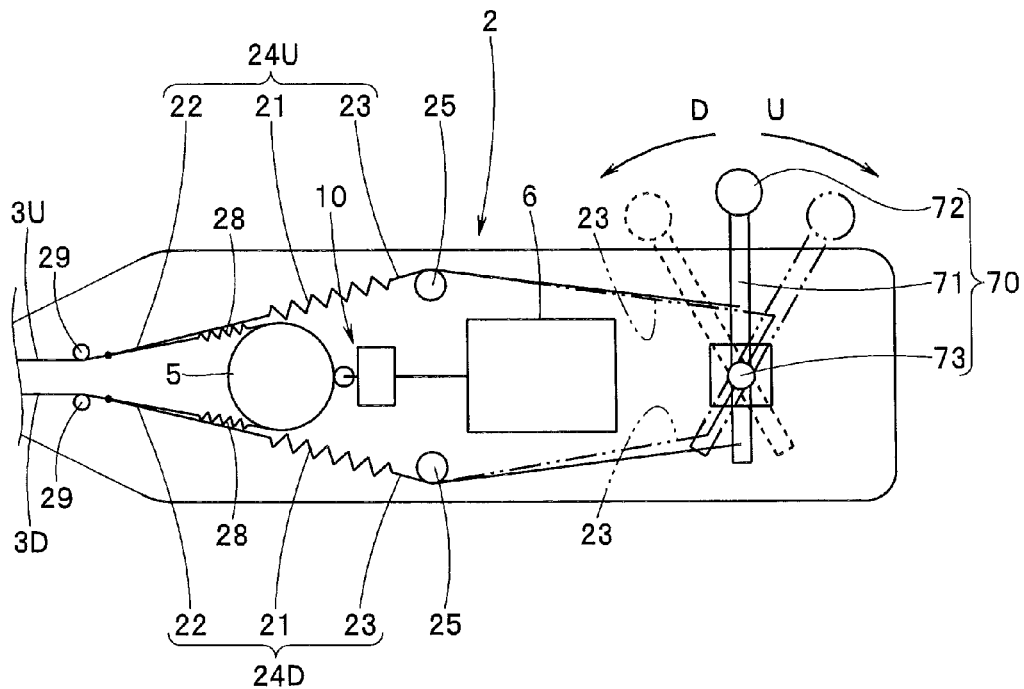

In this case, as illustrated in FIG. 4, protection springs 28 are provided partway of the respective bending wires 3U and 3D. In this configuration, the protection springs 28 are provided on the bending portion 3b side relative to the pulley 5. The first ends of the transmission wires 24U and 24D are fixed further on the bending portion 3b side relative to the respective protection springs 28.

With this configuration, when, e.g., the bending portion 3b touches a body wall, the springs 28 provided in the wires inserted through the insertion portion 3 are expanded or compressed by an elastic force. Then, a change in the state of the springs 28 is transmitted to the manipulator 70 via the transmission wires 24U and 24D as a haptic sensation.

Note that the haptic sensation may be given by using an elastic force of the wires inserted through the insertion portion themselves only.

Figure 5:
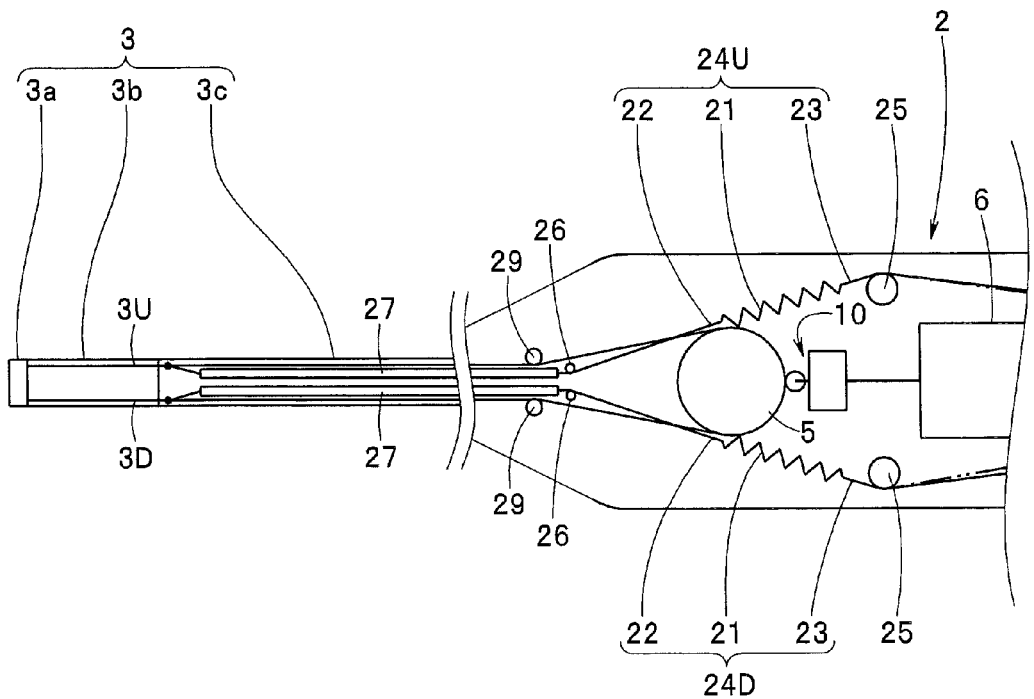

Furthermore, in the above-described embodiment, it is assumed that the first ends of the respective transmission wires 24U and 24D are fixed on the bending portion 3b side relative to the pulley 5 inside the operation portion 2. However, positions where the first ends of the respective transmission wires 24U and 24D are fixed are not limited to positions inside the operation portion 2. In other words, as illustrated in FIG. 5, the first ends of the transmission wires 24U and 24D may be fixed on the operation portion 2 side relative to the bending portion 3b inside the insertion portion 3.

Reference numeral 26 denotes a transmission wire guide roller, and reference numeral 27 denotes a transmission wire projection tube. The respective transmission wire protection tubes 27 prevent the transmission wires 24U and 24D from making contact with objects incorporated in the insertion portion inside the insertion portion 3. The respective transmission wire guide rollers 26 define respective wire running positions so that the respective transmission wires 24U and 24D are smoothly guided from the inside of the operation portion 2 to the inside of the respective transmission wire protection tubes 27.

With this configuration, the first ends of the transmission wires 24U and 24D are arranged in the vicinity of the bending portion, whereby a bending operation of the bending portion 3b is detected with higher accuracy. As a result, a surgeon that is performing a bending operation can more reliably determine detection of a trouble such as the distal end portion 3a of the bending portion 3b abutting, e.g., a body wall, by sensation.

Furthermore, in the above-described embodiment, it is assumed that a bending portion that bends an endoscope in two directions, i.e., upward and downward is provided and an instruction to bend the bending portion is provided by operating a manipulator. However, a bending portion of an endoscope is not limited to one that bend in two directions, i.e., upward and downward, and may be one that bends in four directions, i.e., upward, downward, leftward and rightward. Also, a configuration in which a bending operation of a bending portion is performed via a bending operation knob instead of a manipulator may be employed.

A second embodiment will be described with reference to FIGS. 6 to 8.

In the present embodiment, an endoscope includes a bending portion that bends in four directions, i.e., upward, downward, leftward and rightward. Also, the endoscope is configured so that an instruction to bend the bending portion is provided by operating a manipulator, which is a bending operation apparatus.

Figure 6:
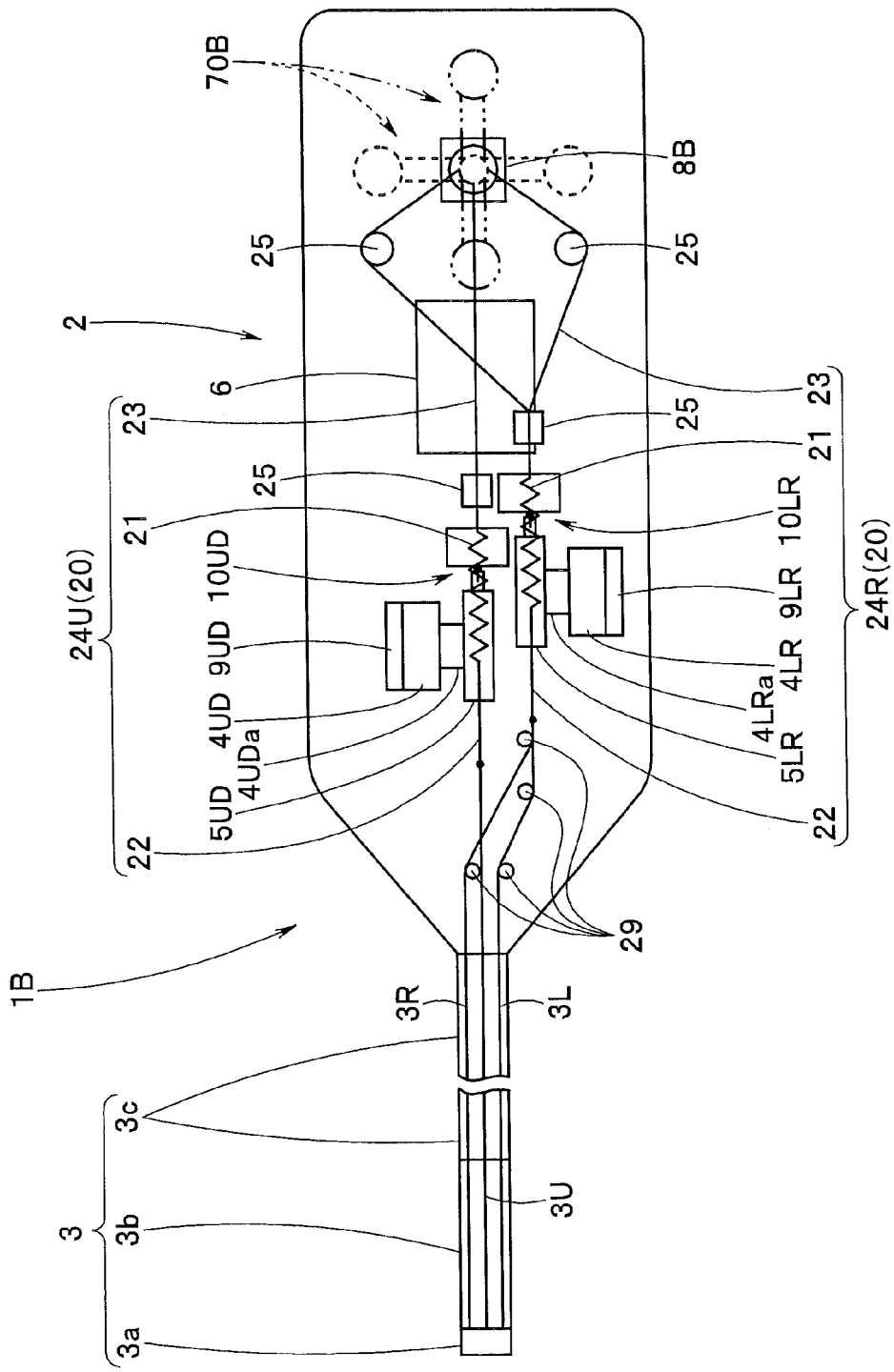
FIGS. 6 to 8 relate to a second embodiment and FIG. 6 relates to a motorized bending endoscope that includes a bending portion that bends in four directions, i.e., upward, downward, leftward and rightward and allows provision of an instruction to bend the bending portion by operating a manipulator.
Figure 7:
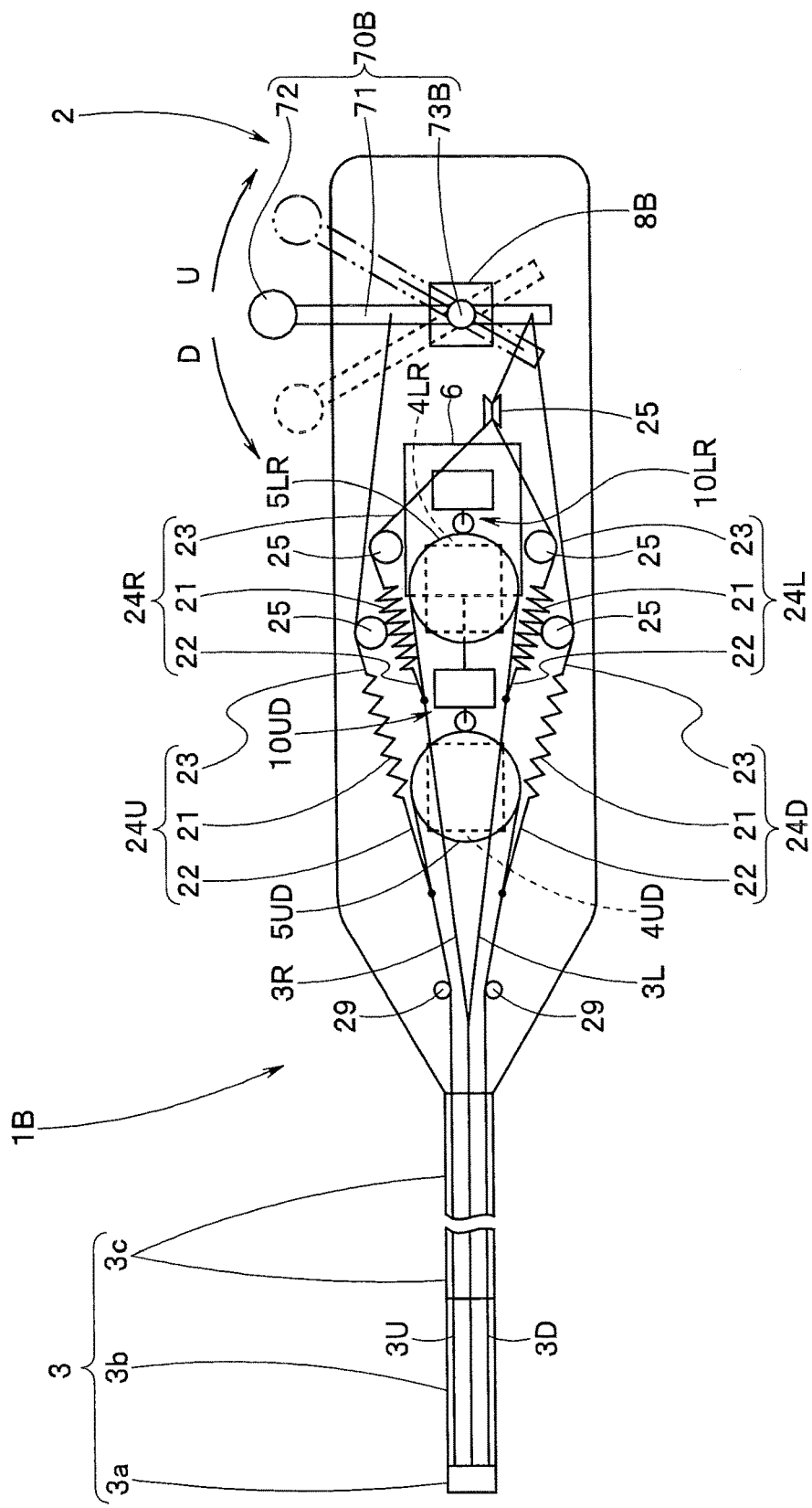

As illustrated in FIGS. 6 and 7, a bending portion 3b of an endoscope 1B is configured to bend leftward and rightward in addition to upward and downward. Accordingly, a first end of a left wire 3L and a first end of a right wire 3R are fixed at respective predetermined positions on a distal-most end bending piece in the bending portion 3b, in addition to a first end of an up wire 3U and a first end of a down wire 3D.

On the other hand, a second end of the up wire 3U and a second end of the down wire 3D are fixed at respective predetermined positions on an up/down pulley 5UD, and a second end of the left wire 3L and a second end of the right wire 3R are fixed at respective predetermined positions on a left/right pulley 5LR.

The up/down pulley 5UD is driven by an up/down motor 4UD, the left/right pulley 5LR is driven by a left/right motor 4LR. A rotational position of the up/down motor 4UD is detected by an up/down encoder 9UD, and a rotational position of the left/right motor 4LR is detected by a left/right encoder 9LR. A rotational position of the up/down pulley 5UD is detected by an up/down potentiometer 10UD, and a rotational position of the left/right pulley 5LR is detected by a left/right potentiometer 10LR. Then, information on the respective motor positions detected by encoders 9UD and 9LR and information on the respective pulley positions detected by the potentiometers 10UD and 10LR are outputted to a bending control section 6.

An operation portion 2 includes a manipulator 70B as a bending operation apparatus 7. The manipulator 70B includes an elongated shaft portion 71 and a knob 72. The shaft portion 71 is pivotable about a pivot axis 73B. In the present embodiment, the manipulator 70B is configured to allow the manipulator 70B to be tiled in each of an upward direction, a direction between the upward direction and a leftward direction, the leftward direction, a direction between the leftward direction and a downward direction, the downward direction, a direction between the downward direction and a rightward direction, the rightward direction and a direction between the rightward direction and the upward direction.

An input instruction detecting section 8B detects a direction and an angle of tilting of the shaft portion 71 as a tilting operation amount. The input instruction detecting section 8B outputs a result of the detection to the bending control section 6 as an operation input instruction signal.

In the present embodiment, the haptic section 20 includes an up transmission wire 24U, a down transmission wire 24D, a left transmission wire 24L and a right transmission wire 24R.

A first joining wire 22 that provides a first end of the up transmission wire 24U is fixed at a predetermined position on the up wire 3U. A second joining wire 23 that provides a second end of the up transmission wire 24U is fixed at a position on the knob 72 side of the shaft portion 71 that is a distance L away from the pivot axis 73.

On the other hand, a first joining wire 22 that provides a first end of the down transmission wire 24D is fixed at a predetermined position on the down wire 3D. A second joining wire 23 that provides a second end of the down transmission wire 24D is fixed at a predetermined position, which is a position on the shaft end side of the shaft portion 71 that is the distance L away from the pivot axis 73.

Also, a first joining wire 22 that provides a first end of the left transmission wire 24L is fixed at a predetermined position on the left wire 3L. A second joining wire 23 that provides a second end of the left transmission wire 24L is fixed at a predetermined position, which is a position on the shaft end side of the shaft portion 71 that is the distance L away from the pivot axis 73.

Furthermore, a first joining wire 22 that provides a first end of the right transmission wire 24R is fixed at a predetermined position on the right wire 3R. A second joining wire 23 that provides a second end of the right transmission wire 24R is fixed at a predetermined position, which is a position on the shaft end side of the shaft portion 71 that is the distance L away from the pivot axis 73.

Figure 8:
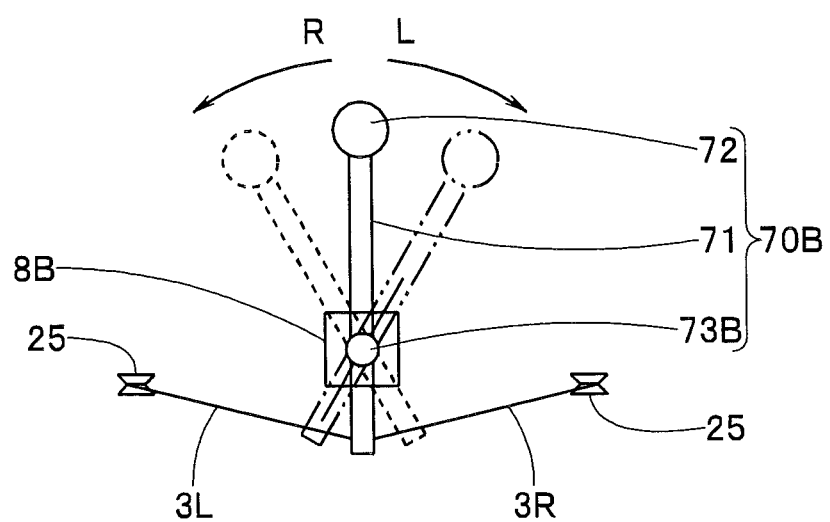

As illustrated in FIGS. 6 to 8, the respective transmission wires 24U, 24D, 24L and 24R run in such a manner that the respective transmission wires 24U, 24D, 24L and 24R are tightened with a predetermined tensile force via respective idlers 25 when the bending portion 3b is in a straightened state. At this time, respective springs 21 are in a predetermined expanded state. Also, the respective bending wires 3U, 3D, 3L and 3R are guided to the respective pulleys 5UD and 5LR via guide rollers 29.

When a surgeon tilts the manipulator 70B to bend the bending portion 3b that is, for example, in a straightened state to bend in any direction of upward, downward, leftward and rightward, an operation input instruction signal corresponding to an amount of the tilting is outputted from the input instruction detecting section 8B to the bending control section 6. The bending control section 6 calculates a motor drive signal from the inputted operation input instruction signal and outputs the calculated motor drive signal to at least either the up/down motor 4UD or the left/right motor 4LR to drive the motor 4UD or 4LR.

The rest of the configuration is similar to that of the above-described embodiment, and members that are the same as those of above-described embodiment are provided with reference numerals that are the same as those of the above-described embodiment and a description thereof will be omitted.

In the present embodiment, for example, when a surgeon tilts the manipulator 70B leftward, the pulley 5LR is rotated with driving of the motor 4LR, whereby the bending wires 3L and 3R are advanced/retracted. As a result, the left wire 3L is pulled and the right wire 3R is slackened by the rotation of the left/right pulley 5LR, whereby the bending portion 3b is gradually bent leftward. At this time, the right wire 3R is pulled in a direction opposite to the left wire 3L with the bending of the bending portion 3b.

Where the bending portion 3b is in a bent state, the running states of the respective transmission wires 24U, 24D, 24L and 24R whose first ends are fixed to the respective bending wires 3U, 3D, 3R and 3L are maintained to be tightened with the predetermined force as a result of the respective springs 21, which is in an expanded state, being compressed or further expanded.

In the present embodiment, as a result of the surgeon continuously tilting the manipulator 70B, the bending portion 3b continuously bends in the leftward direction corresponding to the direction of the tilting. At this time, the spring 21 of the left transmission wire 24L continuously compresses and the spring 21 of the right transmission wire 24R continuously expands. As a result, the transmission wires 24L and 24R are maintained in the state of running with the predetermined tensile force.

During this bending operation, if the distal end portion 3a abuts against, e.g., a body wall and a reactive force applied to the bending portion 3b reaches a predetermined strength amount, the pulling of the left wire 3L is halted despite the state in which the left wire 3L is continuously pulled by the rotation of the corresponding pulley 5. As a result, the leftward bending of the bending portion 3b is halted. Also, with the halt of the leftward bending of the bending portion 3b, the pulling of the right wire 3R resulting from the bending of the bending portion 3b is also halted. Then, the continuous expansion of the spring 21 of the right transmission wire 24R is halted.

At this time, the tilting operation performed by the surgeon is continued. Accordingly, the spring 21 of the left transmission wire 24L is continuously compressed. On the other hand, the continuous expansion of the spring 21 of the right transmission wire 24R is halted and the spring 21 of the right transmission wire 24R is temporarily compressed because of the tilting being continued. Then, a load that makes the shaft portion 71 in a direction opposite to the leftward direction is transmitted to the shaft portion 71 from the spring 21 of the right transmission wire 24R via the corresponding second joining wire 23. As a result, a change occurs in operational feeling such as an increase in amount of tilting operation strength of a hand of the surgeon that is tilting the manipulator 70B leftward. In other words, during the bending operation, the surgeon can become aware of a trouble such as the distal end portion 3a of the bending portion 3b abutting, e.g., a body wall.

As described above, in the endoscope 1B, the bending wires 3U, 3D, 3L and/or 3R are not directly pulled, but the motors 4UD and/or 4LR are driven by operating the manipulator 70B to tilt in order to rotate the pulleys 5UD and/or 5LR and thereby pull the relevant bending wires 3U, 3D, 3L and/or 3R, enabling the bending portion 3b to operate to bend in any direction of upward, downward, leftward and rightward.

Also, the respective bending wires 3U, 3D, 3L and 3R and the manipulator 70B are joined to each other by the respective transmission wires 24U, 24D, 24L and 24R each including the respective spring 21. Then, the respective transmission wires 24U, 24D, 24L and 24R are brought into a running state in which the respective transmission wires 24U, 24D, 24L and 24R are tightened with a predetermined tensile force by the respective idlers 25.

As a result, in a bending operation state in which the manipulator 70B is tilted to pull any of the bending wires 3U, 3D, 3L and 3R by means of a drive force from the motor 4UD or 4LR, if the distal end portion 3a abuts against, e.g., a body wall, a load is transmitted from the springs 21 included in the respective transmission wires 24U, 24D, 24L and 24R via the respective second joining wires 23. As a result, the surgeon can become aware of a trouble such as the distal end portion 3a of the bending portion 3b abutting against, e.g., a body wall during a bending operation.

Note that, in a bending state in which the manipulator 70B is tilted to bend the bending portion 3b rightward, if a reactive force applied to the bending portion 3b as a result of the distal end portion 3a abutting against, e.g., a body wall reaches a predetermined strength amount, pulling of the right wire 3R is halted, whereby the rightward bending of the bending portion 3b is halted. Also, if pulling of the left wire 3L resulting from the bending of the bending portion 3b is halted with the halt of the rightward bending of the bending portion 3b, continuous expansion of the spring 21 of the left transmission wire 24L is halted. As a result, a load that makes the shaft portion 71 move in a direction opposite to the rightward direction is transmitted from the spring 21 of the left transmission wire 24L to the shaft portion 71 via the corresponding second joining wire 23. As a result, a surgeon can become aware of a trouble such as the distal end portion 3a of the bending portion 3b abutting, e.g., a body wall during a bending operation.

Other operations and effects are similar to those of the above-described embodiment.

In the above-described embodiment, the second joining wire 23 that provides the second end of the up transmission wire 24U is fixed at the position on the knob 72 side of the shaft portion 71 that is the distance L away from the pivot axis 73. On the other hand, the second joining wire 23 that provides the second end of the down transmission wire 24D, the second joining wire 23 that provides the second end of the left transmission wire 24L and the second joining wire 23 that provides the second end of the right transmission wire 24R are fixed at respective predetermined positions that are positions on the shaft end side of the shaft portion 71 that is the distance L away from the pivot axis 73.

However, the second joining wire 23 that provides the second end of the up transmission wire 24U may be fixed on the shaft end side of the shaft portion 71, in addition to the second joining wire 23 that provides the second end of the down transmission wire 24D, the second joining wire 23 that provides the second end of the left transmission wire 24L and the second joining wire 23 that provides the second end of the right transmission wire 24R.

Figure 9:
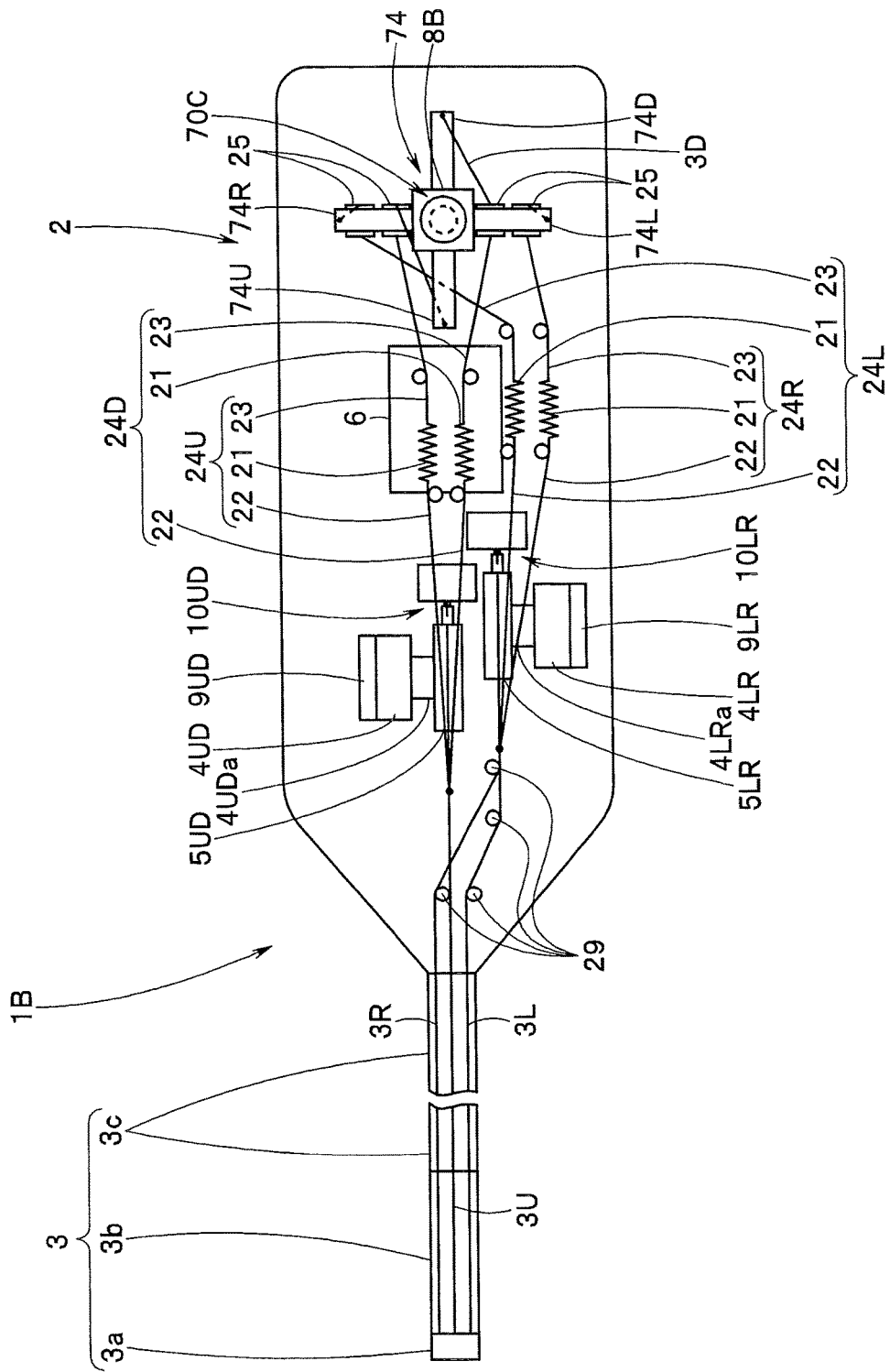
FIGS. 9 and 10 relate to a modification of the second embodiment and FIG. 9 relates to a motorized bending endoscope that includes a bending portion that bends in four directions, upward, downward, leftward and rightward and allows provision of an instruction to bend the bending portion by operating a manipulator integrated with a suspension frame.
Figure 10:
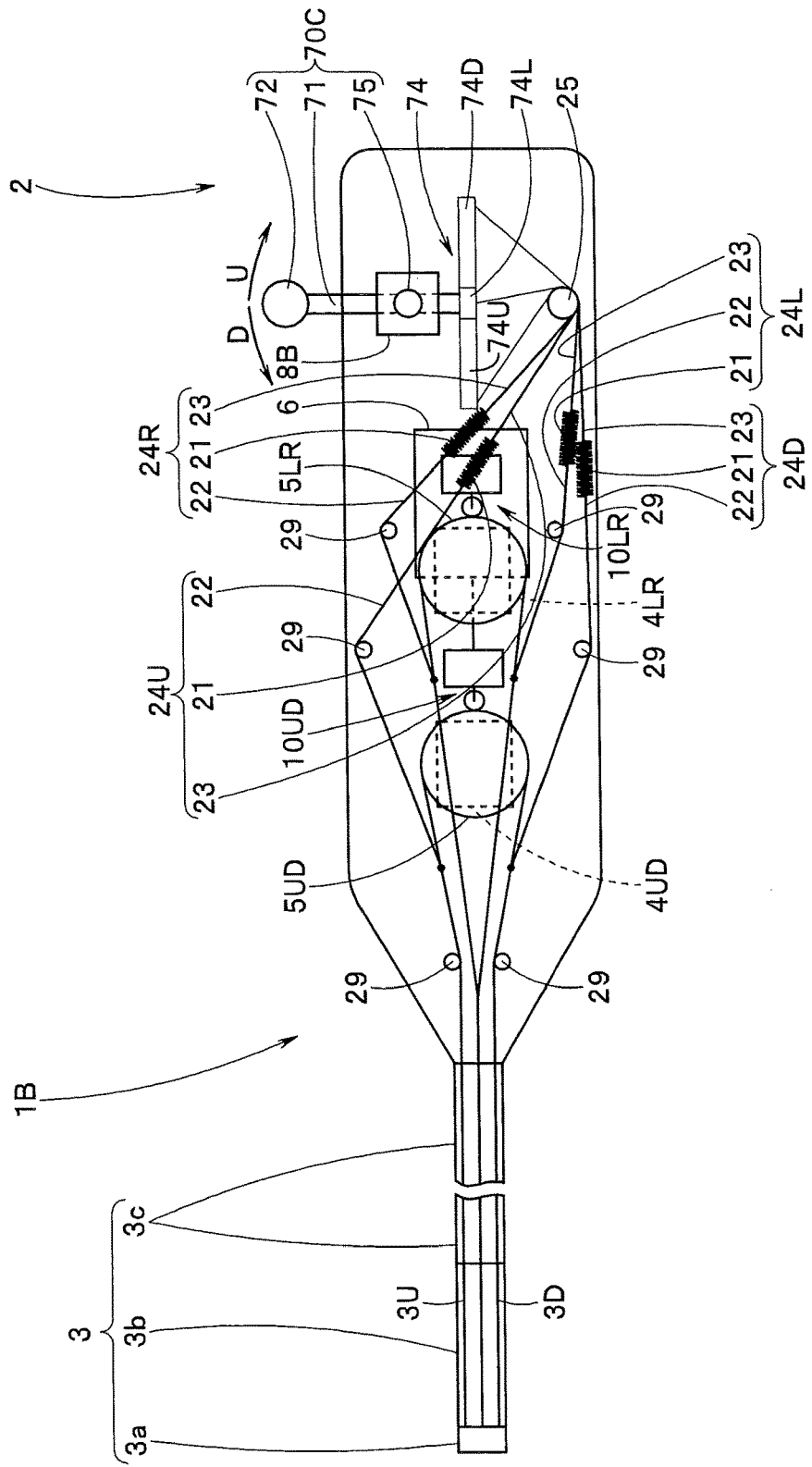

Also, as illustrated in FIGS. 9 to 10, a manipulator 70C including a shaft portion 71 with a frame shaft 74a of a cruciform frame body 74 joined thereto via a universal joint 75 may be provided. In the case of the manipulator 70C, the second joining wire 23 that provides the second end of the up transmission wire 24U is fixed to an end portion of an up frame 74U included in the frame body 74, the second joining wire 23 that provides the second end of the down transmission wire 24D is fixed to an end portion of a down frame 74D, the second joining wire 23 that provides the second end of the left transmission wire 24L is fixed to an end portion of a left frame 74L, and the second joining wire 23 that provides the second end of the right transmission wire 24R is fixed to an end portion of a right frame 74R.

In this configuration, the idlers 25 that make the respective transmission wires 24U, 24D, 24L and 24R be tightened with a predetermined tensile force are provided opposite to the shaft portion 71 across the frame body 74. In other words, the plurality of idlers 25 are aligned immediately below the frame body 74 in parallel to the left frame 74L and the right frame 74R perpendicular to a longitudinal axis of the operation portion 2.

The rest of the configuration is similar to that of the above-described embodiment, members that are the same as those of the above-described embodiment are provided with reference numerals that are the same as those of the above-described embodiment, and a description thereof will be omitted.

This configuration enables provision of operations and effects similar to those of the above-described embodiment.

Figure 11:
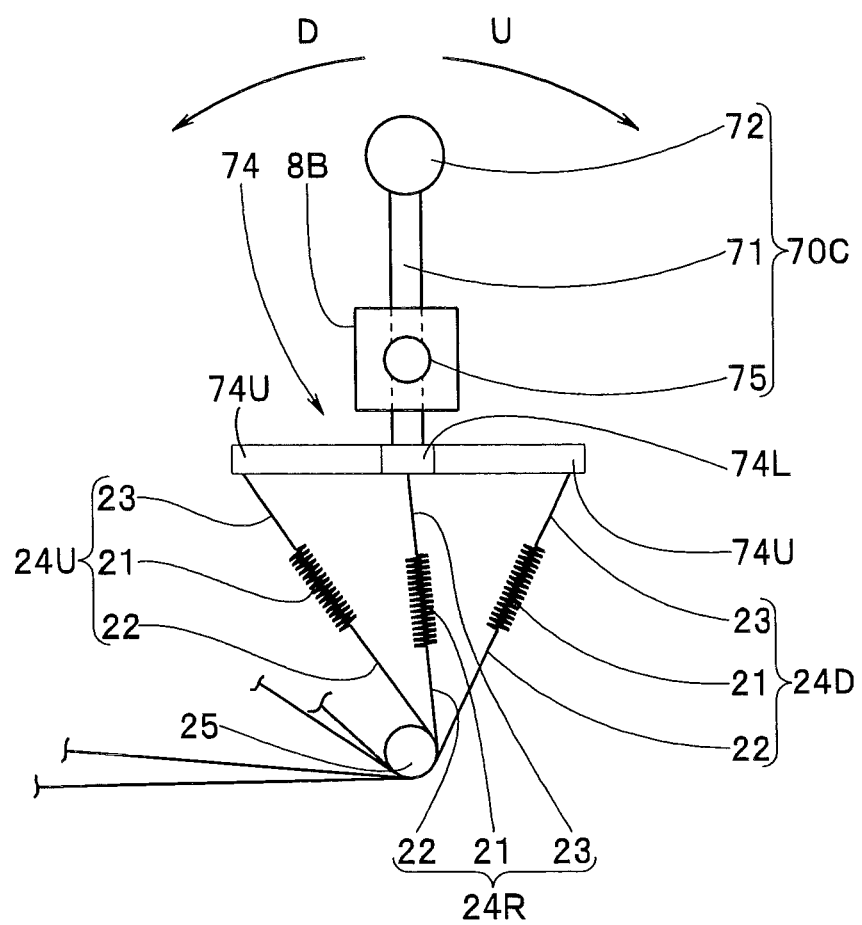
FIG. 11 relates to another modification of the second embodiment, and is a diagram illustrating a configuration in which springs for transmission wires are provided between a suspension frame and an idler.

In the above-described embodiment, a configuration in which the springs 21 included in the transmission wires 24U, 24D, 24L and 24R are arranged between the idlers 25 and the guide rollers 29 is indicated. However, the positions where the springs 21 are arranged are not limited to the aforementioned positions, and as illustrated in FIG. 11, the springs 21 of the respective transmission wires 24U, 24D, 24L and 24R may be provided between the frame body 74 and the idlers 25 immediately below the frame body 74.

Note that in a configuration in which the respective springs 21 are provided between the frame body 74 and the idlers 25, the respective springs 21 may directly be fixed to the up frame 74U, the down frame 74D, the left frame 74L and the right frame 74R.

According to this configuration, the transmission wires 24U, 24D, 24L and 24R can be formed by the respective first joining wires 22 and the springs 21.

Also, it is possible that: the transmission wires 24U, 24D, 24L and 24R are formed by the respective springs 21 and the respective second joining wires 23; and respective first ends of the springs 21 are joined to the up wire 3U, the down wire 3D, the left wire 3L and the right wire 3R.

Figure 12:
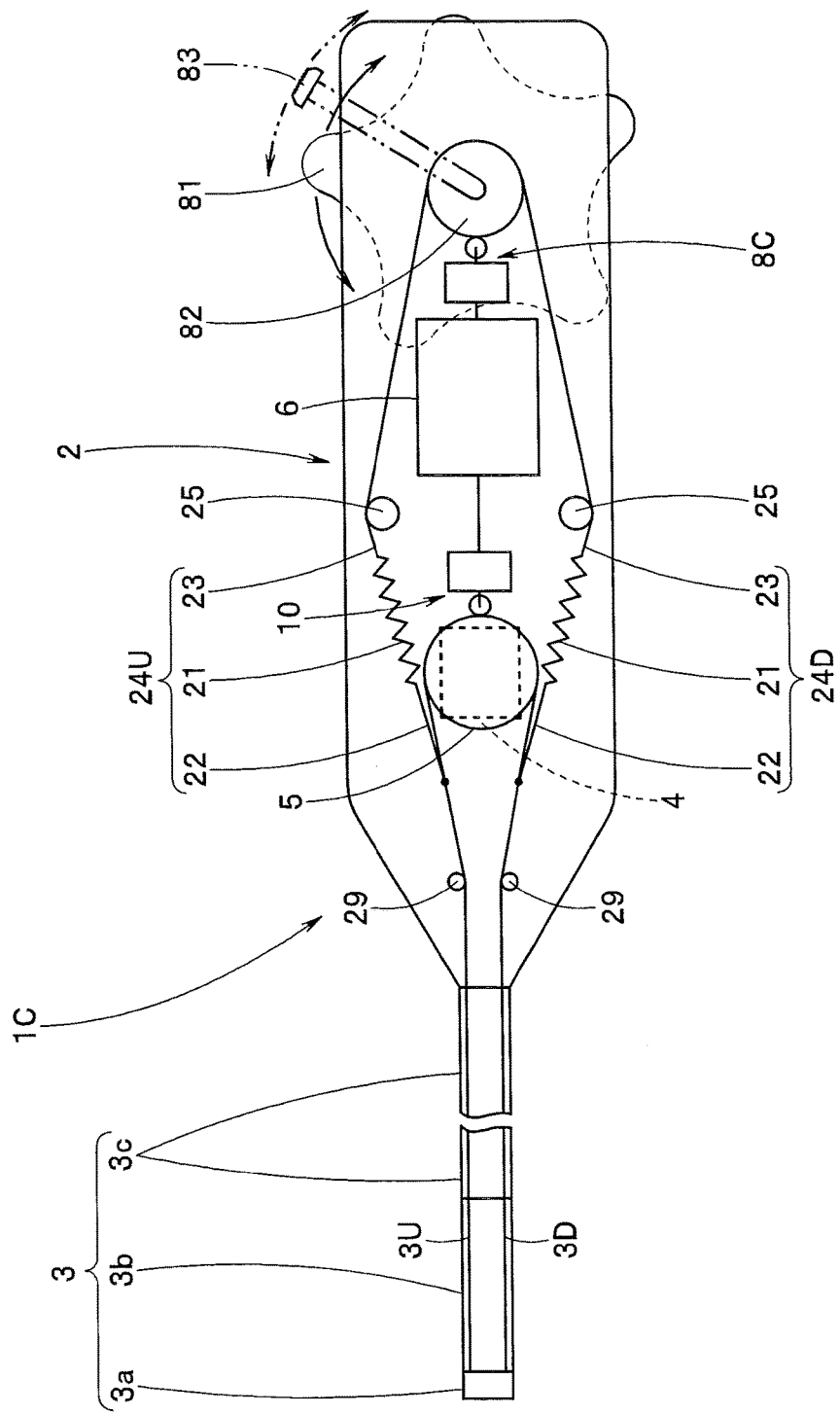
FIG. 12 is a diagram illustrating a configuration of a haptic section included in an motorized endoscope according to a modification of the first embodiment, the motorized endoscope allowing provision of an instruction to bend a bending portion that bends in two directions, i.e., upward and downward by operating a bending operation knob.

FIG. 12 is a diagram illustrating a configuration of an endoscope that allows provision of an instruction to bend a bending portion that bends in two directions, i.e., upward and downward by rotating an operation knob.

As illustrated in FIG. 12, a bending portion 3b of an endoscope 1C according to the present embodiment is configured to bend upward/downward as indicated in FIGS. 2 and 3. An operation portion 2 includes a bending operation knob 81 instead of the manipulator 70 illustrated in FIGS. 2 and 3 as a bending operation apparatus 7. In other words, the endoscope 1C is a modification of the first embodiment.

The endoscope 1C according to the present embodiment includes the bending operation knob 81 in the operation portion 2 as the bending operation apparatus 7. In the bending operation knob 81, a rotating shaft portion 82 is provided integrally and coaxially with the bending operation knob 81. The bending operation knob 81 is configured so that the bending operation knob 81 is pivotable about a center axis and can be rotated in two directions, i.e., clockwise and counterclockwise in FIG. 12.

An input instruction detecting section 8C is a rotation operation amount detection apparatus. The input instruction detecting section 8C detects a direction and an angle of rotation of the rotating shaft portion 82 as a rotation operation amount and outputs a result of the detection to the bending control section 6 as an operation input instruction signal.

In the present embodiment, a first joining wire 22 that provides a first end of an up transmission wire 24U is fixed at a predetermined position on the insertion portion 3 side of an up wire 3U relative to a pulley 5. A second joining wire 23 that provides a second end of the up transmission wire 24U is fixed at the predetermined position on the rotating shaft portion 82.

On the other hand, a first joining wire 22 that provides a first end of a down transmission wire 24D is fixed at a predetermined position on the insertion portion 3 side of a down wire 3D relative to the pulley 5. A second joining wire 23 that provides a second end of the down transmission wire 24D is fixed at a predetermined position on the rotating shaft portion 82.

The respective transmission wires 24U and 24D are arranged to run in a state in which the respective transmission wires 24U and 24D are tightened with a predetermined tensile force via respective idlers 25 when the bending portion 3b is in a straightened state. Here, each spring 21 is in a predetermined expanded state.

Note that the up wire 3U and the down wire 3D run in such a manner that the up wire 3U and the down wire 3D are guided to the pulley 5 via, e.g., guide rollers 29. The rest of the configuration is similar to that of the endoscope 1A illustrated in FIGS. 2 and 3, and members that are the same as those of the endoscope 1A are provided with reference numerals that are the same as those of the endoscope 1A and a description thereof will be omitted.

When a surgeon rotates the bending operation knob 81 clockwise in FIG. 12 to bend the straightened bending portion 3b upward, the up transmission wire 24U is pulled and the down transmission wire 24D is slackened with the rotation of the bending operation knob 81.

Also, with the rotation of the bending operation knob 81, an operation input instruction signal corresponding to an amount of the rotation is outputted from the input instruction detecting section 8C to the bending control section 6.

The bending control section 6 calculates a motor drive signal from the inputted operation input instruction signal and outputs the calculated motor drive signal to the motor 4.

The motor 4 is driven and controlled by the motor drive signal, and with the driving, the pulley 5 rotates clockwise. As a result, the up wire 3U is pulled by the rotation of the pulley 5 and the down wire 3D is slackened by the rotation of the pulley 5. As a result, the straightened bending portion 3b gradually bends upward. Here, the slackened down wire 3D is pulled in a direction opposite to that of the up wire 3U with the bending of the bending portion 3b.

In the present embodiment, a first movement distance of movement of the first end side of the up transmission wire 24U accompanying the up wire 3U is set to be shorter than a second movement distance of movement of the second end side of the up transmission wire 24U accompanying the rotation of the bending operation knob 81. As a result, during the bending operation, the up transmission wire 24U, which runs via an idler 25 described above, maintains the state of running with the predetermined tensile force as a result of the expanded spring 21 being expanded.

On the other hand, a third movement distance of movement of the first end side of the down transmission wire 24D accompanying the down wire 3D is set to be longer than a fourth movement distance of movement of the second end side of the down transmission wire 24D accompanying the rotation of the bending operation knob 81. As a result, during the bending operation, the down transmission wire 24D, which runs via an idler 25 described above, maintains the state of running with the predetermined tensile force as a result of the expanded spring 21 being further compressed.

Accordingly, as the surgeon increases the angle of rotation of the bending operation knob 81, the bending portion 3b continuously bends upward. Here, the spring 21 of the up transmission wire 24U continuously expands and the spring 21 of the down transmission wire 24D continuously compresses. As a result, the transmission wires 24U and 24D are maintained in the state of running with the predetermined tensile force.

During the bending operation, if the distal end portion 3a abuts against, e.g., a body wall and a reactive force applied to the bending portion 3b reaches a predetermined strength amount, the pulling of the up wire 3U is halted. As a result, the upward bending of the bending portion 3b is halted. Also, with the halt of the upward bending of the bending portion 3b, the pulling of the down wire 3D resulting from the bending of the bending portion 3b is also halted. Then, the continuous expansion of the spring 21 of the down transmission wire 24D is halted.

At this time, the rotation by the surgeon is continued. Accordingly, the spring 21 of the up transmission wire 24U is further expanded. On the other hand, the continuous compression of the spring 21 of the down transmission wire 24D is halted and the spring 21 is further expanded because of the continuation of the rotation. Then, a load that makes the rotating shaft portion 82 rotate counterclockwise is transmitted from the spring 21 of the down transmission wire 24D to the rotating shaft portion 82 via the corresponding second joining wire 23. As a result, a change occurs in operational feeling such as an increase in amount of rotation operation strength of a hand of the surgeon that is rotating the bending operation knob 81 clockwise. In other words, the surgeon can become aware of a trouble such as the distal end portion 3a of the bending portion 3b abutting against, e.g., a body wall during a bending operation.

Other operations and effects are similar to those of the above-described endoscope illustrated in FIGS. 2 and 3.

Note that in the above-described modification, the bending operation knob 81 is provided instead of the manipulator 70 as the bending operation apparatus 7. However, operations and effects similar to the above can also be provided if a bending operation lever 83, which is indicated by the alternate long and two short dashes lines in FIG. 12, is provided instead of the bending operation knob 81 and the rotating shaft portion 82 is rotated via the lever 83.

Also, operations and effects similar to the above can also be provided if the bending operation knob 81 and the bending operation lever 83 are rotated in a direction opposite to the above.

Figure 13:
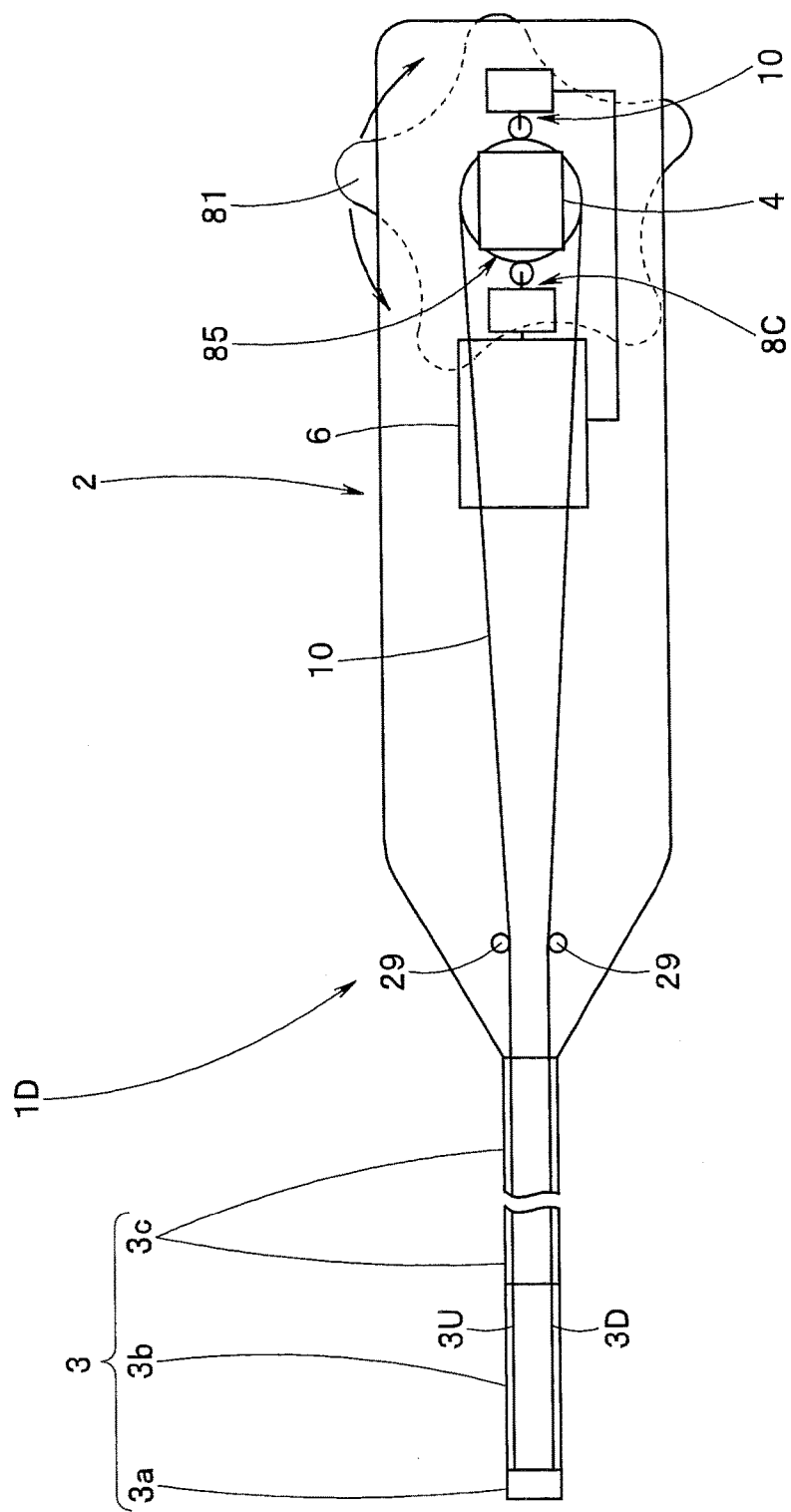
FIGS. 13 to 17 relate to another modification of the first embodiment and FIG. 13 relates to another configuration of the motorized endoscope that allows provision of an instruction to bend a bending portion that bends in two directions, e.g., upward and downward by operating a bending operation knob.

Another modification of the first embodiment will be described with reference to FIGS. 13 to 17. As illustrated in FIG. 13, in an endoscope 1D according to the present embodiment, a haptic section 85 is provided coaxially with a bending operation knob 81.

Figure 14:
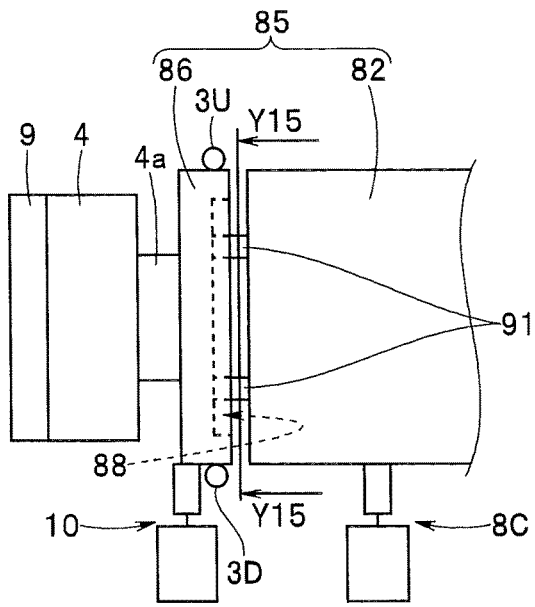
Figure 15:
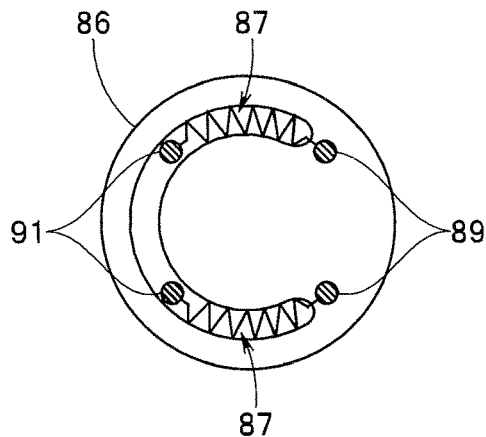

As illustrated in FIGS. 14 and 15, the haptic section 85 includes a pulley 86, a rotating shaft portion 82 and two hooked springs 87, which are combined to form a predetermined integrated shape. The pulley 86 and the rotating shaft portion 82 are configured to rotate clockwise/counterclockwise independently from each other.

Figure 16:
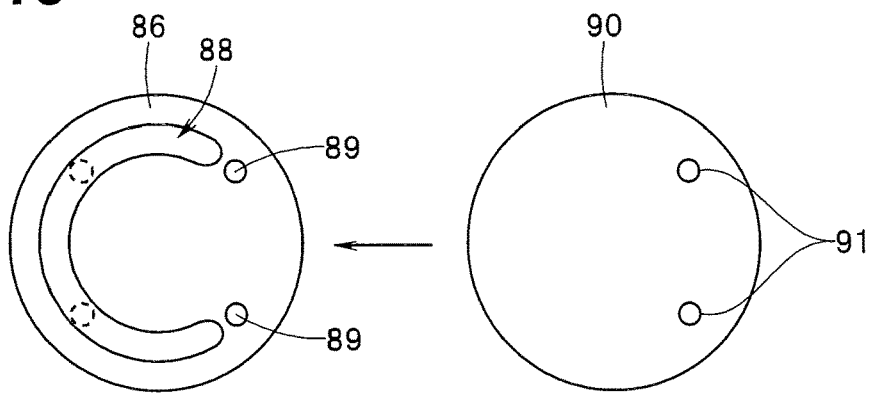

As illustrated in FIGS. 14 to 16, on one surface side of the pulley 86, one circumferential groove 88 having a predetermined shape is formed at a predetermined position. The circumferential groove 88 receives respective spring parts of the two hooked springs 87. Reference numeral 89 denotes a pair of pulley-side projection portions. The pulley-side projection portions 89 project to a predetermined height from the one surface side of the pulley 86. The pulley-side projection portions 89 are provided at respective predetermined positions relative to respective end portions of the circumferential groove 88. One hook of each hooked spring 87 is put on the relevant pulley-side projection portion 89.

On the other hand, a pair of shaft-side projection portions 91 are provided at respective predetermined positions in a distal end face 90 of the rotating shaft portion 82. When the pulley 86 and the rotating shaft portion 82 are combined, the pair of shaft-side projection portions 91 are slidably arranged inside the circumferential groove 88. The other hook of each hooked spring 87 is put on the relevant shaft-side projection portion 91.

Note that in the present embodiment, each hooked spring 87 is an elastic portion, and when the bending portion 3b is in a straightened state, the spring part included in each hooked spring 87 is held in an initial state in which the hooked spring 87 neither expands nor compresses.

The rest of the configuration is similar to the configuration of the endoscope 1C illustrated in FIG. 12, and members that are the same as those of the endoscope 1C are provided with reference numerals that are the same as those of the endoscope 1C and a description thereof will be omitted.

Figure 17:
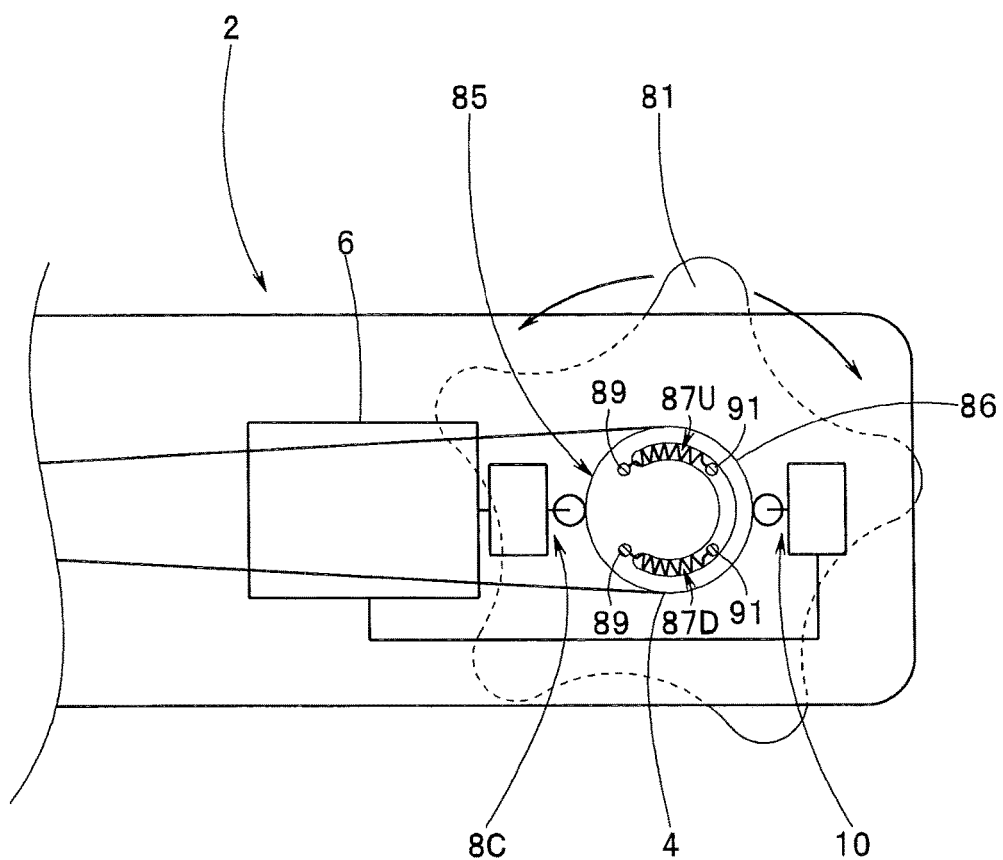

As illustrated in FIG. 17, when a surgeon rotates the bending operation knob 81 clockwise to bend the bending portion 3b upward, the shaft-side projection portions 91 rotate clockwise with the rotation of the bending operation knob 81.

Also, with the rotation of the bending operation knob 81, an operation input instruction signal corresponding to an amount of the rotation is outputted from an input instruction detecting section 8C to a bending control section 6.

The bending control section 6 calculates a motor drive signal from the inputted operation input instruction signal, and outputs the calculated motor drive signal to a motor 4.

The motor 4 is driven and controlled by the motor drive signal, and with the driving, the pulley 86 is also rotated clockwise. As a result, an up wire 3U is pulled by the rotation of the pulley 5 and a down wire 3D is slackened by the rotation of the pulley 5. Also, with the rotation of the pulley 86, the pulley-side projection portions 89 also rotate clockwise. Note that as the bending portion 3b gradually bends upward, the slackened down wire 3D is pulled in a direction opposite to that of the up wire 3U with the bending.

In the present embodiment, a first movement distance of movement of the pulley-side projection portions 89 accompanying the rotation of the pulley 86 is set to be longer than a second movement distance of movement of the shaft-side projection portions 91 accompanying the rotation of the bending operation knob 81. As a result, during the bending operation, an up spring 87U is compressed and a down spring 87D is pulled and expanded by the respective pulley-side projection portions 89 that move with the rotation of the pulley 86. Thus, the bending operation knob 81 is smoothly rotated without receiving a biasing force from the springs 87U and 87D.

Then, when the surgeon rotates the bending operation knob 81 to bend the bending portion 3b, the bending portion 3b continuously bends upward. Here, the up spring 87U is continuously compressed and the down spring 87D is continuously expanded.

During this bending operation, if the distal end portion 3a abuts against, e.g., a body wall and a reactive force applied to the bending portion 3b reaches a predetermined strength amount, the rotation of the pulley 86 is halted. As a result, the pulling of the up wire 3U is halted and the upward bending of the bending portion 3b is thereby halted.

Then, the up spring 87U is released from the force of continuously compressing up spring 87U. On the other hand, the down spring 87D is released from the force of continuously expanding the down spring 87D. As a result, a force that makes the rotating shaft portion 82 rotate reversely exerts by a biasing force of the up spring 87U and a biasing force of the down spring 87D. In other words, a change in operational feeling occurs as a result of an increase in amount of strength for rotating the bending operation knob 81 operated by the surgeon. As a result, the surgeon can become aware of a trouble such as the distal end portion 3a of the bending portion 3b abutting against, e.g., a body wall during a bending operation.

As described above, with the endoscope 1D, the bending wire 3U or 3D is not directly pulled, but the bending operation knob 81 is rotated to drive the motor 4 to rotate the pulley 5, enabling the bending portion 3b to bend in any direction of upward, downward, leftward and rightward.

Also, a configuration in which the pulley 5 and the rotating shaft portion 82 of the bending operation knob 81 are integrally combined with two springs 87 arranged therebetween is provided. Consequently, in a bending operation state in which the bending operation knob 81 is rotated to pull either of the bending wires 3U and 3D by a drive force of the motor 4, if the distal end portion 3a abuts against, e.g., a body wall, the rotation of the pulley 5 is halted and a load is transmitted from the springs 87U and 87D included in the haptic section 85 to the rotating shaft portion 82. As a result, during a bending operation, the surgeon can become aware of a trouble such as the distal end portion 3a of the bending portion 3b abutting against, e.g., a body wall.

Note that other operations and effects are similar to those of the endoscope illustrated in FIGS. 2 and 3 and the endoscope illustrated in FIG. 12 described above. Also, operations and effects similar to the above can be provided also when the bending operation knob 81 is rotated in a direction opposite to the above.

Also, in the above embodiments, an endoscope is used as a medical device; however, the medical devices are not limited to endoscopes, and may be, for example, overtubes including a bending portion through which an endoscope is inserted or treatment instruments including a bending portion.

A third embodiment of the present invention will be described below with reference to FIGS. 18 to 20D.

Figure 18:
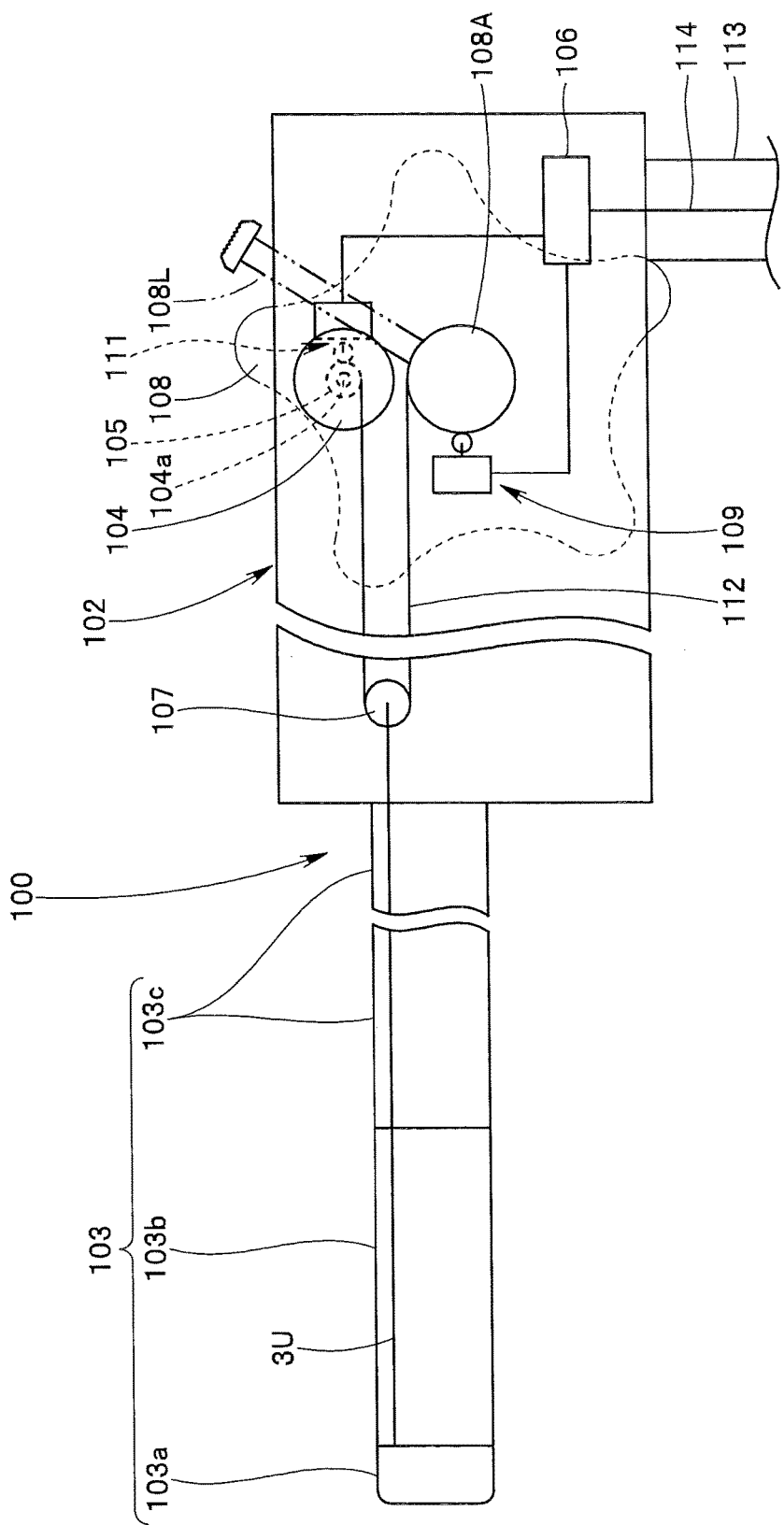
Figure 19:
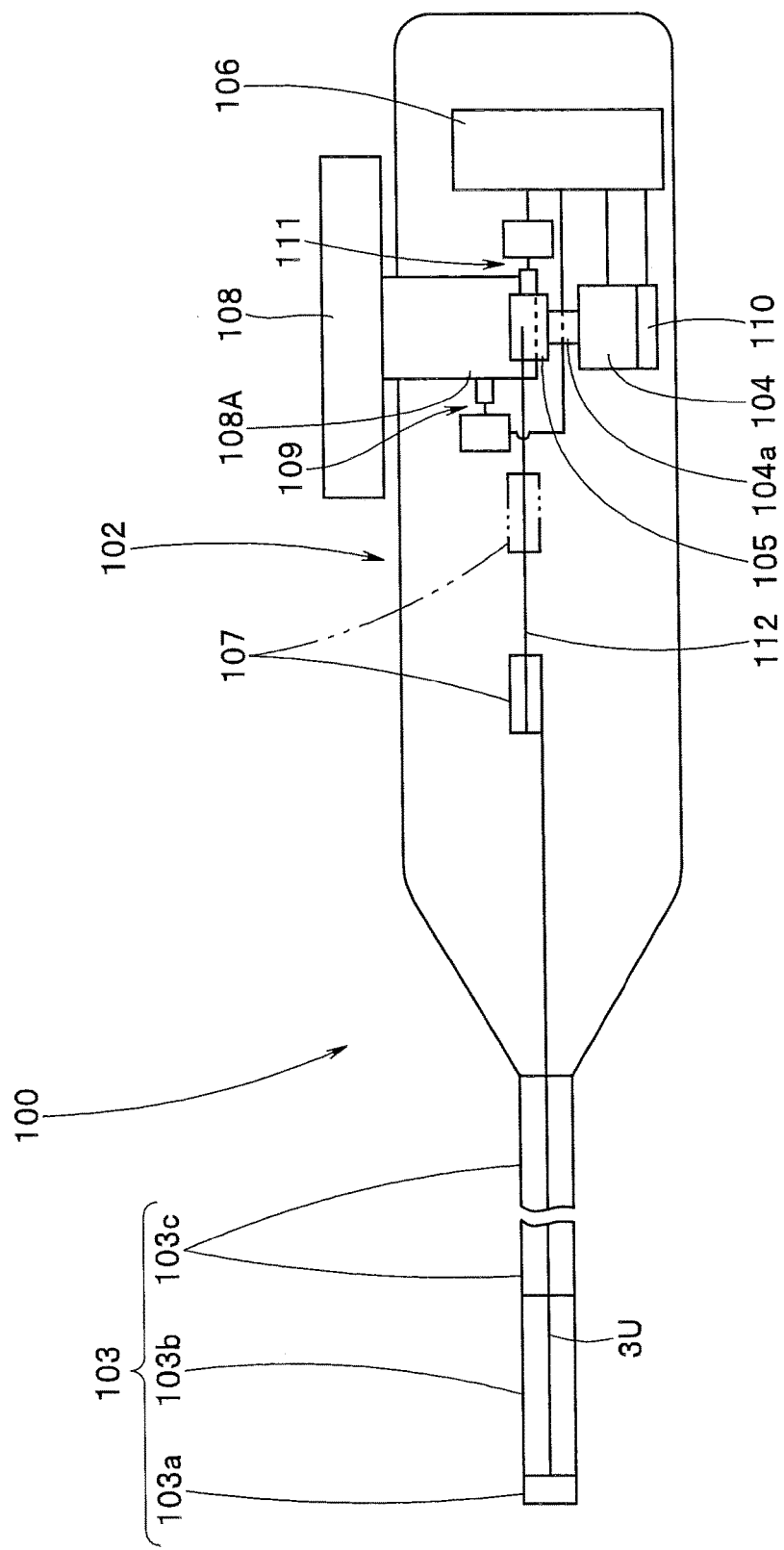

The endoscope illustrated in FIGS. 18 and 19 is a motorized bending endoscope 100. The motorized bending endoscope 100 includes, for example, a motor 104 that drives a bending portion 103b of an insertion portion 103 to bend inside an operation portion 102.

In the present embodiment, the motor 104 is, for example, a pulse motor. A pulley 105 is fixed integrally to a drive shaft 104a of the motor 104. The pulley 105 is rotated with driving of the motor 104. The motor 104 is driven and controlled by a bending control section 106. The pulley 105, which is integrated with the motor 104 and the drive shaft 104a, is a bending drive section.

The insertion portion 103 includes a rigid distal end portion 103a, a bendable bending portion 103b and a flexible tube portion 103c having a long length and flexibility, which are continuously provided in this order from the distal end side. In a non-illustrated distal end face of the distal end portion 103a, i.e., an observation window, an illumination window and a treatment instrument opening are provided. An image pickup apparatus including an image pickup device such as a CCD or a C-MOS is incorporated in the distal end portion 103a.

The bending portion 103b is configured so as to bend in one direction, two directions or four directions by, for example, pivotally joining a plurality of non-illustrated bending pieces to one another. The bending portion 103b illustrated in FIG. 18 is configured to bend, for example, upward. In the present embodiment, one end of an up wire 3U is fixed at a predetermined position on a distalmost end bending piece (not illustrated). The other end of the up wire 3U is fixed at a predetermined position on a moving pulley 107, which is a later-described winding portion.

The operation portion 102 includes, for example, a grasping portion (not illustrated) and an operation portion body (not illustrated), and at the operation portion body, a bending operation knob 108, which is a bending operation apparatus, is provided.

Inside the operation portion 102, a shaft portion 108A of the bending operation knob 108, a later-described input instruction detecting section 109, an encoder 110 and a potentiometer 111 are provided in addition to the motor 104, the pulley 105, the bending control section 106 and the moving pulley 107.

The bending operation knob 108 is an apparatus to be operated to provide an instruction to bend the bending portion 103b. The bending operation knob 108 is rotated by a surgeon. When a surgeon rotates the bending operation knob 108 to bend the bending portion 103b, the shaft portion 108A rotates integrally with the bending operation knob 108. Note that a configuration in which a bending operation lever 108L indicated by the alternate long and two short dashes lines is provided integrally with the shaft portion 108A instead of the bending operation knob 108 may be employed.

The other end of the up wire 3U extending from the insertion portion 103 is fixed to the moving pulley 107 arranged inside the operation portion 102. A portion partway of a bending wire moving operation wire (hereinafter abbreviated as "operation wire") 112, which is a second pulling member, is wound around the moving pulley 107.

One end of the operation wire 112 is fixed at a predetermined position on the shaft portion 108A. The other end of the operation wire 112 is fixed at a predetermined position on the pulley 105. The shaft portion 108A and the pulley 105 are provided opposite to the one end of the up wire 3U across the moving pulley 107. A running route of the operation wire 112 with the one end fixed to the shaft portion 108A is looped back by the moving pulley 107 and the other end of the operation wire 112 reaches the pulley 105.

With this configuration, the bending operation knob 108 is rotated clockwise in FIG. 18 to rotate the shaft portion 108A in the same direction, enabling the one end side of the operation wire 112 to be wound around the shaft portion 108A. On the other hand, the pulley 105 is rotated counterclockwise in FIG. 18 by driving of the motor 104, enabling the other end side of the operation wire 112 to be wound around the pulley 105.

The input instruction detecting section 109 detects an amount of rotation of the shaft portion 108A that rotates with rotation of the bending operation knob 108. The input instruction detecting section 109 outputs a detected result of the detection to the bending control section 106 as an operation input instruction signal. The encoder 110 detects a rotational position of the motor 104 and outputs the rotational position to the bending control section 106 as motor position information. The potentiometer 111 detects a rotational position of the pulley 105 and outputs the rotational position to the bending control section 106 as pulley position information.

In other words, the operation input instruction signal, the motor position information and the pulley position information are inputted to the bending control section 106. The bending control section 106 performs arithmetic processing based on the operation input instruction signal, the motor position information and the pulley position information to calculate a motor drive signal, and outputs the drive signal to the motor 104.

The motor 104 is driven and controlled by the motor drive signal. As a result, the pulley 105 is rotated by the motor 104. The pulley 105 is set to wind up an amount of the other end side of the operation wire 112, the amount being the same as that of the one end side of the operation wire 112 wound up by the shaft portion 108A that rotates with rotation of the bending operation knob 108.

In this configuration, the moving pulley 107 is moved in a longitudinal direction of the operation portion 102 as a result of the wind-up of the one end side of the operation wire 112 and the wind-up of the other end side of the operation wire 112, and thereby pulls the up wire 3U. An amount of movement of the moving pulley 107 in that axis direction is set to be the same as an amount of wind-up of the one end side of the operation wire 112 wound up by the shaft portion 108A and an amount of the other end side of the operation wire 112 wound up by the pulley 105.

Then, an amount of strength of operation of the bending operation knob 108 when the moving pulley 107 is moved by the one end side and the other end side of the operation wire 112 is half an amount of strength for pulling the up wire 3U. Also, the drive force of the motor 104 is also half of the pulling strength amount.

Note that reference numeral 113 denotes a universal cord. A connector (not illustrated) is provided at an end portion of the universal cord 113 extending from the operation portion 102. A light source apparatus (not illustrated), which is an external apparatus, is detachably connected to the connector. Reference numeral 114 denotes an electric wire inserted through the universal cord. The electric wire 114 supplies power to, e.g., the motor 104 via the bending control section 106.

In the above-described embodiment, it is assumed that the bending control section 106 is provided inside the operation portion 102. However, e.g., a configuration in which the bending control section 106 is provided inside the light source apparatus or a configuration in which the bending control section 106 is provided inside a video processor (not illustrated), which is an apparatus external to the motorized bending endoscope 100, may be employed. In this configuration, a signal wire is inserted through the universal cord to output a motor drive signal calculated by the bending control section 106 to the motor 104 via the signal wire.

An operation of the motorized bending endoscope 1 will be described with reference to FIGS. 20A to 20D.

Figure 20A:
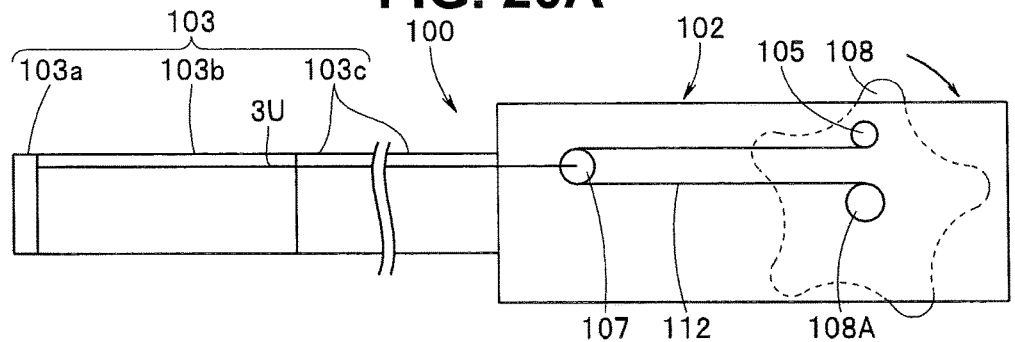
FIG. 20A is a diagram illustrating a bending operation start state where the bending portion included in the insertion portion is straightened.

In order to make the straightened bending portion 103b illustrated in FIG. 20A bend, a surgeon rotates the bending operation knob 108 clockwise as indicated by an arrow. Then, the shaft portion 108A rotates with the rotation of the bending operation knob 108, and the one end side of the operation wire 112 is wound up by the shaft portion 108A. As a result, the moving pulley 107 starts moving.

At this time, the surgeon rotates the bending operation knob 108 to move the moving pulley 107 without directly pulling the up wire 3U. Thus, an amount of operation strength for the surgeon to start operating the bending operation knob 108 is half a pulling force for directly pulling the up wire 3U by rotating the bending operation knob 108.

On the other hand, with the rotation of the shaft portion 108A, an operation input instruction signal corresponding to an amount of the rotation is outputted from the input instruction detecting section 109 to the bending control section 106. The bending control section 106 calculates a motor drive signal from the inputted operation input instruction signal, and outputs the calculated motor drive signal to the motor 104. The motor 104 is driven and controlled by the motor drive signal. As a result, with the driving of the motor 104, the pulley 105 rotates counterclockwise, whereby wind-up of the other end side of the operation wire 112 is started.

Figure 20B:
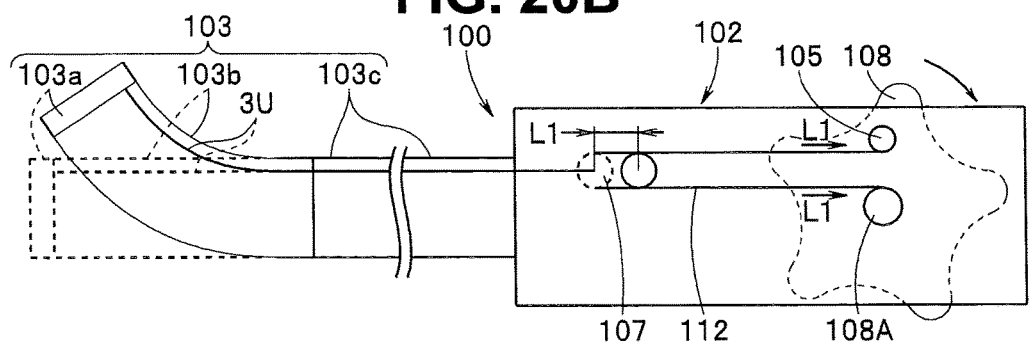
FIG. 20B is a diagram illustrating a relationship among a first pulling member, a winding portion and a second pulling member during a bending operation of the bending portion included in the insertion portion.

At this time, as illustrated in FIG. 20B, the moving pulley 107 pulls the up wire 3U by a distance L1 as a result of, for example, the one end side of the operation wire 112 being wound up by the distance L1 by the shaft portion 108A and the other end side of the operation wire 112 being wound up by the distance L1 by the pulley 105. As a result, the bending portion 103b bends upward.

In this bending operation state, the moving pulley 107 is moved by the wind-up of the operation wire 112 by the shaft portion 108A and the wind-up of the operation wire 112 by the pulley 105. Accordingly, the surgeon that rotates the bending operation knob 108 can make the bending portion 103b bend while operating the bending operation knob 108 with an operation strength amount that is half that for directly pulling the up wire 3U.

Here, if the surgeon continuously rotates the bending operation knob 108, the one end side of the operation wire 112 is further wound up around the shaft portion 108A and the other end side of the operation wire 112 is further wound up around the pulley 105. As a result, the up wire 3U is further pulled by the moving pulley 107, whereby an angle of upward bending of the bending portion 103b increases.

Figure 20C:
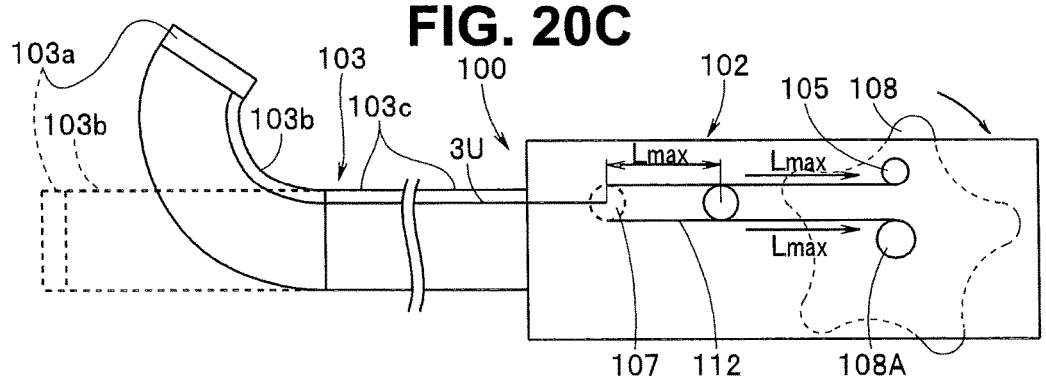
FIG. 20C is a diagram illustrating a relationship among the first pulling member, the winding portion and the second pulling member where the bending portion included in the insertion portion bends maximally.

Then, as a result of the bending operation knob 108 being maximally rotated, as illustrated in FIG. 20C, the one end side of the operation wire 112 is moved by a distance Lmax and the other end side is moved by the distance Lmax. As a result, the up wire 3U is also pulled by the distance Lmax as a result of the movement of the moving pulley 107, whereby the bending portion 103b is bent maximally.

Figure 20D:
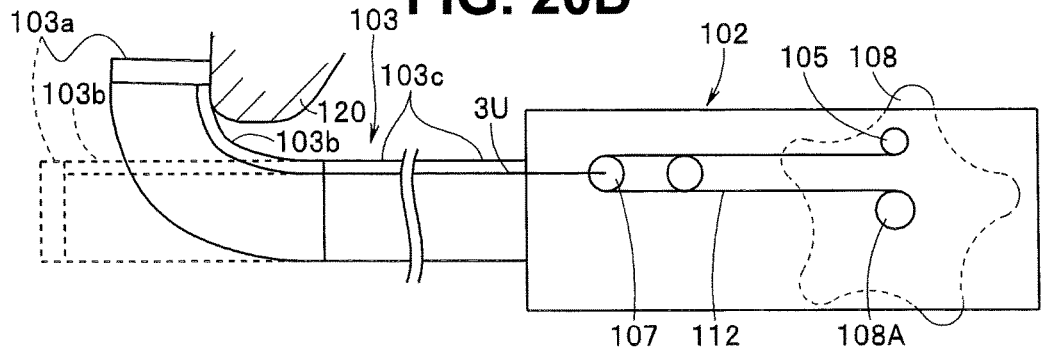

During a bending operation in which the surgeon rotates the bending operation knob 108 to bend the bending portion 103*b*, for example, as illustrated in FIG. 20D, e.g., the distal end portion 103*a* of the insertion portion 103 may abut against, e.g., a body wall 120. As a result of, e.g., the distal end portion 103*a* abutting against the body wall 120, the bending portion 103*b* including the distal end portion 103*a* is prevented by the body wall 120 from further bending. In other words, the rotation of the bending operation knob 108 makes the pulling of the up wire 3U difficult.

In the motorized bending endoscope 100 according to the present embodiment, the operation wire 112 extends from the shaft portion 108A of the bending operation knob 108. The operation wire 112 is connected to the up wire 3U via the moving pulley 107. As a result, during a bending operation in which the bending operation knob 108 is rotated, if the distal end portion 103*a* abuts against the body wall 120, simultaneously with the abutment, an amount of rotation operation strength of a hand of the surgeon that is rotating the bending operation knob 108 increases. Accordingly, the surgeon can become aware of a trouble such as the distal end portion 103*a* of the bending portion 103*b* abutting against, e.g., the body wall 120 during a bending operation as a result of occurrence of a change in operational feeling for operating the bending operation knob 108.

As described above, in the motorized bending endoscope 100, the up wire 3U, the operation wire 112 and the moving pulley 107 are provided. Then, one end of the operation wire 112 is fixed to the shaft portion 108A of the bending operation knob 108 and the other end of the wire 112 is fixed to the pulley 105 to be rotated by the motor 104. In addition, an intermediate portion of the wire is wound on the moving pulley 107.

As a result, the bending portion 103*b* and the bending operation knob 108 of the motorized bending endoscope 100 are connected via the up wire 3U, the moving pulley 107 and the operation wire 112.

Accordingly, in the motorized bending endoscope 100, during a bending operation by a surgeon, if the distal end portion 103*a* abuts against the body wall 120, a change in operational feeling is transmitted to a hand of the surgeon that is operating the bending operation knob 108. As a result, the surgeon can reliably determine that a trouble has occurred during the bending operation of the bending portion 103*b*.

Also, a surgeon can pull the up wire 3U by moving the moving pulley 107 in the longitudinal direction of the operation portion without directly pulling the up wire 3U from a point of time immediately after a start of rotation of the bending operation knob 108 until the bending portion 103*b* is bent maximally, enabling reduction in amount of rotation operation strength provided by the surgeon.

In addition, the amount of wind-up of the other end side of the operation wire by the pulley 105 to be rotated by the motor 104 is set to be the same as the amount of wind-up of the one end side of the operation wire by the shaft portion 108A. As a result, a bending operation of the bending portion 103*b* can be performed while the motor 104 is downsized.

Note that upon counterclockwise rotation of the bending operation knob 108, the bending portion 103*b* bent as a result of the bending operation knob 108 being rotated deforms to restore to a straightened state by an elastic repellent force the bending portion 103*b* has.

Also, in the above-described embodiment, the bending portion 103*b* is configured to bend in one direction, i.e., upward. However, the bending portion 103*b* may be configured to bend in two directions, i.e., upward and downward. In such case, e.g., a down wire, an operation wire, a moving pulley 107 and a motor 104 equipped with a pulley 105 is provided for downward bending.

Furthermore, in the above-described embodiment, the amount of wind-up of the other end side of the operation wire by the pulley 105 to be rotated by the motor 104 is set to be the same as the amount of wind-up of the one end side of the operation wire by the shaft portion 108A. However, for example, the amount of wind-up of the other end side of the operation wire by the pulley 105 may be set to be larger than the amount of wind-up of the one end side of the operation wire by the shaft portion 108A to reduce a burden on a surgeon when the bending portion 103*b* is maximally bent.

Also, a hook on the one end side of a hooked spring may be put on the moving pulley 107 to set an initial position of the moving pulley 107 when the bending portion 103*b* is in a straightened state. In addition, a restriction portion that restricts smooth movement of the moving pulley 107 in the longitudinal direction of the operation portion may be provided in the operation portion.

[Appendices]

As described in detail above, the third embodiment of the present invention can provide a configuration as follows.

(1) An insertion apparatus comprising:

a first pulling member including an end fixed to a bending portion provided in an insertion portion;

a bending drive section that outputs a drive force for bending the bending portion;

a bending operation apparatus for inputting an operation instruction to bend the bending portion; a second pulling member including one end fixed to the bending operation apparatus and another end fixed to the bending drive section;

a winding portion arranged in such a manner that the winding portion can advance/retract in a longitudinal direction of the operation portion, the winding portion allowing a portion partway of the second pulling member to be wound thereon, another end of the first pulling member being fixed to the winding portion;

an input instruction detecting section that detects a bending operation instruction inputted via the bending operation apparatus and outputs an operation input instruction signal; and a control section that based on the operation input instruction signal outputted from the input instruction detecting section, calculates a drive signal for pulling the first pulling member via the second pulling member in order to bend the bending portion and outputs the drive signal to the bending drive section.

(2) The insertion apparatus according to appendix 1, wherein a one end-side movement amount of movement of one end side of the second pulling member in response to the bending instruction from the bending operation apparatus is the same as an amount of movement of another end side of the second pulling member by the bending drive section driven by the drive signal outputted from the control section.

(3) The insertion apparatus according to appendix 1, wherein a one end side movement amount of movement of one end side of the second pulling member in response to the bending instruction from the bending operation apparatus is different from an amount of movement of another end side of the second pulling member by the bending drive section driven by the drive signal outputted from the control section.

(4) The insertion apparatus according to appendix 1, wherein the winding portion is a moving pulley.

FIG. 6 of Japanese Patent Application Laid-Open Publication No. 08-224241 indicates an endoscope including a bending tube that bends upward, downward, leftward and rightward by operating a joystick, which is a manipulator, provided in a casing. With this endoscope, upon the joystick being operated by a surgeon, a controller converts the operation into upward downward rightward and/or leftward bending angles to drive an upward/downward bending driving actuator and/or a leftward/rightward bending driving actuator, whereby wires are pulled or slackened and the bending portion thereby bends. In the endoscope with this configuration, a surgeon is released from work of directly pulling the wires and can easily perform an operation to bend the bending portion with a single finger.

Embodiments of the present appendices will be described below with reference to the drawings.

A first embodiment of the present appendices will be described with reference to FIGS. 21 to 26C.

Figure 21:
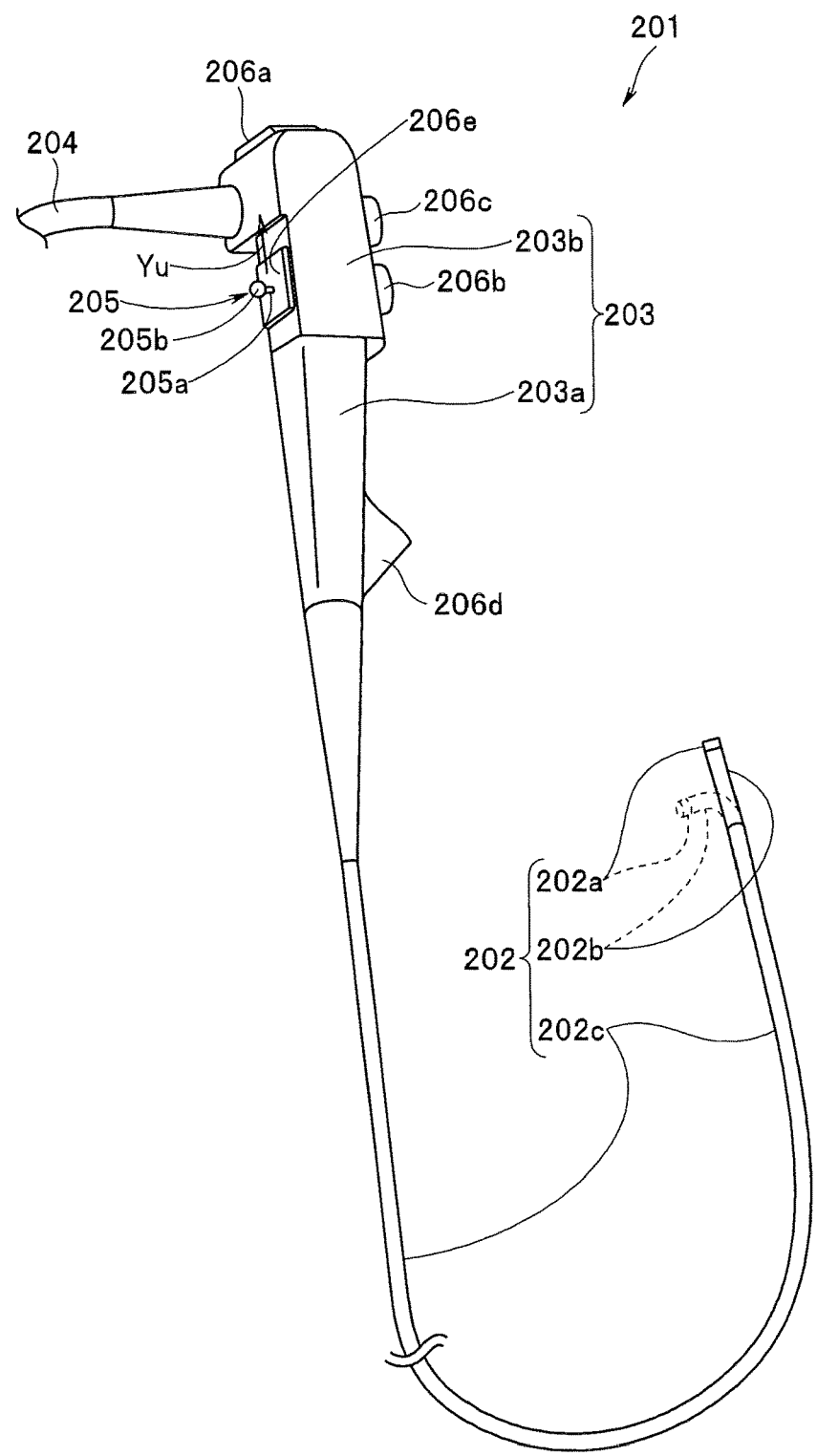

An endoscope 201 according to the present embodiment, which is illustrated in FIG. 21, includes an elongated insertion portion 202, an operation portion 203 provided to be continuous with a proximal end of the insertion portion 202, and a universal cord 204 extending from a side portion of the operation portion 203.

The insertion portion 202 includes a distal end portion 202a, a bending portion 202b and a flexible tube portion 202c, which are continuously provided in this order from the distal end side. The flexible tube portion 202c has flexibility and a long length. The bending portion 202b is configured to bend, for example, in four directions, i.e., upward, downward, leftward and rightward.

Note that it is assumed that the bending portion 202b of the present embodiment bends in four directions, i.e., upward, downward, leftward and rightward. However, the bending portion 202b may bend, for example, in two directions, i.e., upward and downward only or in one direction, i.e., upward only.

The operation portion 203 includes a grasping portion 203a provided to be continuous with the insertion portion 202, and an operation portion body 203b provided to be continuous with the grasping portion 203a. A rod-like manipulator 205 is provided on the distal end side of the operation portion body 203b.

The manipulator 205 is a bending operation apparatus. The manipulator 205 enables provision of an operation instruction to bend the bending portion 202b by a desired angle in a desired direction, by tilting the manipulator 205 to change a direction and an angle of tilting of the manipulator 205. The manipulator 205 projects from an opening (not illustrated) provided in a surface of the operation portion body 203b, for example, perpendicularly to a longitudinal direction of the operation portion 203. The bending portion 202b is configured so that, upon the manipulator 205 being tilted, for example, in the arrow Yu direction, the bending portion 202b is changed from a straightened state indicated by a solid line to a bent state indicated by a dashed line with the tilting.

At a sheath of the operation portion body 203b, for example, a switch 206a for giving instructions to perform various image pickup operations of an image pickup apparatus (not illustrated), an air/water feeding button 206b and a suction button 206c are provided at respective predetermined positions in addition to the manipulator 205.

Also, at a sheath of the grasping portion 203a, a channel insertion port 206d that is in communication with a treatment instrument channel (not illustrated) is provided. Reference numeral 206e denotes a cover member. The cover member 206e occludes the opening in a water-tight manner and in close contact with a shaft portion 205a of the manipulator 205. Also, the cover member 206e holds the manipulator 205 in a tiltable manner. Reference numeral 205b denotes a finger rest portion of the manipulator 205, which has, for example, a spherical shape.

Figure 22:
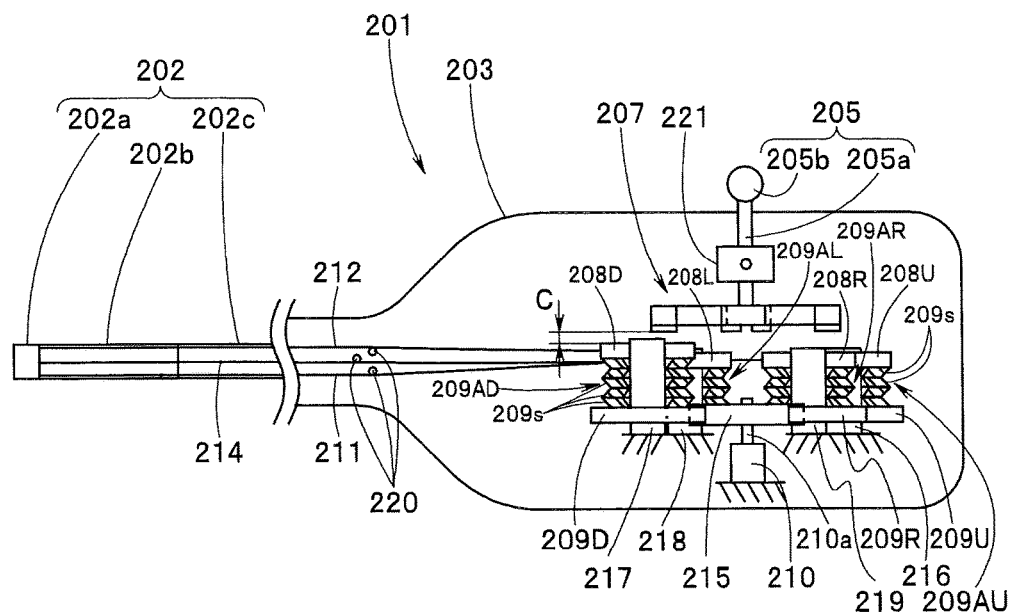
Figure 23:
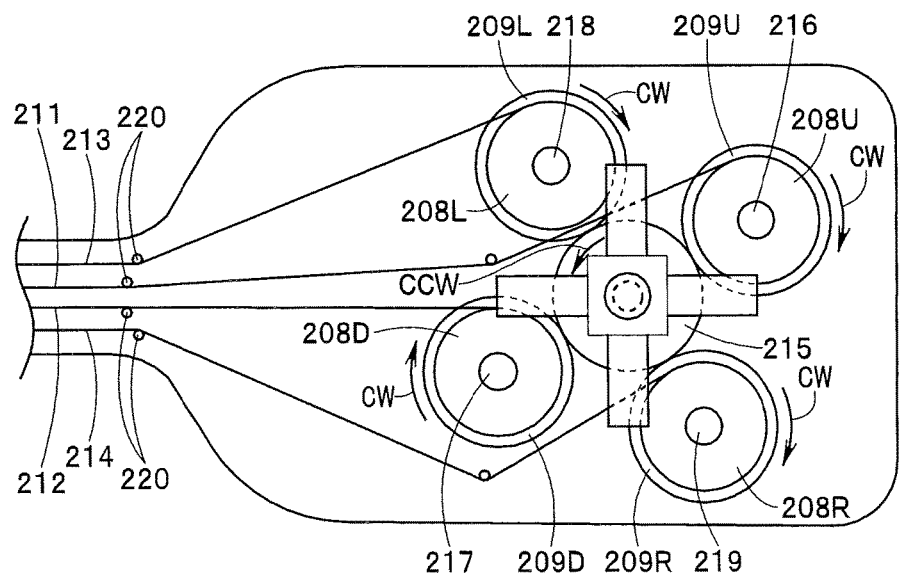
Figure 24:
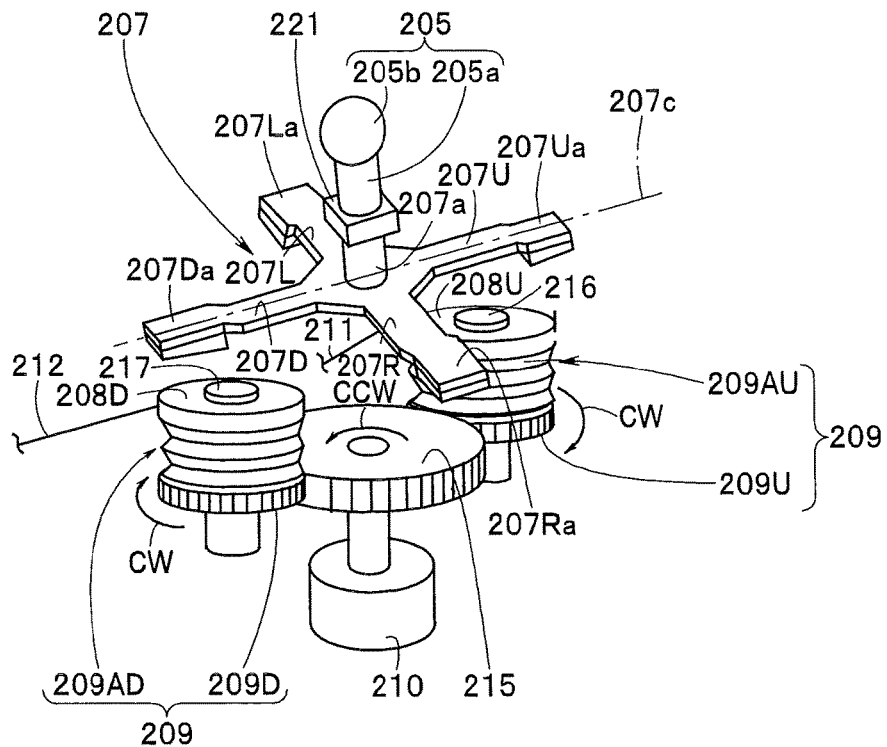

As illustrated in FIGS. 22 to 24, inside the operation portion 203, the shaft portion 205a of the manipulator 205, a suspension frame 207, disc-like pulleys 208U, 208D, 208L and 208R, which are rotating bodies, drive force transmission sections 209, a motor 210, and bending wires 211, 212, 213 and 214, which are pulling members, are mainly provided.

The bending wires 211, 212, 213 and 214, which are four wires corresponding to four bending directions of the bending portion 202b, are an up bending wire 211, a down bending wire 212, a left bending wire 213 and a right bending wire 214.

One end of each of the bending wires 211, 212, 213 and 214 is fixed at a predetermined position on the distal end side of the bending portion 202b. The other end of the up bending wire 211 is fixed to the up pulley 208U, the other end of the down bending wire 212 is fixed to the down pulley 208D, the other end of the left bending wire 213 is fixed to the left pulley 208L, and the other end of the right bending wire 214 is fixed to the right pulley 208R.

The respective bending wires 211, 212, 213 and 214 are introduced to the inside of the operation portion 203, and then respective running routes of the bending wires 211, 212, 213 and 214 are changed by a plurality of guide rollers 220 and the bending wires 211, 212, 213 and 214 are tightened with a predetermined tensile force.

A drive gear 215 is fixed to a motor shaft 210a of the motor 210. The configuration is formed so that rotation of the drive gear 215 is transmitted to the respective pulley 208U, 208D, 208L and 208R via the respective drive force transmission sections 209. Each drive force transmission section 209 includes a combination of a driven gear 209U, 209D, 209L or 209R and a force transmission adjustment section 209AU, 209AD, 209AL or 209AR. In the present embodiment, the motor 210, the drive gear 215 and the driven gears 209U, 209D, 209L and 209R provide a drive section.

The force transmission adjustment sections 209AU, 209AD, 209AL and 209AR are arranged between the driven gears 209U, 209D, 209L and 209R, which are rotated in engagement with the drive gear 215, and the pulleys 208U, 208D, 208L and 208R, respectively. The force transmission adjustment sections 209AU, 209AD, 209AL and 209AR transmit rotation of the driven gears 209U, 209D, 209L and 209R to the pulleys 208U, 208D, 208L and 208R, respectively.

The driven gears 209U, 209D, 209L and 209R are an up driven gear 209U, a down driven gear 209D, a left driven gear 209L and a right driven gear 209R. The up driven gear 209U is pivotally attached to an up shaft 216, the down driven gear 209D is pivotally attached to a down shaft 217, the left driven gear 209L is pivotally attached to a left shaft 218, and the right driven gear 209R is pivotally attached to a right shaft 219. The respective shafts 216, 217, 218 and 219 are fixed to a frame provided inside the operation portion 203.

Each of the respective force transmission adjustment sections 209AU, 209AD, 209AL and 209AR is configured by stacking a plurality of disc springs 209s so as to have a predetermined elastic characteristic. The up force transmission adjustment section (hereinafter abbreviated as "up adjustment section") 209AU is disposed on the up driven gear 209U. Likewise, the down force transmission adjustment section (hereinafter abbreviated as "down adjustment section") 209AD is disposed on the down driven gear 209D, the left force transmission adjustment section (hereinafter abbreviated as "left adjustment section") 209AL is disposed on the left driven gear 209L, and the right force transmission adjustment section (hereinafter abbreviated as "right adjustment section") 209AR is disposed on the right driven gear 209R.

Furthermore, the up pulley 208U is arranged on the up adjustment section 209AU, the down pulley 208D is arranged on the down adjustment section 209AD, the left pulley 208L is arranged on the left adjustment section 209AL, and the right pulley 208R is arranged on the right adjustment section 209AR.

Each of the adjustment sections 209AU, 209AD, 209AL and 209AR is configured by, for example, arbitrarily combining the disc springs 209s having different thickness directions, different longitudinal elastic moduli or different deflection amounts in series so that the adjustment sections are compressed by a predetermined amount with a predetermined load.

Note that through holes the respective disc springs 209s have, which extend in a shaft direction, are formed so that the respective shaft 216, 217, 218 or 219 is inserted through the through holes. Also, instead of the disc springs, a friction plate may be arranged in abutment with each pulley and a corresponding driven gear.

In the present embodiment, the drive gear 215 rotates counterclockwise as illustrated in FIG. 23. Accordingly, the respective driven gears 209U, 209D, 209L and 209R rotate clockwise.

As illustrated in FIGS. 22 to 24, the suspension frame 207 is included in a bending operation apparatus. The suspension frame 207 includes four frames 207U, 207D, 207L and 207R corresponding to upward, downward, leftward and rightward bending directions of the bending portion 202b, respectively, and is configured in a substantial cruciform. The suspension frame 207 includes a frame shaft 207a provided in a standing manner, which is a center shaft portion. The shaft portion 205a of the manipulator 205 and the frame shaft 207a of the suspension frame 207 are coaxially attached and fixed to each other via a universal joint 221.

The universal joint 221 is pivotally disposed in a non-illustrated frame provided inside the operation portion 203. The suspension frame 207 configured as described above swings with tilting of the manipulator 205.

The up frame 207U and the down frame 207D are arranged in a straight line across the frame shaft 207a. An up pulley pressing portion 207Ua is provided at an end portion of the up frame 207U. A down pulley pressing portion 207Da is provided at an end portion of the down frame 207D. On the other hand, the left frame 207L and the right frame 207R are perpendicular to a center line 207c of the frames for upward and downward bending, and are arranged in a straight line across the frame shaft 207a. A left pulley pressing portion 207La is provided at an end portion of the left frame 207L. A right pulley pressing portion 207Ra is provided at an end portion of the right frame 207R.

As illustrated in FIGS. 23 and 24, the pulley pressing portions 207Ua, 207Da, 207La and 207Ra are each formed in a predetermined shape. The respective pulley pressing portions 207Ua, 207Da, 207La and 207Ra project from one side faces of the respective frames 207U, 207D, 207L and 207R so that the respective pulley pressing portions 207Ua, 207Da, 207La and 207Ra are arranged on the respective pulleys 208U, 208D, 208L and 208R. A pressing member is fixed to a face on the pulley side of each of the pulley pressing portions 207Ua, 207Da, 207La and 207Ra. The pressing members are arranged in direct abutment with the respective pulleys 208U, 208D, 208L and 208R. Each pressing member is a rigid resin member of, for example, fluorine resin with pressing ability and slidability taken into account.

Note that a configuration in which the pulley pressing portions 207Ua, 207Da, 207La and 207Ra are in direct abutment with the respective pulleys 208U, 208D, 208L and 208R without the pressing members being fixed to the respective pulley-side faces may be employed.

Also, when the manipulator 205 stands upright, in other words, the bending portion 202b is in a straightened state as illustrated in FIG. 22, a pre-set gap is provided between a pressing member fixed to each pulley pressing portion 207Ua, 207Da, 207La or 207Ra and the respective pulley 208U, 208D, 208L or 208R. The respective pulleys 208U, 208D, 208L and 208R are provided so as to face the respective pulley pressing portions 207Ua, 207Da, 207La and 207Ra.

Figure 25:
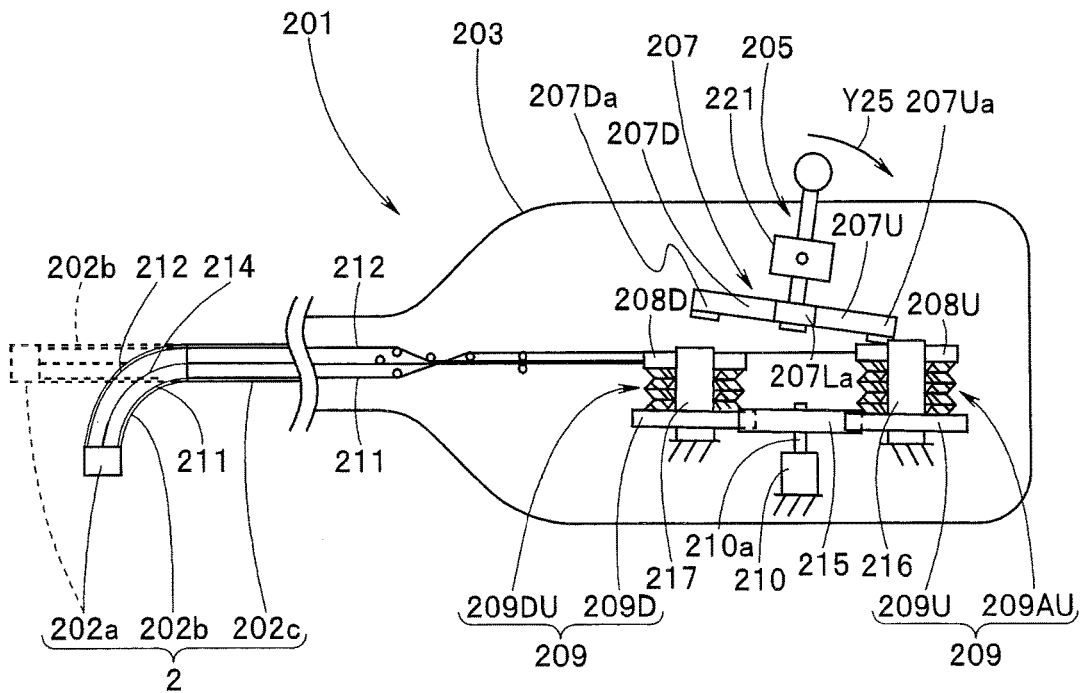

With such configuration, for example, when an operator performs an operation to bend the bending portion 202b upward, that is, tilts the manipulator 205 in the arrow Yu direction, the suspension frame 207 is swung as illustrated in FIG. 25. At this time, the up frame 207U moves close to the up pulley 208U while the down frame 207D moves away from the down pulley 208D.

Note that in FIGS. 24 and 25, in order to describe an operation of the bending portion to bend upward, the pulleys 208U and 208D, the adjustment sections 209AU and 209AD and the driven gears 209U and 209D for upward/downward bending are illustrated, and the pulleys 208L and 208R, the adjustment sections 209AL and 209AR and the driven gears 209L and 209R relating to leftward/rightward bending are omitted in the Figures.

For bending the bending portion 202b upward, an operator continuously tilts the manipulator 205 in the Y25 direction. When the operator starts tilting the manipulator 205, first, the pressing member of the pulley pressing portion 207Ua abuts against the up pulley 208U. Subsequently, with the tilting, the up pulley 208U moves along the up shaft 216 against a biasing force of the up adjustment section 209AU. In other words, the up pulley 208U is depressed toward the up driven gear 209U.

Figure 26A:
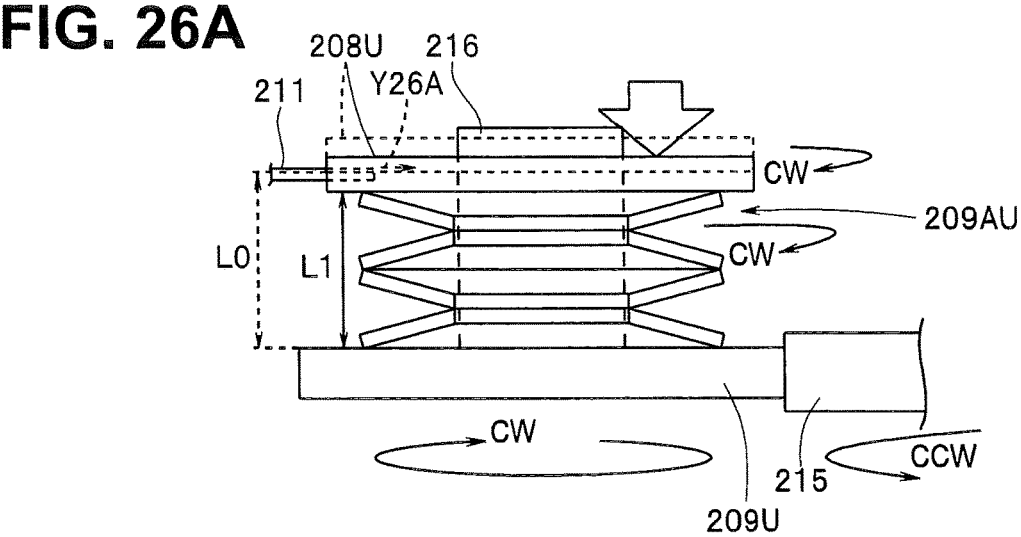
FIG. 26A is a diagram illustrating a state in which a pulley has started rotating as a result of the pulley being depressed by a pressing portion of the suspension frame.

As the up pulley 208U is depressed, the up adjustment section 209AU is compressed. Then, as illustrated in FIG. 26A, a distance L between the up pulley 208U and the up driven gear 209U changes from a distance L0, which is an initial state, to a distance L1. If the distance L becomes L1, rotation of the up driven gear 209U is transmitted to the up pulley 208U via the up adjustment section 209AU. In other words, the up pulley 208U rotates and the up bending wire 211 is thereby pulled as illustrated by the dashed arrow Y26A. Then, the bending portion 202b starts bending. In other words, until the distance L reaches the distance L1, the up driven gear 209U alone is rotated by the drive gear 215.

Figure 26B:
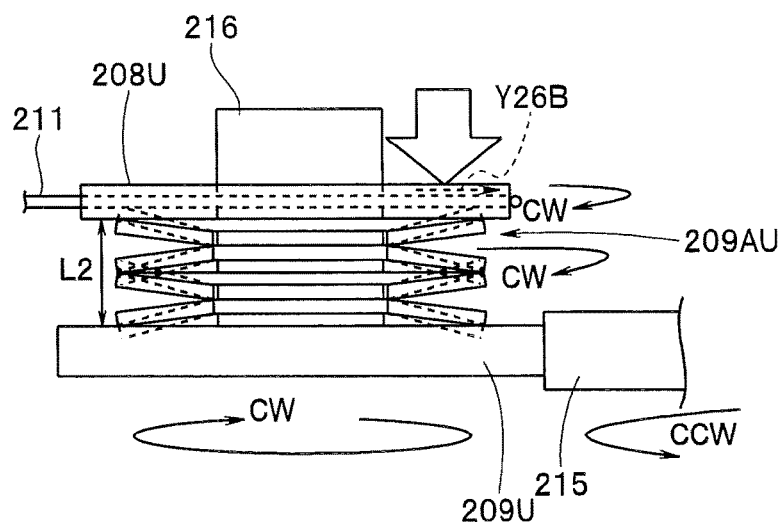
FIG. 26B is a diagram illustrating a state in which a bending wire has been moved with further rotation of the pulley resulting from the pulley being further depressed by the pressing portion of the suspension frame.

Subsequently, as an angle of tilting of the manipulator 205 continuously is increased, the up pulley 208U is further moved toward the up driven gear 209U by the pulley pressing portion 7Ua. As a result, as illustrated in FIG. 26B, the distance L between the up pulley 208U and the up driven gear 209U changes to a distance L2. At this time, the rotation of the up driven gear 209U is transmitted to the up pulley 208U via the up adjustment section 209AU. Then, the up pulley 208U rotates. As a result, the up bending wire 211 is further pulled as indicated by the dashed arrow Y26B and the bending portion 202b is thereby bent, for example as indicated by solid lines in FIG. 25.

Figure 26C:
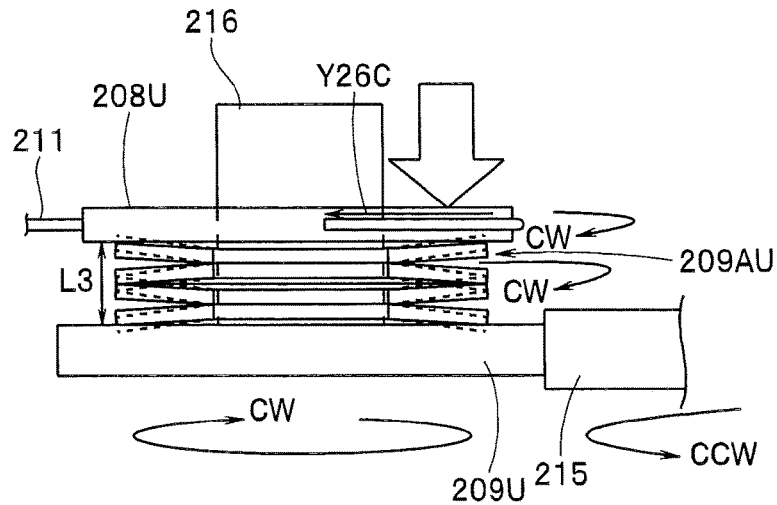

Subsequently, when the manipulator 205 reaches a predetermined maximal tilting angle, as illustrated in FIG. 26C, the distance L between the up pulley 208U and the up driven gear 209U becomes a distance L3. At this time, the rotation of the up driven gear 209U is transmitted to the up pulley 208U via the up adjustment section 209AU. Then, the up pulley 208U rotates. As a result, the up bending wire 211 is further pulled as indicated by the arrow Y26C and the bending portion 202b is thereby maximally bent.

In the present embodiment, an amount of operation strength for tilting the manipulator 205 increases with an increase in tilting angle. More specifically, when the manipulator 205 is tilted, for example, the up pulley 208U starts moving along the up shaft 216 toward the up driven gear 209U against a biasing force of the up adjustment section 209AU. Then, the distance L between the up pulley 208U and the up driven gear 209U becomes the distance L1 and pulling of the up bending wire 211 is thereby started. At this time, as an angle of bending of the bending portion 202b increases, the amount of tilting operation strength increases. In other words, as the angle of tilting of the manipulator 205 increases, the up adjustment section 209AU increases the amount of tilting operation strength and transmits the rotation of the up driven gear 209U to the up pulley 208U to rotate the pulley 208U by an angle corresponding to the tilting operation strength amount.

In the present embodiment, a maximal operation strength amount for the manipulator 205, that is, a tilting operation strength amount to maximally bend the bending portion 202b is set to a predetermined value by adjusting the biasing force of the up adjustment section 209AU. The value exhibits a small strength amount compared to an operation strength amount for a case where the up bending wire 211 is directly pulled by operating the manipulator 205.

Note that in the above, an operation performed by an operator to tilt the manipulator 205 to bend the bending portion 202b upward has been described. However, even where an operator tilts the manipulator 205 to bend the bending portion 202b in a direction other than the upward direction, an amount of operation strength for tilting the manipulator 205 increases with an increase in titling angle. Then, after pulling of the bending wire 212, 213 or 214 is started, and the amount of tilting operation strength increases as the angle of bending of the bending portion 202b increases.

The amount of tilting operation strength can be set to a desired value by arbitrarily setting lengths of the frames 207U, 207D, 207L and 207R and biasing forces of the adjustment sections 209AU, 209AD, 209AL and 209AR.

Here, a bending operation of the bending portion 202b of the endoscope 201 configured as described above will be described.

When an operator inserts the insertion portion 202 to a body from, e.g., an oral cavity, the operator drives the motor 210 in the operation portion 203 to bring the respective driven gears 209U, 209D, 209L and 209R into a rotating state. At this time, a gap is provided between each of the pulleys 208U, 208D, 208L and 208R and the pressing member of the respective pulley pressing portion 207Ua, 207Da, 207La or 207Ra, and the bending portion 202b is straightened.

The operator starts inserting the insertion portion 202 into the body while observing an endoscopic image displayed on a screen of a non-illustrated observation apparatus.

In order to, for example, bend the bending portion 202b upward, as illustrated in FIG. 25, the operator tilts the manipulator 205 in the arrow Y25 direction. Then, the manipulator 205 and the suspension frame 207 integrally swing. As a result, the up pulley pressing portion 7Ua provided on the up frame 207U of the suspension frame 207 is arranged on a surface of the pulley 208U. Subsequently, the pulley 208U moves along the up shaft 216 toward the up driven gear 209U. At this time, as the angle of tilting of the manipulator 205 increases, the amount of tilting operation strength gradually increases.

When the distance L between the up pulley 208U and the up driven gear 209U reaches the distance L1, the rotation of the up driven gear 209U is transmitted to the up pulley 208U via the up adjustment section 209AU. In other words, the up driven gear 209U, the up adjustment section 209AU and the up pulley 208U integrally start rotational angle change.

Then, the up bending wire 211 fixed to the up pulley 208U is pulled with the change in rotational angle of the up pulley 208U. As a result, bending of the bending portion 202b is started. Subsequently, as a result of the manipulator 205 being continuously tilted, the distance between the up pulley 208U and the up driven gear 209U is gradually reduced. At this time, the amount of tilting operation strength for operating the manipulator 205 gradually increases. Also, the rotational angles of the up driven gear 209U, the up adjustment section 209AU and the up pulley 208U gradually increase while the up driven gear 209U, the up adjustment section 209AU and the up pulley 208U remain in an integrated state or slide relative to one another. As a result, the up bending wire 211 is further pulled and the angle of bending of the bending portion 202b thereby increases.

If the operator continues tilting the manipulator 205, the distance between the up pulley 208U and the up driven gear 209U is continuously reduced. As a result, the rotational angles of the up driven gear 209U, the up adjustment section 209AU and the up pulley 208U increase as the up driven gear 209U, the up adjustment section 209AU and the up pulley 208U remain in an integrated state. Accordingly, the up bending wire 211 is further pulled and the bending portion 202b is thereby further bent upward.

On the other hand, if the operator holds the angle of tilting of the manipulator 205 in a tilted state during tilting of the manipulator 205, the rotational angles are held while the up driven gear 209U, the up adjustment section 209AU and the up pulley 208U remain in an integrated state or slide relative to one another. In other words, the angle of bending of the bending portion 202b is held in a bent state.

In the present embodiment, during the manipulator 205 being tilted, if, for example, the distal end portion 202a abuts against, e.g., a wall of a lumen, a bending operation of the bending portion 202b is interrupted by the wall. At this time, it may become impossible to pull the up bending wire 211. In this case, during a tilting operation to bend the bending portion 202b, an operator that is operating the endoscope 201 feels that as the bending angle increases, the amount of operation strength for operating the manipulator 205 increases, by pressure on his/her hand.

Thus, during the tilting operation, if an endoscopic image displayed on a screen of a display apparatus has no change despite an increase in amount of operation strength for tilting the manipulator 205, the operator can see a trouble in the bending portion such as the distal end portion 202a of the insertion portion 202 abutting against, e.g., a wall of a lumen.

As described above, with the endoscope 201 according to the present embodiment, the manipulator 205 provided in the operation portion 203 is tilted in any direction of upward, downward, leftward and rightward. Then, the bending wire 211, 212, 213 or 214 corresponding to the tilting is not directly pulled, but the pulley 208U, 208D, 208L or 208R corresponding to the tilting moves toward the driven gear 209U, 209D, 209L or 209R relative to the shaft 216, 217, 218 or 219 against the biasing force of the adjustment section 209AU, 209AD, 209AL or 209AR. Then, the distance L between the pulley 208U, 208D, 208L or 208R and the driven gear 209U, 209D, 209L or 209R becomes the predetermined distance L1. At this time, rotation of the driven gear 209U, 209D, 209L or 209R is transmitted to the pulley 208U, 208D, 208L or 208R via the adjustment section 209AU, 209AD, 209AL or 209AR. Then, the driven gear 209U, 209D, 209L or 209R, the adjustment section 209AU, 209AD, 209AL or 209AR and the pulley 208U, 208D, 208L or 208R integrally rotate by a predetermined angle. As a result, the bending wire 211, 212, 213 or 214 with the other end fixed to the pulley 208U, 208D, 208L or 208R corresponding to the tilting is pulled and the bending portion 202b thereby bends in the direction corresponding the tilting.

In the configuration, the amount of operation strength for tilting the manipulator 205 is set in advance to be smaller than the amount of strength to directly pull the bending wire 211, 212, 213 or 214 by operating the manipulator 205. Thus, a bending operation of the bending portion 202b can easily be performed by tilting the manipulator 205 provided at the operation portion 203.

Also, as described above, the amount of operation strength for tilting the manipulator 205 is set in advance to be smaller than an amount of strength for directly pull each bending wire 211, 212, 213 or 214 by operating the manipulator 205, and the configuration is provided so that as a tilting operation is performed to increase the bending angle of the bending portion 202b, the amount of strength for the tilting operation increases. As a result, a change in stress occurs on the bending wire 211, 212, 213 or 214, and the respective pulley 208U, 208D, 208L or 208R rotates according to the stress change. Also, the rotation causes a frictional force to occur in a circumferential direction of the pulley 208U, 208D, 208L or 208R between the suspension frame 207 and the respective pulley 208U, 208D, 208L or 208R. As a result of the suspension frame 207 moving in the circumferential direction, a force in a direction opposite to the direction in which the manipulator 205 is intended to be tilted is generated on the manipulator 205. Accordingly, during a tilting operation to bend the bending portion 202b, the operator senses a change in stress on the relevant bending wire 211, 212, 213 or 214 from an endoscopic image displayed on the display apparatus and a change in amount of tilting operation strength, enabling prevention of a trouble due to an abnormality in the bending of the bending portion 202b.

Note that the bending portion 202b bent by tilting the manipulator 205 restores to a straightened state by an elastic repellent force the bending portion 202b has, by returning the manipulator 205 to an upright position.

A second embodiment of the present appendices will be described with reference to FIGS. 27 to 31D.

Figure 27:
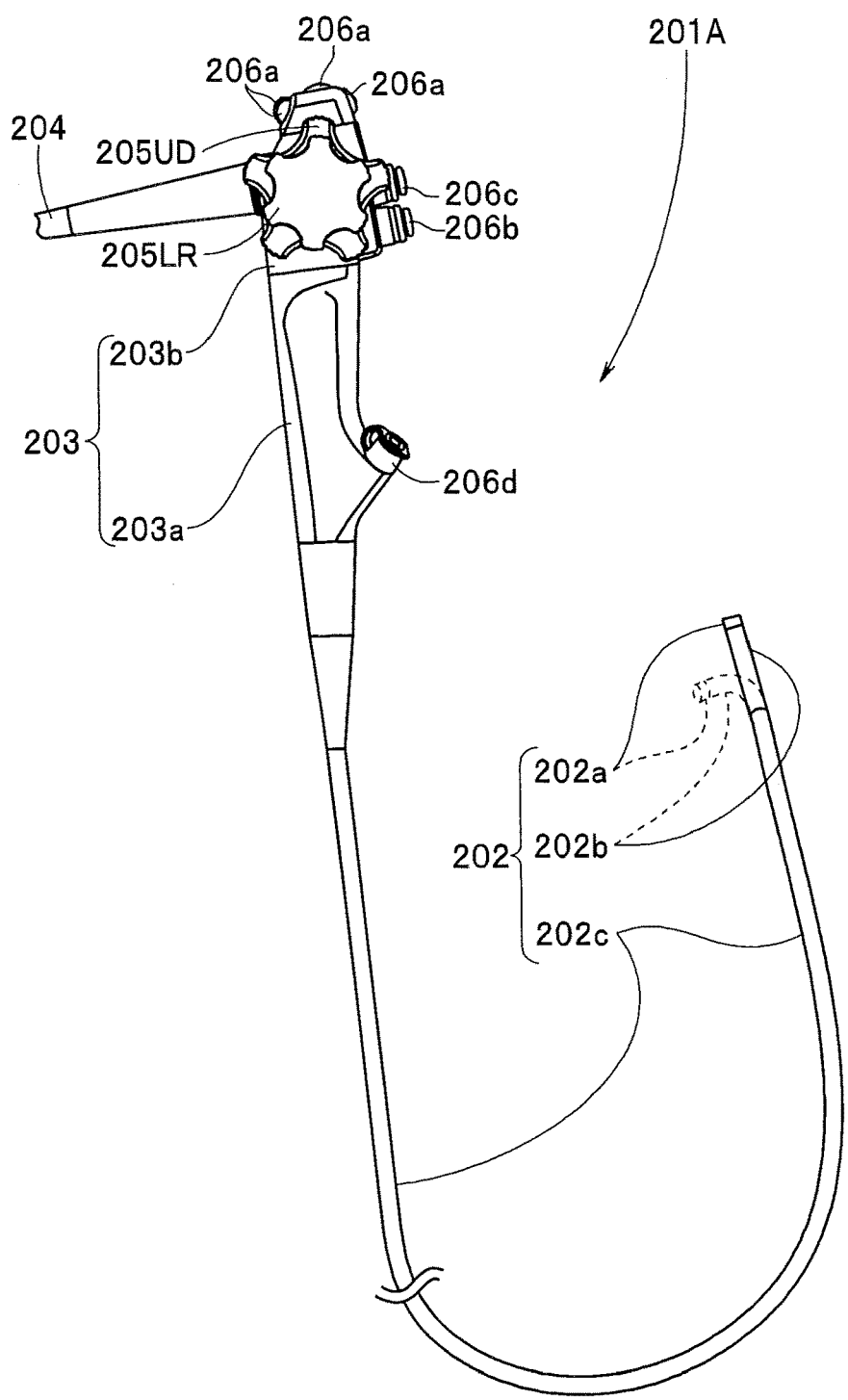
Figure 28:
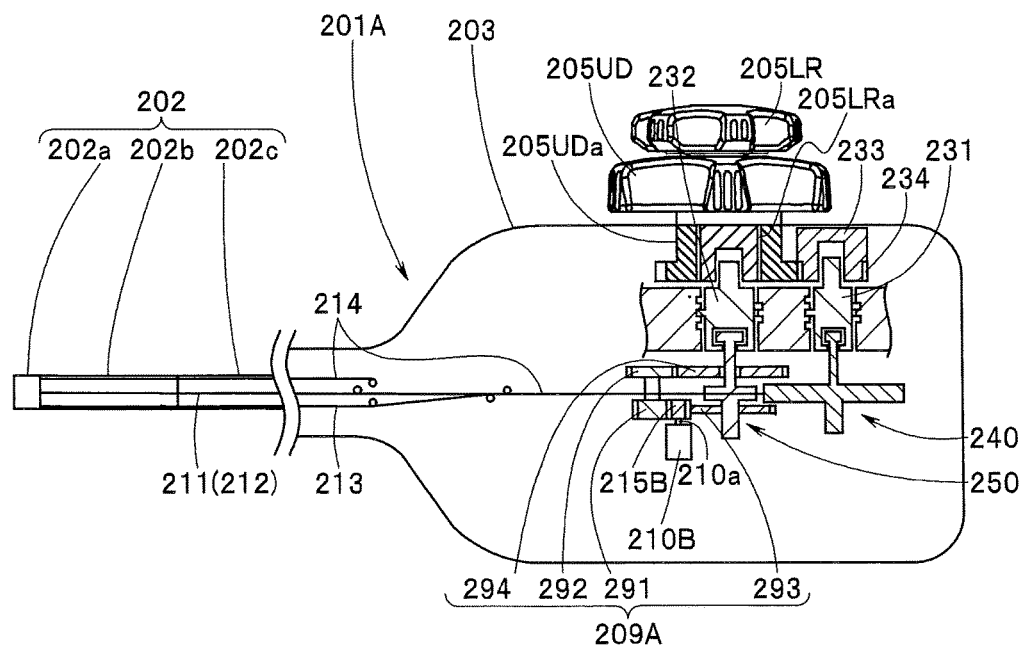

As illustrated in FIG. 27, in an endoscope 201A according to the present embodiment, an up/down bending knob (hereinafter abbreviated as "up/down knob") 205UD, which is an operation dial, and a left/right bending knob (hereinafter referred to as "left/right knob") 205LR, which is an operation dial, are arranged at an outer peripheral face of an operation portion 203. As illustrated in FIG. 28, inside the operation portion 203, an up/down shaft portion 205UDa of the up/down knob 205UD, a left/right shaft portion 205LRa of the left/right knob 205LR, an up/down cam shaft 231, a left/right cam shaft 232, a cam shaft gear 233, an up/down pulley section 240, a left/right pulley section 250, a drive force transmission section 209A, a motor 210B and bending wires 211, 212, 213 and 214 are mainly provided. Note that members that are the same as those of the above-described first embodiment are provided with reference numerals that are the same as those of the first embodiment, and a description thereof will be omitted.

In the present embodiment, as with the first embodiment as illustrated in FIG. 28, one ends of the bending wires 211, 212, 213 and 214 are fixed at respective predetermined positions on the distal end side of the bending portion 202b.

Figure 29:
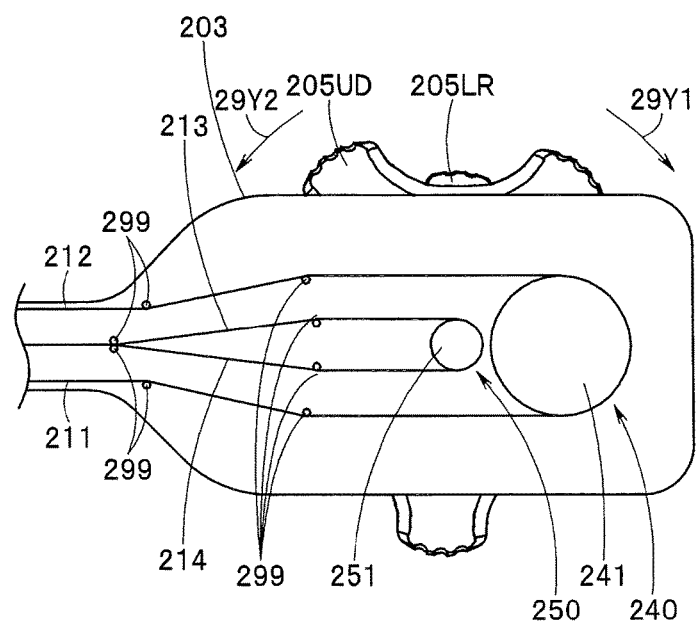

On the other hand, as illustrated in FIG. 29, the other end of the up bending wire 211 is fixed at a predetermined position on an up/down wire fixing pulley 241 in the up/down pulley section 240, and the other end of the down bending wire 212 is fixed at a predetermined position on the up/down wire fixing pulley 241. Also, the other end of the left bending wire 213 is fixed at a predetermined position on the left/right wire fixing pulley 251 of the left/right pulley section 250, and the other end of the right bending wire 214 is fixed at a predetermined position of the left/right wire fixing pulley 251.

The respective bending wires 211, 212, 213 and 214 are introduced into the operation portion 203, and then subjected to change in respective running routes by, for example, a plurality of guide rollers 299 and are tightened with a predetermined tensile force.

Figure 30:
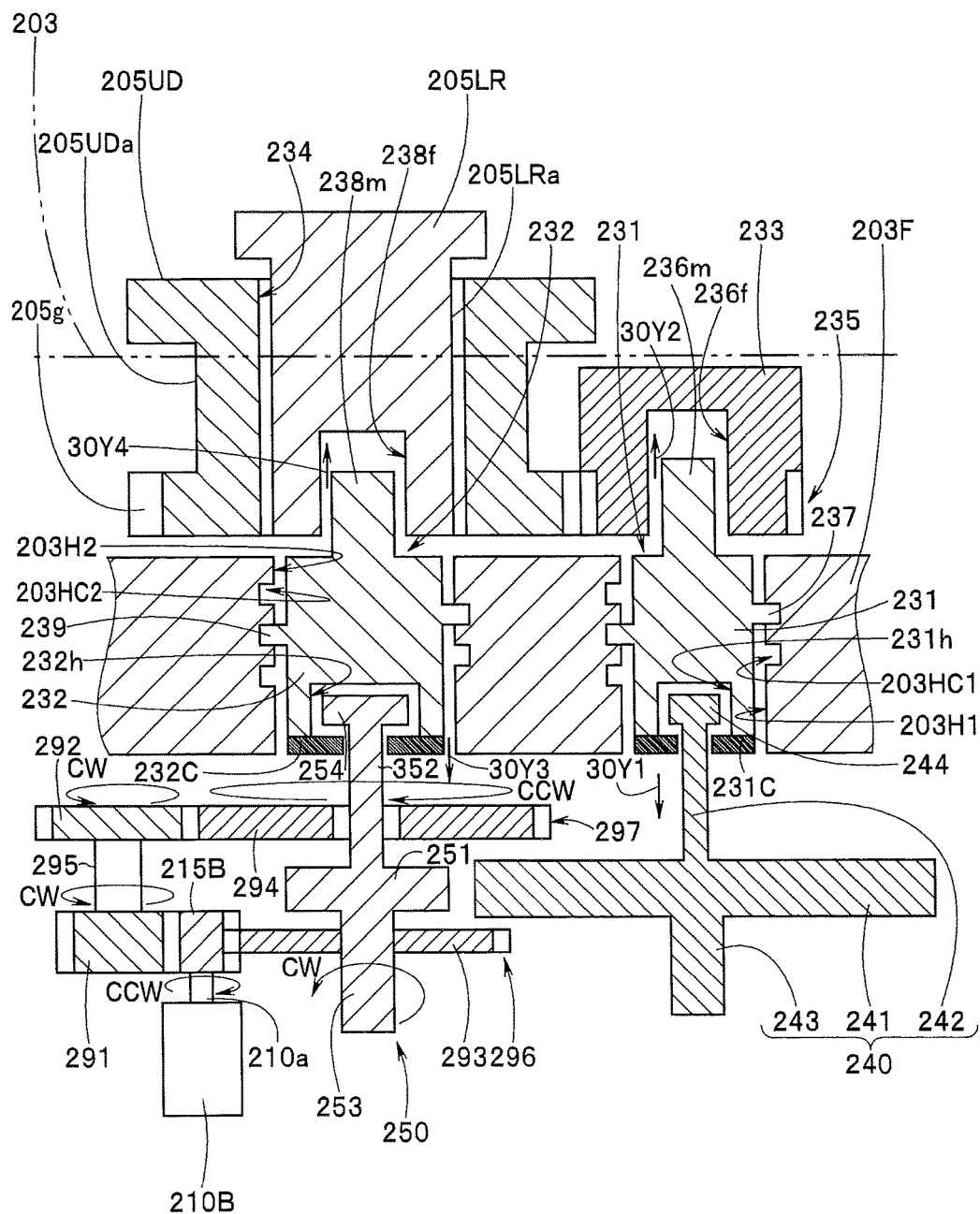

As illustrated in FIGS. 28 and 30, the drive force transmission section 209A in the present embodiment includes a first driven gear 291, a second driven gear 292, a first friction plate 293 and a second friction plate 294.

The first driven gear 291 and the second driven gear 292 are integrally fixed to one end and the other end of a transmission shaft 295, respectively. The first friction plate 293 and the second friction plate 294 are arranged so as to face each other across the left/right wire fixing pulley 251 and the up/down wire fixing pulley 241.

To a motor shaft 210a of the motor 210B, a drive gear 215B is fixed. The first driven gear 291 and a first gear wheel 296 engage with the drive gear 215B. The first gear wheel 296 is an external gear wheel formed on an outer peripheral face of the first friction plate 293. Also, a second gear wheel 297 engages with the second driven gear 292. The second gear wheel 297 is an external gear wheel formed on an outer peripheral face of the second friction plate 294. In the present embodiment, a drive section is formed by the motor 210B, the drive gear 215B, the first friction plate 293 and the second friction plate 294. The first friction plate 293 is rotated by the drive gear 215B, and the second friction plate 294 is rotated by the second driven gear.

In the present embodiment, the drive gear 215B rotates, for example, counterclockwise. Accordingly, the first driven gear 291, the second driven gear 292 and the first friction plate 293 rotate clockwise. On the other hand, the second friction plate 294 rotates counterclockwise.

As illustrated in FIGS. 28 to 30, in the present embodiment, the up/down knob 205UD is included in an up/down bending operation apparatus. The up/down bending operation apparatus includes the up/down knob 205UD, the cam shaft gear 233, the up/down cam shaft 231 and the up/down pulley section 240.

On the other hand, the left/right knob 205LR is included in the left/right bending operation apparatus. The left/right bending operation apparatus includes the left/right knob 205LR, the left/right cam shaft 232 and the left/right pulley section 250.

The knobs 205UD and 205LR can be rotated clockwise or counterclockwise. In other words, the knobs 205UD and 205LR are pivotable. Making the up/down knob 205UD pivot enables a provision of an operation instruction to bend the bending portion 202b upward or downward by a desired angle. On the other hand, making the left/right knob 205LR pivot enables a provision of an operation instruction to bend the bending portion 202b leftward or rightward by a desired angle.

The up/down knob 205UD includes the up/down shaft portion 205UDa. An external gear wheel 205g is provided at a predetermined position on an outer peripheral face of the up/down shaft portion 205UDa. In the up/down shaft portion 205UDa, an axial through hole 234 is formed. The left/right shaft portion 205LRa included in the left/right knob 205LR is inserted through the axial through hole 234 by means of predetermined fitting.

The cam shaft gear 233 includes a gear portion 235. The gear portion 235 is configured to engage with the external gear wheel 205g. An up/down engagement recess portion 236f that has a predetermined shape is formed at a predetermined position in the cam shaft gear 233.

The up/down cam shaft 231 is an instruction member, and includes protrusions 237 at an outer peripheral face thereof. The protrusions 237 are formed on an inner peripheral face of an up/down cam shaft arrangement hole 203H1 formed in a frame 203F. The protrusions 237 are slidably arranged in respective up/down cam grooves 203HC1 each having a predetermined shape.

The up/down cam shaft 231 includes an up/down engagement projection portion 236m, which is arranged in the up/down engagement recess portion 236f. When the up/down engagement projection portion 236m engages with the up/down engagement recess portion 236f, the up/down cam shaft 231 rotates together with the cam shaft gear 233.

Note that reference numeral 231h denotes an up/down transmission hole in which a later-described up/down protrusion is arranged.

With the above-described configuration, rotation of the up/down knob 205UD is transmitted to the up/down cam shaft 231 via the up/down shaft portion 205UDa including the external gear wheel 205g, the cam shaft gear 233 including the gear portion 235, and the up/down engagement recess portion 236f and the up/down engagement projection portion 236m that are engaged with each other. As a result, with the operation to make the up/down knob 205UD pivot, the up/down cam shaft 231 advances/retracts in the arrow 30Y1/30Y2 directions relative to the up/down cam shaft arrangement hole 203H1 of the frame 203F.

On the other hand, a left/right engagement recess portion 238f having a predetermined shape is formed at a predetermined position in the left/right shaft portion 205LRa arranged in the axial through hole 234 of the up/down shaft portion 205UDa.

The left/right cam shaft 232 is an instruction member, and includes protrusions 239 at an outer peripheral face thereof. The protrusions 239 are slidably arranged in respective left/right cam grooves 203HC2. The left/right cam grooves 203HC2 are formed at an inner circumferential face of a left/right cam shaft arrangement hole 203H2 formed in the frame 203F.

Also, the left/right cam shaft 232 includes a left/right engagement projection portion 238m, which is arranged in the left/right engagement recess portion 238f. When the left/right engagement projection portion 238m engages with the left/right engagement recess portion 238f, the left/right cam shaft 232 rotates together with the left/right shaft portion 205LRa.

Note that reference numeral 232h denotes a left/right transmission hole in which a later-described left/right protrusion is arranged.

With the above-described configuration, rotation of the left/right knob 205LR is transmitted to the left/right cam shaft 232 via the left/right engagement recess portion 238f and the left/right engagement projection portion 238m that are engaged with each other. As a result, with the operation to make the left/right knob 205LR pivot, the left/right cam shaft 232 advances/retracts in the arrow 30Y3/30Y4 direction relative to the left/right cam shaft arrangement hole 203H2 of the frame 203F.

The up/down pulley section 240 includes the up/down wire fixing pulley 241, an up/down transmission shaft 242 and an up/down support shaft 243. The up/down transmission shaft 242 is a first shaft projecting from one surface side of the pulley 241. The up/down support shaft 243 is a second shaft projecting another surface side of the pulley 241. An up/down protrusion 244 included in the drive force transmission section is provided at an end portion of the up/down transmission shaft 242. The up/down protrusion 244 is arranged in the up/down transmission hole 231h included in the drive force transmission section. The up/down transmission hole 231h is occluded by a lid member 231C included in the drive force transmission section. The lid member 231C includes an opening through which the up/down transmission shaft 242 is inserted. An end portion of the up/down support shaft 243 is pivotally supported in a non-illustrated frame.

On the other hand, the left/right pulley section 250 includes the left/right pulley 251, a left/right transmission shaft 252 and a left/right support shaft 253. The left/right transmission shaft 252 projects from one surface side of the pulley 251. The left/right support shaft 253 projects from another surface side of the pulley 251. A left/right protrusion 254 included in the drive force transmission section is provided at an end portion of the left/right transmission shaft 252. The left/right protrusion 254 is arranged in the left/right transmission hole 232h included in the drive force transmission section. The left/right transmission hole 232h is occluded by a lid member 232C included in the drive force transmission section. The lid member 232C includes an opening through which the left/right transmission shaft 252 is inserted. An end portion of the left/right support shaft 253 is pivotally supported in a non-illustrate frame.

Figure 31A:
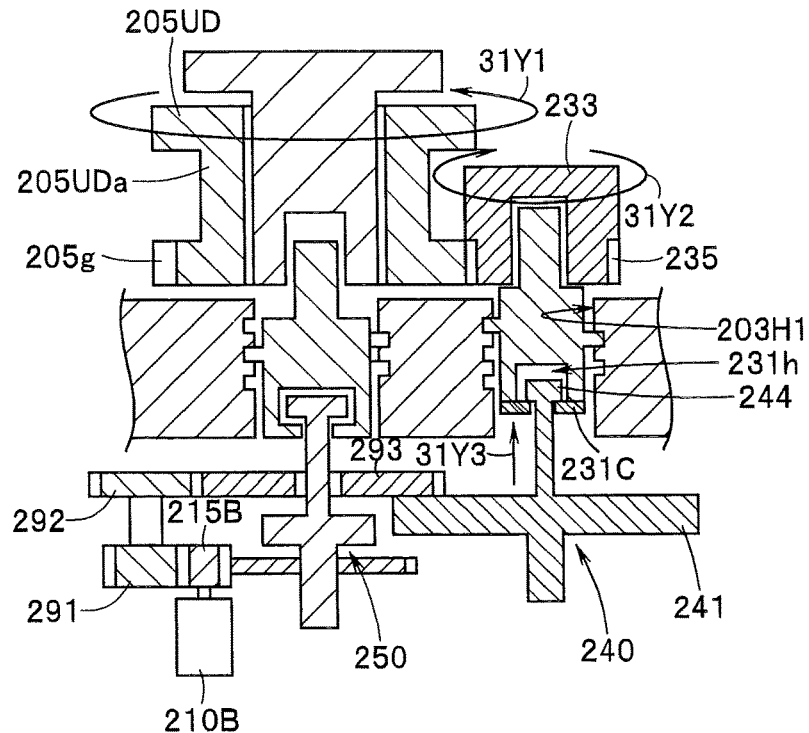
FIG. 31A is a diagram illustrating a relationship among the shaft portion of the up/down bending knob, the up/down cam shaft, the cam shaft gear, the up/down pulley section, the drive force transmission section, the motor and an up bending wire when a bending portion is bent upward.
Figure 31B:
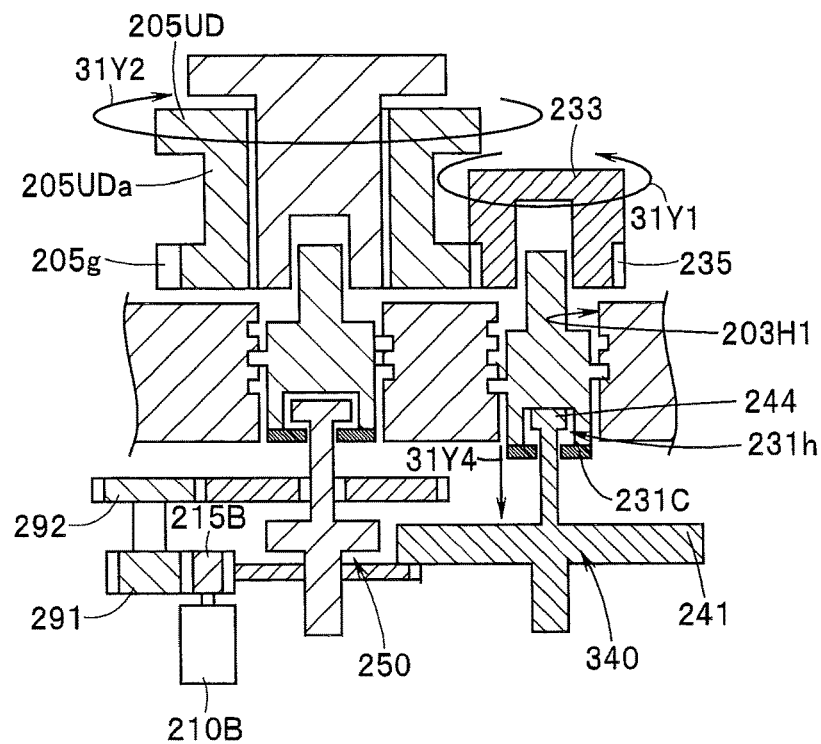
FIG. 31B is a diagram illustrating a relationship among the shaft portion of the up/down bending knob, the up/down cam shaft, the cam shaft gear, the up/down pulley section, the drive force transmission section, the motor and a down bending wire when the bending portion is bent downward.
Figure 31C:
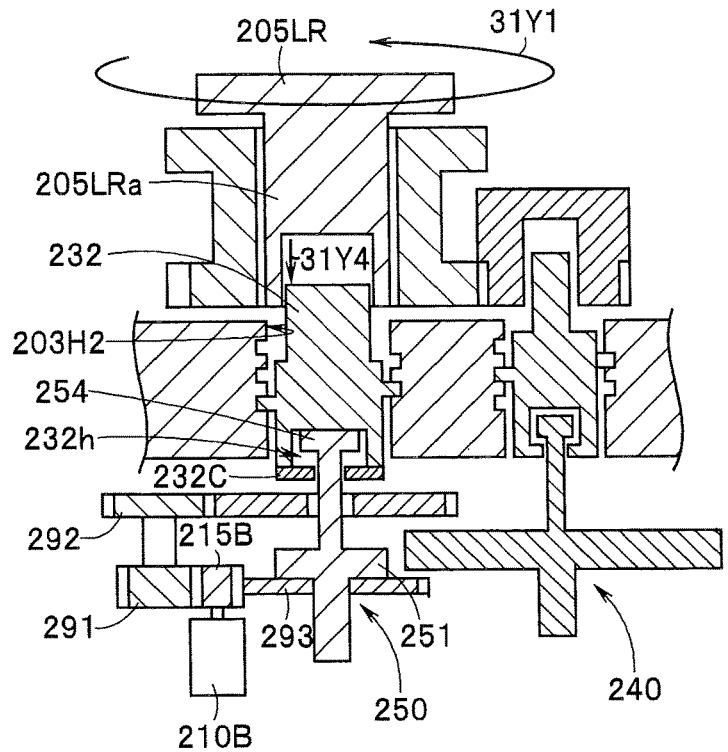
FIG. 31C is a diagram illustrating a relationship among the shaft portion of the left/right bending knob, the left/right cam shaft, the left/right pulley section, the drive force transmission section, the motor and a left bending wire when the bending portion is bent leftward.
Figure 31D:
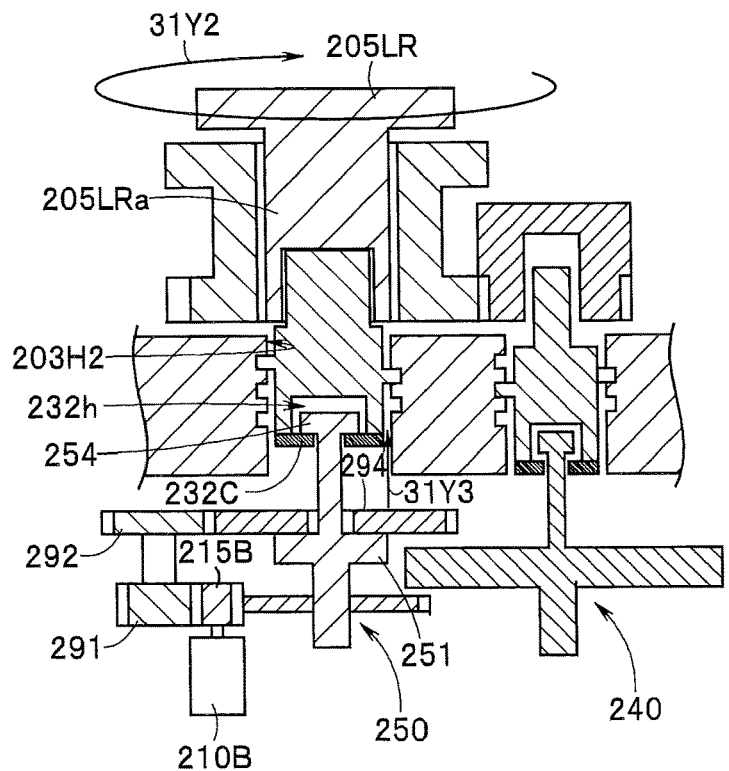

With these configurations, for example, when an operator performs an operation to bend the bending portion 202b upward, that is, rotates the up/down knob 205UD illustrated in FIG. 29 in the arrow 29Y1 direction, the up/down knob 205UD rotates in the arrow 31Y1 direction in FIG. 31A. Accordingly, the cam shaft gear 233 including the gear portion 235 that engages with the external gear wheel 205g included in the up/down shaft portion 205UDa rotates in the arrow 31Y2 direction, which is the opposite direction. Then, with the rotation of the cam shaft gear 233, the up/down cam shaft 231 moves in the arrow 31Y3 direction relative to the up/down cam shaft arrangement hole 203H1.

As a result of the up/down cam shaft 231 moving in the arrow 31Y3 direction, the lid member 231C gradually approaches and then abuts against the up/down protrusion 244. The up/down knob 205UD is continuously rotated in the arrow 31Y1 direction even after the abutment, whereby the up/down cam shaft 231 is further moved in the arrow 31Y3 direction. Then, with the movement, the up/down pulley section 240 further moves in the arrow 31Y3 direction together with the up/down cam shaft 231, whereby the one surface of the up/down wire fixing pulley 241 of the up/down pulley section 240 abuts against the second friction plate 294.

As a result of the abutment of the one surface of the up/down wire fixing pulley 241 with the second friction plate 294 providing a change to an abutment state with a predetermined pressing force, rotation of the second friction plate 294 is transmitted to the up/down wire fixing pulley 241. As a result, the up/down wire fixing pulley 241 starts rotating in the arrow 31Y2 (arrow 29Y2 in FIG. 29) direction. Then, the up bending wire 211 fixed to the up/down wire fixing pulley 241 is pulled while the down bending wire 212 is slackened, whereby the bending portion 202b starts bending upward.

Subsequently, the operator continues providing a force for rotating the up/down knob 205UD in the arrow 31Y1 direction. Then, a pressing force of the one surface of the up/down wire fixing pulley 241 pressing the second friction plate 294 gradually increases. As a result, rotation of the second friction plate 294 is transmitted to the up/down wire fixing pulley 241, whereby a rotational angle of the pulley 241 is changed. Then, the up bending wire 211 is further pulled, whereby the bending portion 202b becomes close to a maximal bending state.

Note that when the aforementioned pressing force increases, the up/down knob 205UD, the cam shaft gear 233 and the up/down cam shaft 231 are halted without moving and the pressing force alone increases.

In the present embodiment, an amount of operation strength for rotating the up/down knob 205UD varies among a step in the cam shaft gear 233 and the up/down cam shaft 231 are rotated by the rotation of the knob 205UD, which is a first step, a step in which the up/down cam shaft 231 is moved by the rotation of the knob 205UD, which is a second step, and a step in the up/down wire fixing pulley 241 is made to press the second friction plate 294 by the rotation of the knob 205UD, which is a third step, respectively. More specifically, the amount of rotation operation strength increases in a stepwise manner from the first step to the second step and from the second step to the third step. In addition, in the third step, the amount of rotation operation strength increases little by little from the start of the bending of the bending portion 202b as a rotational angle of the bending portion 202b changes to reach the maximal bending state.

Then, in the present embodiment, a maximum operation strength amount for the up/down knob 205UD, that is, an operation strength amount for bending the bending portion 202b maximally is set to a predetermined value. The value corresponds to a strength amount that is smaller than an operation strength amount when the up bending wire 211 is directly pulled by operating the up/down knob 205UD.

The maximum operation strength amount can be set to a desired value by arbitrarily setting a relationship between shapes of the protrusions 237 and the up/down cam grooves 203HC1, that is, e.g., cam angles and cam pitches.

Note that where the operator performs an operation to bend the bending portion 202b downward, as illustrated in FIG. 29, the operator rotates the up/down knob 205UD in the arrow 29Y2 direction. Here, in FIG. 31B, the up/down knob 205UD rotates in the arrow 31Y2 direction, and with that rotation, as described above, the cam shaft gear 233 is rotated in the arrow 31Y1 direction, which is the opposite direction. As a result, the up/down cam shaft 231 moves in the arrow 31Y4 direction relative to the up/down cam shaft arrangement hole 203H1. As a result of the up/down cam shaft 231 moving in the arrow 31Y4 direction, a bottom face of the up/down transmission hole 231h and the up/down protrusion 244 gradually approach and then abut against each other. The up/down knob 205UD is continuously rotated in the arrow 31Y2 direction even after the abutment, whereby the up/down cam shaft 231 is further moved in the arrow 31Y4 direction. Then, with the movement, the up/down pulley section 240 further moves in the arrow 31Y4 direction together with the up/down cam shaft 231, whereby the other surface of the up/down wire fixing pulley 241 abuts against the first friction plate 293.

As a result of the abutment of the other surface of the up/down wire fixing pulley 241 with the first friction plate 293 providing a change to an abutment state with a predetermined pressing force, rotation of the first friction plate 293 is transmitted to the up/down wire fixing pulley 241. As a result, the up/down wire fixing pulley 241 starts rotating in the arrow 31Y1 (arrow 29Y1 in FIG. 29) direction. Then, the down bending wire 212 fixed to the up/down wire fixing pulley 241 is pulled while the up bending wire 211 is slackened, whereby the bending portion 202b starts bending downward.

Subsequently, the operator continues providing a force for rotating the up/down knob 205UD in the arrow 31Y2 direction, whereby a pressing force of the other surface of the up/down wire fixing pulley 241 pressing the first friction plate 293 gradually increases. As a result, the rotation of the first friction plate 293 is transmitted to the pulley 241, which thereby rotates. Then, the down bending wire 212 is further pulled, whereby the bending portion 202b becomes close to a maximal bending state. At this time, as described above, the up/down knob 205UD, the cam shaft gear 233 and the up/down cam shaft 231 are halted.

Also, where the operator performs an operation to bend the bending portion 202b leftward, the operator rotates the left/right knob 205LR illustrated in FIG. 29 in the arrow 29Y1 direction. Here, in FIG. 31C, the left/right knob 205LR rotates in the arrow 31Y1 direction, and with that rotation, the left/right cam shaft 232 moves in the arrow 31Y4 direction relative to the left/right cam shaft arrangement hole 203H2. As a result of the left/right cam shaft 232 moving in the arrow 31Y4 direction, a bottom face of the left/right transmission hole 232h gradually approaches and then abuts against the left/right protrusion 254. The left/right knob 205LR is continuously rotated in the arrow 31Y1 direction even after the abutment, whereby the left/right cam shaft 232 is further moved in the arrow 31Y4 direction. Then, with the movement, the left/right pulley section 250 further moves in the arrow 31Y4 direction together with the left/right cam shaft 232, whereby the other surface of the left/right wire fixing pulley 251 abuts against the first friction plate 293.

As a result of the abutment of the other surface of the left/right wire fixing pulley 251 with the first friction plate 293 providing a change to an abutment state with a predetermined pressing force, rotation of the first friction plate 293 is transmitted to the left/right wire fixing pulley 251. As a result, the left/right wire fixing pulley 251 starts rotating in the arrow 31Y2 (arrow 29Y2 in FIG. 29) direction. Then, the left bending wire 213 fixed to the left/right wire fixing pulley 251 is pulled while the right bending wire 214 is slackened, whereby the bending portion 202b starts bending leftward.

Subsequently, the operator continues providing a force for rotating the left/right knob 205LR in the arrow 11Y1 direction. At this time, as described above, although the left/right knob 205LR and the left/right cam shaft 32 do not move, a pressing force of the other surface of the left/right wire fixing pulley 251 against the first friction plate 93 gradually increases. As a result, the rotation of the first friction plate 93 is transmitted to the pulley 251, whereby a rotational angle of the pulley 251 is changed. Then, the left bending wire 13 is further pulled, whereby the bending portion 202b becomes close to a maximal bending state.

Furthermore, in the case of an operation performed by an operator to bend the bending portion 202b rightward, the operator rotates the left/right knob 205LR illustrated in FIG. 29 in the arrow 9Y2 direction. Here, in FIG. 31D, the left/right knob 205LR rotates in the arrow 31Y2 direction, and with that rotation, the left/right cam shaft 232 moves in the arrow 31Y3 direction relative to the left/right cam shaft arrangement hole 203H2. As a result of the left/right cam shaft 232 moving in the arrow 31Y3 direction, the lid member 232C gradually approaches and then abuts against the left/right protrusion 254. The left/right knob 205LR is continuously rotated in the arrow 31Y2 direction even after the abutment, whereby the left/right cam shaft 232 is further moved in the arrow 31Y3 direction. Then, with the movement, the left/right pulley section 250 moves in the arrow 31Y3 direction together with the left/right cam shaft 232, whereby the one surface of the left/right wire fixing pulley 251 abuts against the second friction plate 294.

As a result of the abutment of the one surface of the left/right wire fixing pulley 251 with the second friction plate 294 providing a change to an abutment state with a predetermined pressing force, rotation of the second friction plate 294 is transmitted to the left/right wire fixing pulley 251. As a result, the left/right wire fixing pulley 251 starts rotating in the arrow 31Y1 (arrow 29Y1 in FIG. 29) direction. Then, the right bending wire 214 fixed to the left/right wire fixing pulley 251 is pulled while the left bending wire 213 is slackened, whereby the bending portion 202b starts bending rightward.

Subsequently, the operator continues providing a force for rotating the left/right knob 205LR in the arrow 31Y2 direction. Here, as described above, although the left/right knob 205LR and the left/right cam shaft 232 do not move, a pressing force of the one surface of the left/right wire fixing pulley 251 pressing the second friction plate 294 gradually increases. As a result, the rotation of the second friction plate 294 is transmitted to the pulley 251, whereby a rotational angle of the pulley 251 is changed, and consequently, the right bending wire 214 is further pulled, whereby the bending portion 202b becomes close to a maximal bending state.

In the above description, if the operator performs an operation to bend the bending portion 202b downward, leftward or rightward, the rotation operation strength amount increases in a stepwise manner with rotation. Then, after pulling of the bending wire 212, 213 or 214 is started, the rotation operation strength amount gradually increases as the bending angle of the bending portion 202b increases.

Here, an operation to bend the bending portion 202b of the endoscope 201A configured as described above will be described.

When an operator inserts the insertion portion 202 to a body from, e.g., an oral cavity, the operator drives the motor 210B in the operation portion 203 to bring the driven gears 291 and 292 and the friction plates 293 and 294 into a rotating state. Here, respective gaps are provided between the up/down wire fixing pulley 241 and the first friction plate 293, between the up/down wire fixing pulley 241 and the second friction plate 294, between the left/right wire fixing pulley 251 and the first friction plate 293, and between the left/right wire fixing pulley 251 and the second friction plate 294, and the bending portion 202b is in a straightened state.

The operator starts insertion of the insertion portion 202 into the body while observing an endoscopic image displayed on the screen of the non-illustrated observation apparatus.

First, in order to, for example, bend the bending portion 202b upward, as illustrated in FIG. 29, the operator rotates the up/down knob 205UD in the arrow 29Y1 direction. Then, with the rotation of the up/down knob 205UD, as described above, the rotation is transmitted, whereby the up/down wire fixing pulley 241 gradually approaches the second friction plate 294. At this time, while an amount of rotation of the up/down knob 205UD increases, the rotation operation strength amount increases in a stepwise manner.

Then, as a result of the up/down wire fixing pulley 241 abutting against the second friction plate 294, the rotation of the second friction plate 294 is transmitted to the pulley 241. As a result, a rotational angle of the up/down wire fixing pulley 241 starts changing.

Upon the rotational angle of the up/down wire fixing pulley 241 starts changing, the up bending wire 211 fixed to the pulley 241 is pulled with the change in the rotational angle of the pulley 241. As a result, the bending portion 202b starts bending upward. Subsequently, as a result of the up/down knob 205UD being continuously further rotated, a pressing force of the up/down wire fixing pulley 241 pressing the second friction plate 294 gradually increases, whereby the rotational angle of the pulley 241 increases. As a result, the up bending wire 211 is further pulled, whereby a bending angle of the bending portion 202b increases.

Note that, here, an amount of rotation operation strength for operating the up/down knob 205UD also gradually increases.

As a result of the operator continuously rotating the up/down knob 205UD, the angle of the rotation of the up/down wire fixing pulley 241 further increases, whereby the up bending wire 211 is further pulled. As a result, the bending portion 202b bends toward a maximal bending state.

On the other hand, if the operator holds the rotated state of the up/down knob 205UD during the operation for rotating the up/down knob 205UD, the second friction plate 294 enters a sliding state and the rotational angle of the up/down wire fixing pulley 241 is held. In other words, the bending angle of the bending portion 202b is held in the bent state.

In the present embodiment, during the up/down knob 205UD being rotated, for example, if the distal end portion 202a abuts against, e.g., a wall of a lumen, a bending operation of the bending portion 202b is interrupted by the wall. At this time, it may become impossible to pull the up bending wire 211. In this case, during a tilting operation to bend the bending portion 202b, an operator that is operating the endoscope 201A feels that as the bending angle increases, the amount of operation strength for operating the manipulator 205 increases, by pressure on his/her hand.

Thus, during the tilting operation, if an endoscopic image displayed on a screen of a display apparatus has no change despite an increase in amount of operation strength for tilting the manipulator 205, the operator can see a trouble in the bending portion such as the distal end portion 202a of the insertion portion 202 abutting against, e.g., a wall of a lumen.

As described above, with the endoscope 201A according to the present embodiment, the knob 205UD or 205LR provided in the operation portion 203 is rotated clockwise or counterclockwise. Then, the bending wire 211, 212, 213 or 214 corresponding to the operation is not directly pulled, but the wire fixing pulley 241 or 242 of the pulley section 240 or 250 corresponding to the rotation operation moves toward the friction plate 293 or 294. Then, the wire fixing pulley 241 or 242 abuts against the friction plate 293 or 294. Then, rotation of the friction plate 293 or 294 is transmitted to the pulley 241 or 242, whereby the pulley 241 or 242 rotates and thereby moves by a predetermined angle. As a result, the bending wire 211, 212, 213 or 214 corresponding to the rotation operation is pulled, whereby the bending portion 202b bends.

In this configuration, each of the rotation operation strength amounts for the knobs 205UD and 205LR is set in advance to be smaller than a strength amount for directly pulling the bending wire 211, 212, 213 or 214 by operating the knob 205UD or 205LR. Thus, a bending operation of the bending portion 202b can easily be performed by rotating the knob 205UD or 205LR provided at the operation portion 203.

Also, as described above, the amount of operation strength for rotating the knob 205UD or 205LR is set in advance to be smaller than an amount of strength for directly pulling the bending wire 211, 212, 213 or 214 by operating the knob 205UD or 205LR, and the configuration is provided so that as a rotation operation is performed to increase the bending angle of the bending portion 202b, the amount of strength for the rotation operation increases. Accordingly, during a tilting operation to bend the bending portion 202b, an operator senses a change in stress on the relevant bending wire 211, 212, 213 or 214 from an endoscopic image displayed on the display apparatus and a change in amount of tilting operation strength, enabling prevention of a trouble due to an abnormality in the bending of the bending portion 202b.

Note that the bending of the bending portion 202b bent by rotating the knob 205UD or 205LR gradually changes to be smaller by rotating the rotated knob 205UD or 205LR in the opposite direction. Then, when the knob 205UD or 205LR returns to an original state, the bending portion 202b restores to an original straightened state.

Figure 32:
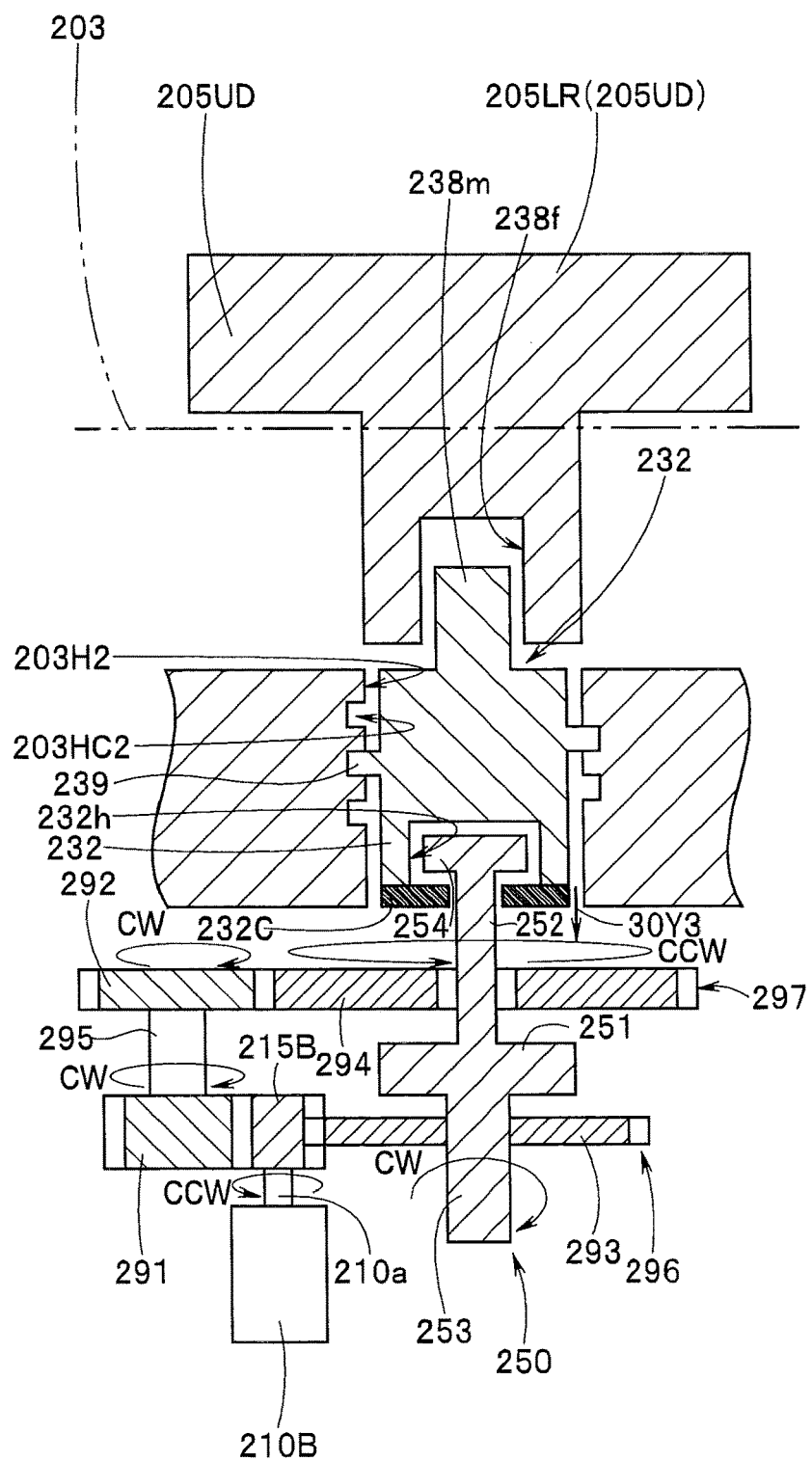
FIG. 32 is a diagram illustrating a configuration of an operation portion of an endoscope including a bending portion that bends in two directions.

Also, the above-described endoscope 201A is configured so that, in order to bend the bending portion 202b in four directions, i.e., upward, downward, leftward and rightward, the up/down knob 205UD and the left/right knob 205LR are arranged on an outer peripheral face of the operation portion body 203b. However, in the case of a configuration in which the bending portion 202b bends in two directions, i.e., upward and downward, as illustrated in FIG. 32, the above-described left/right knob 205LR is provided on the outer peripheral face of the operation portion 203 to use the left/right knob 205LR as an up/down knob.

In the present embodiment, inside the operation portion 203, the left/right shaft portion 205LRa integrated with the left/right knob 205LR, the left/right cam shaft 232, the left/right pulley section 250, the drive force transmission section 209A, the motor 210B, and the bending wires 211 and 212 (illustration omitted) are provided. Such configuration enables the bending portion 202b to bend in two directions, i.e., upward and downward by pivoting the left/right knob 205LR in a manner similar to the above.

Also, for a configuration in which the bending portion 202b is bent, for example, upward only, as illustrated in FIGS. 33 to 36B, an endoscope 201B is provided.

A configuration of the endoscope 201B, which is a modification of the present appendices, will be described with reference to FIGS. 33 to 36B.

Figure 33:
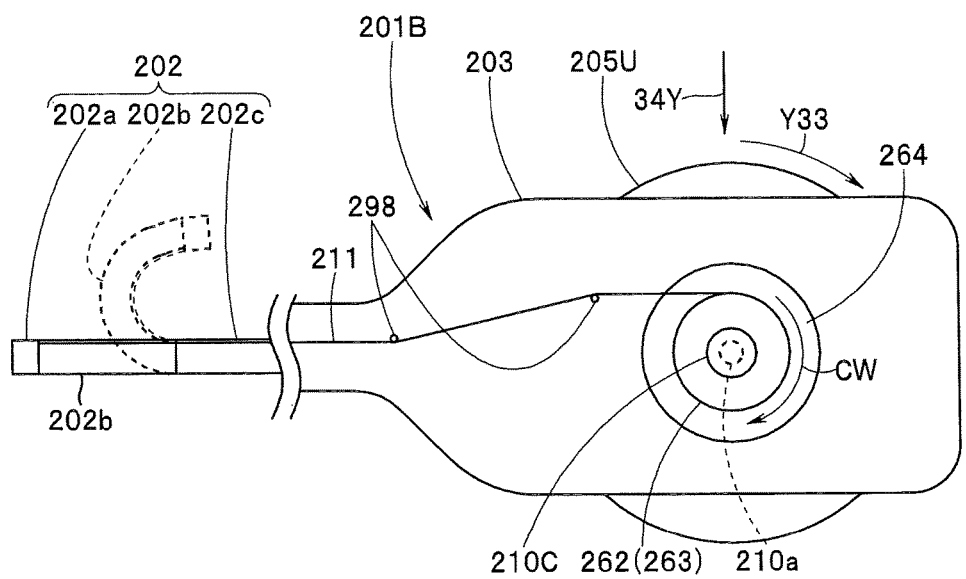
Figure 34:
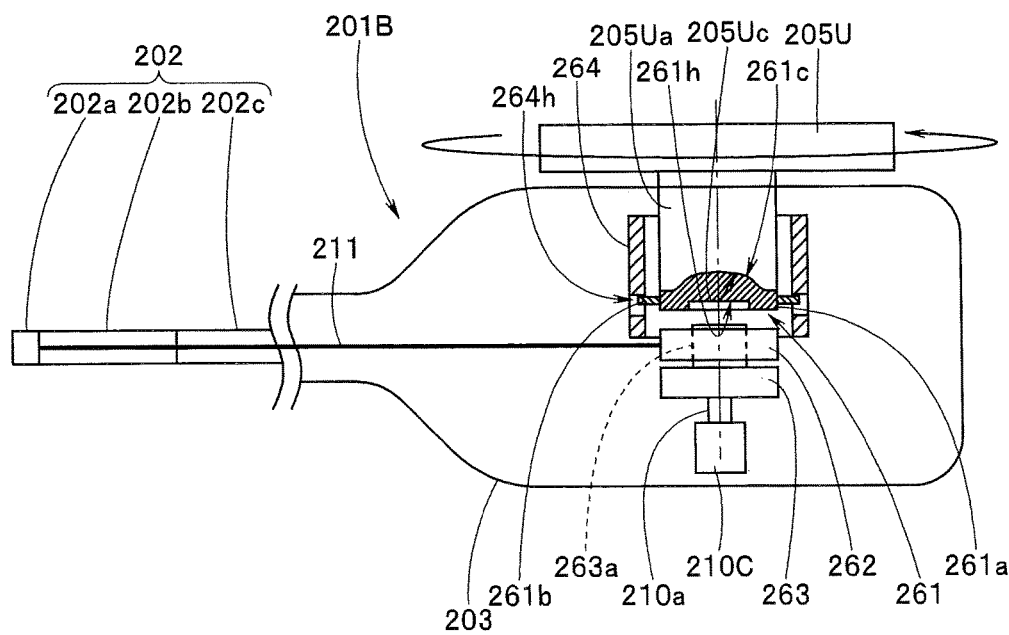
Figure 35A:
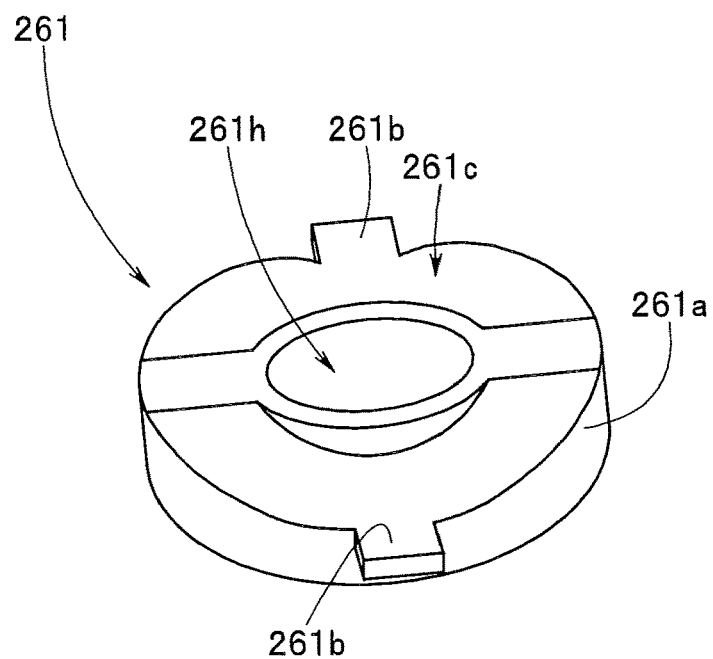
FIG. 35A is a diagram illustrating a pulley moving body including a cam receiving surface.
Figure 35B:
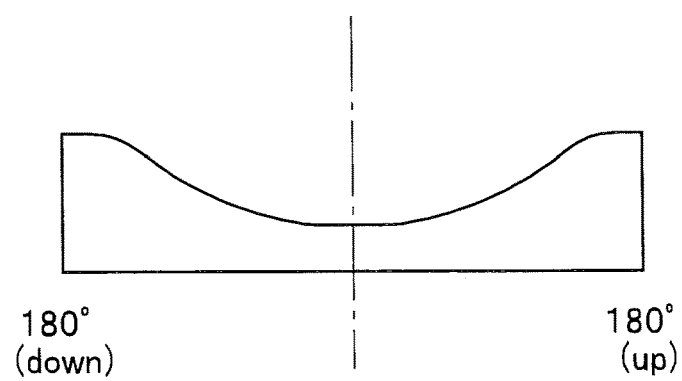
FIG. 35B is a cam diagram illustrating the cam receiving surface of the pulley moving body.
Figure 36A:
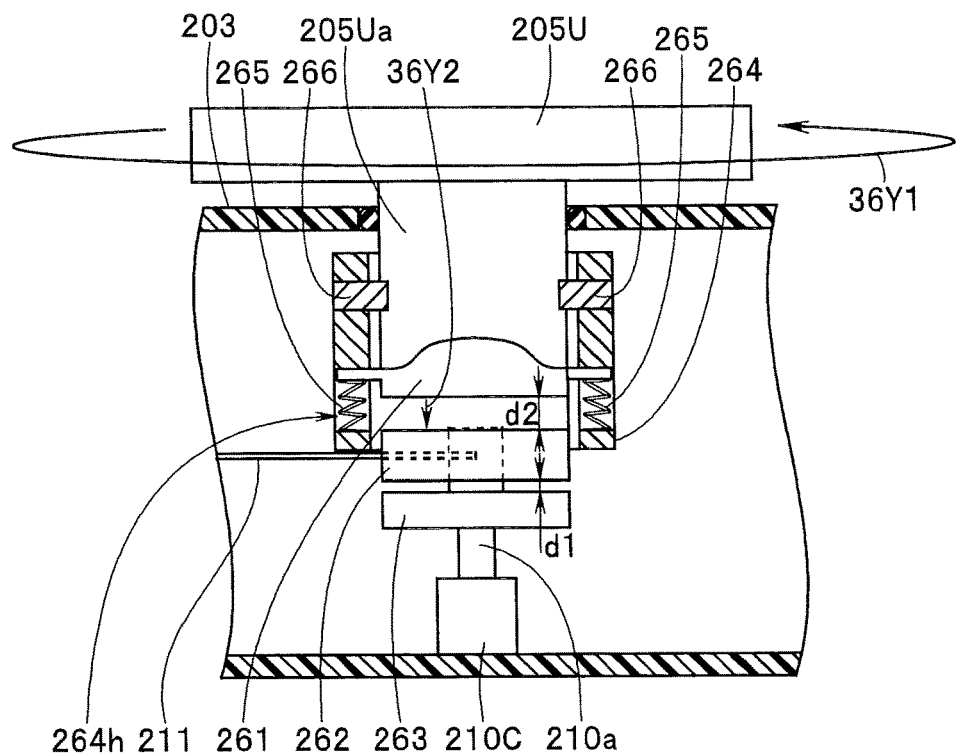
FIG. 36A is a diagram illustrating a relationship among the up pulley, the friction plate, the pulley moving body and the shaft portion of the operation dial when a bending portion is in a straightened state.
Figure 36B:
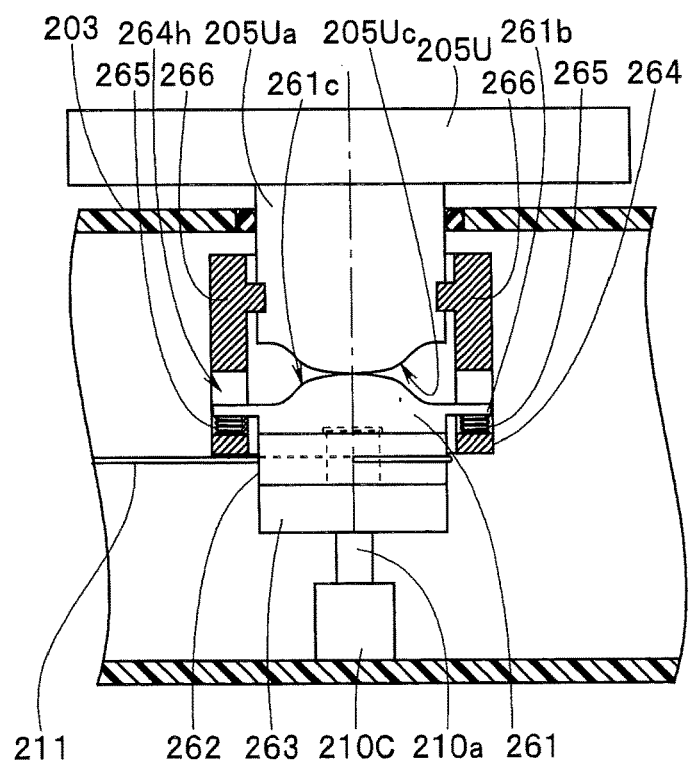
Figure 37:
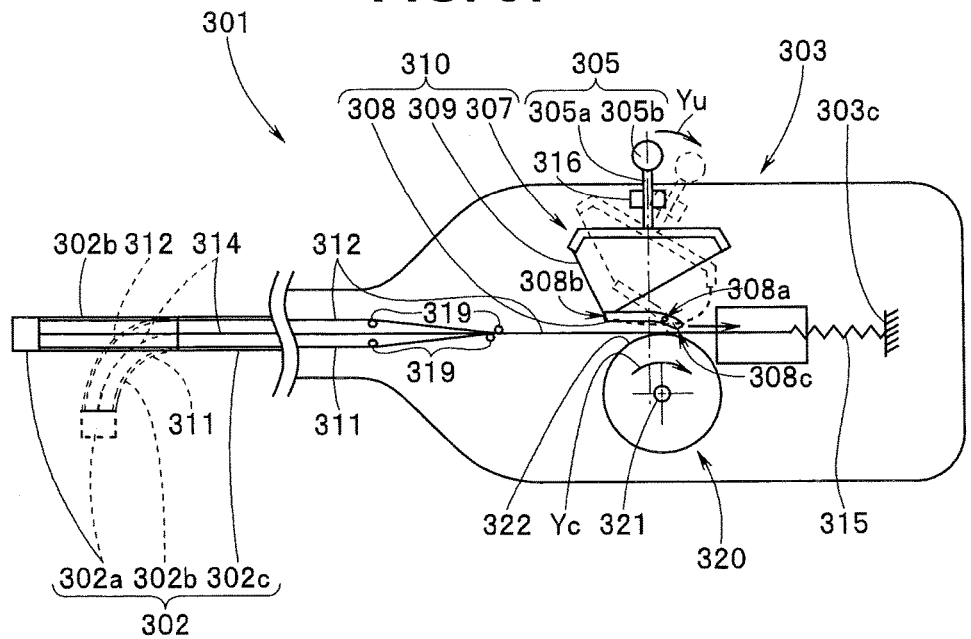
FIGS. 37 to 40 relate to a third embodiment of the appendices.

FIG. 33 is a side view illustrating a configuration of an endoscope, which is a diagram illustrating an endoscope including an operation dial included in an operation portion, and a pulley with an up bending wire fixed thereto, a friction plate and a pulley moving body provided in the operation portion; FIG. 34 is a diagram of the operation portion of the endoscope in FIG. 33 as viewed in an arrow 34Y direction, which is a diagram illustrating a relationship among the pulley with the up bending wire fixed thereto, the friction plate, the pulley moving body and a shaft portion of the operation dial; FIG. 35A is a diagram illustrating a pulley moving body including a cam receiving surface, FIG. 35B is a cam diagram illustrating the cam receiving surface of the pulley moving body; FIG. 36A is a diagram illustrating a relationship among the pulley, the friction plate, the pulley moving body and the shaft portion of the operation dial when a bending portion is in a straightened state; and FIG. 36B is a diagram illustrating a relationship among the pulley, the friction plate, the pulley moving body and the shaft portion of the operation dial when the bending portion is in a maximal bending state.

In the below description, members that are the same as those of the above-described embodiments are provided with reference numerals that are the same as those of the embodiments, and a description thereof will be omitted.

As illustrated in FIGS. 33 and 34, the endoscope 201B according to the present embodiment includes an upward bending knob (hereinafter abbreviated "up knob") 205U, which is an operation dial, arranged on an outer peripheral face of an operation portion 203. Inside the operation portion 203, a shaft portion 205Ua integrated with the up knob 205U, a pulley moving body 261, an up pulley 262, a friction plate 263, a motor 210C and an up bending wire 211 are mainly provided.

In the present embodiment, one end of the up bending wire 211 is fixed at a predetermined position on the distal end side of a bending portion 202b. The other end of the up bending wire 211 is fixed at a predetermined position on the up pulley 262. The up bending wire 211 is introduced to the inside of the operation portion 203, and then subjected to change in running route by guide rollers 298 and is tightened with a predetermined tensile force.

Also, the friction plate 263 is fixed to a motor shaft 210a of the motor 210C. The friction plate 263 is rotated clockwise by the motor 210C as illustrated in FIG. 33. Reference numeral 263a in FIG. 34 denotes a pulley holding shaft on which the up pulley 262 is slidably arranged. In the present embodiment, the motor 210C and the friction plate 263, which is directly rotated by the motor 210C, provide a drive section.

As illustrated in FIGS. 34 and 35A, the pulley moving body 261, which is a circular plate having a predetermined thickness dimension, includes a receiving body 261a, and for example, a pair of protrusions 261b, and a through hole 261h. A surface of the receiving body 261a includes a cam receiving surface 261c. The cam receiving surface 261c has a cam curve illustrated in FIG. 35B. The through hole 261h is a relief hole in which the pulley holding shaft 263a is received and thereby arranged. The pair of protrusions 261b, which are rotation prevention elements, project by a predetermined amount from an outer peripheral face of the receiving body 261a.

Note that another surface of the receiving body 261a is a pulley pressing surface, and includes, for example, two projection portions projecting from a flat surface. The two projection portions are arranged at equal intervals in a circumferential direction on the flat surface, and a distal end portion of each projection portion has a hemispherical shape. With this configuration, the up pulley 62 is pivotally held by the projection portions.

A distal end face of the shaft portion 205Ua is configured as a cam surface 205Uc corresponding to the cam receiving surface 261c of the pulley moving body 261.

As illustrated in FIG. 34, the shaft portion 205Ua and the receiving body 261a of the pulley moving body 261 are arranged inside a pipe-shaped frame 264. The frame 264 is fixedly provided inside the operation portion 203. The shaft portion 205Ua and the receiving body 261a are pivotable inside the frame 264. The protrusions 261b are slidably arranged in respective long holes 264h. The long holes 264h are formed in the frame 264. An axis of each long hole 264h is parallel to a center axis of the frame 264.

When the bending portion 202b is in a straightened state, as illustrated in FIG. 36A, a clearance d1 is formed between the friction plate 263 and the up pulley 262. The pulley moving body 261 is arranged inside the frame 264 in such a manner that a clearance d2 is formed between the up pulley 262 and the pulley moving body 261.

Note that reference numeral 265 denotes a spring. The spring 265 biases the pulley moving body 261 toward the up knob 205U to arrange the pulley moving body 261 at a predetermined position inside the frame 264. Reference numeral 266 denotes a locking pin. As a result of distal end portions of the locking pins 266 being arranged inside a circumferential groove 205Ug of the shaft portion 205Ua, the shaft portion 205Ua is held so that the shaft portion 205Ua pivots without moving in a frame axis direction inside the frame 264.

With the above-described configuration, when the up knob 205U is rotated in the arrow Y33 direction in FIG. 33, in FIG. 36A, the shaft portion 205Ua rotates in the arrow 36Y1 direction, which is the same direction as the above. Then, with the rotation of the shaft portion 205Ua, a position of the cam surface 205Uc relative to the cam receiving surface 261c changes. In other words, the cam surface 205Uc rotates and thereby moves on the cam receiving surface 261c. As a result, the pulley moving body 261 is moved in the arrow 36Y2 direction against a biasing force of the spring 265, whereby the pulley pressing surface abuts against the up pulley 262.

Then, an operator continues rotating the up knob 205U, whereby the pulley moving body 261 and the up pulley 262 integrally move in the arrow 36Y2 direction and the up pulley 62 abuts against the friction plate 263. As a result of the up pulley 262 abutting against the friction plate 263, rotation of the friction plate 263 is transmitted to the up pulley 262.

As a result, change in rotational angle of the up pulley 262 starts. Then, the up bending wire 211 fixed to the up pulley 262 is pulled with the change in rotational angle of the up pulley 262, and the bending portion 202b starts bending upward.

Subsequently, the operator further continuously rotates the up knob 205U, whereby a pressing force of pressing the up pulley 262 against the friction plate 63 is gradually increased. Then, the angle of rotation of the up pulley 262 further increases. Then, when the up knob 205U is made to reach a predetermined maximum rotation amount by the operator, as illustrated in FIG. 36B, the up pulley 262 reaches a maximum angle of rotation. At this time, the up bending wire 211 is pulled maximally and the bending portion 202b is bent maximally as indicated by dashed lines in FIG. 33.

As described above, with the endoscope 201B according to the present embodiment, an operation to rotate the up knob 205U provided at the operation portion 203 in a predetermined direction is performed. Then, the up bending wire 211 corresponding to such operation is not directly pulled, but the pulley moving body 261 is moved and then the pulley moving body 261 and the up pulley 262 integrally move toward the friction plate 263. Then, the up pulley 262 and the friction plate 263 abut against each other. Then, rotation of the friction plate 263 is transmitted to the up pulley 262, whereby the up pulley 262 rotates and thereby moves by a predetermined angle. As a result, the up bending wire 211 is pulled and the bending portion 202b bends upward.

In such configuration, a rotation operation strength amount for the up knob 205U is set in advance to be smaller than an amount of strength to directly pull the up bending wire 211 by operating the up knob 205U. Thus, a bending operation of the bending portion 202b can easily be performed by rotating the up knob 205U provided at the operation portion 203.

Also, as described above, the rotation operation strength amount for the up knob 205U is set in advance to be smaller than the amount of strength to directly pull the up bending wire 211 by operating the up knob 205U, and the configuration is provided so that as a rotation operation is performed to increase the bending angle of the bending portion 202b, the rotation operation strength amount increases. Accordingly, during a rotation operation to bend the bending portion 202b, an operator senses a change in stress on the up bending wire 211 from an endoscopic image displayed on a display apparatus and a change in rotation operation strength amount, enabling prevention of a trouble due to an abnormality in the bending of the bending portion 202b.

The first embodiment and the second embodiment of the present appendices, which have been described in detail above, provide a configuration as follows.

(5) An insertion apparatus comprising:
a bendable bending portion provided on a distal end side of an insertion portion extending from an operation portion;
pulling members provided so as to correspond to respective bending directions, each pulling member including an end fixed at a predetermined position on a distal end side of the bending portion, the end being moved toward a proximal end upon the pulling member being pulled, thereby bending the bending portion;
a rotating body on which other ends of the pulling members are fixed at respective predetermined positions;
a bending operation apparatus provided at the operation portion, the bending operation apparatus being operated to bend the bending portion; a drive section that generates a drive force for moving any of the pulling members; and
a drive force transmission section that transmits the drive force to the rotating body corresponding to the operation of the bending operation apparatus to provide a drive force transmission state to rotate the rotating body.

(6) The insertion apparatus according to appendix 5,
wherein the bending operation apparatus includes a rod-like manipulator that is tilted to bend the bending portion, and a suspension frame provided in the operation portion, the suspension frame being fixed integrally to the manipulator via a universal joint pivotally disposed in a frame and including frames corresponding to the respective bending directions of the bending portion, each frame including a pressing portion that presses and thereby moves the rotating body;

wherein the drive section includes a motor, a drive gear fixed to a motor shaft of the motor, and a plurality of driven gears provided so as to correspond to the respective bending directions of the bending portion, the plurality of driven gears being rotated by the drive gear in respective directions in which the respective pulling members are pulled; and wherein the drive force transmission section includes a force transmission adjustment section arranged between each driven gear and the rotating body to transmit rotation of the driven gear to the rotating body.

(7) The insertion apparatus according to appendix 6, wherein the force transmission adjustment section includes a disc spring.

(8) The insertion apparatus according to appendix 6 or 7, wherein a shaft corresponding to the bending directions of the bending portion is provided in the operation portion, and the driven gears provided so as to correspond to the bending directions of the bending portion and the rotating body, and the disc springs arranged between the driven gears and the rotating body are disposed on the shaft.

(9) The insertion apparatus according to appendix 5, wherein the bending operation apparatus includes a shaft portion coaxially fixed integrally to an operation dial that is rotated clockwise or counterclockwise to bend the bending portion, the shaft portion rotating integrally with the operation dial, and an instruction member that is advanced/retracted in an axis direction of the operation dial by rotation of the shaft portion; and wherein the drive section includes a motor, and a friction plate to be directly or indirectly rotated by the motor.

(10) The insertion apparatus according to appendix 9, wherein, in a configuration in which the bending directions of the bending portion include two directions opposed to each other, the drive section includes a motor, a drive gear fixed to a motor shaft of the motor, a first friction plate to be rotated by the drive gear, and a second friction plate to be rotated in a direction opposite to that of the first friction plate via a driven gear to be rotated by the drive gear, the rotating body includes a first shaft projecting from one surface side and a second shaft projecting from another surface side, and the drive force transmission section includes a protrusion portion at an end portion of the first shaft, a hole that is provided in the instruction member and receives the protrusion portion, and a lid member that occludes the hole portion, includes an opening through which the first shaft is inserted and abuts against the protrusion portion.

(11) The insertion apparatus according to appendix 10, wherein in an endoscope in which the bending directions of the bending portion include four directions, the endoscope having a configuration further including an additional operation dial, an additional instruction member and an additional rotating body, in which a shaft of one of the operation dials and a shaft of the other operation dial are coaxially arranged and one of the two instruction members and one of the two rotating bodies are arranged coaxially with the shafts of the two operation dials, and the other of the two instruction members and the other of the two rotating bodies are arranged on an axis that is different from those of the shafts of the two operation dials, the endoscope further includes a transmission mechanism section that transmits rotation of the shaft of the operation dial arranged on an outer side from among the two operation dials to the instruction member arranged on the axis that is different from those of the shafts of the two operation dials.

(12) The endoscope according to appendix 9, wherein in a configuration in which the bending direction of the bending portion is one direction, the drive section includes a motor, a friction plate fixed to a motor shaft of the motor; and the bending operation apparatus includes a shaft portion that rotates integrally with the operation dial, and a receiving member that is advanced/retracted by rotation of the shaft portion in the axis direction of the operation dial and doubles as a power transmission section that moves the rotating body.

(13) An insertion apparatus device comprising:

a bendable bending portion provided on a distal end side of an insertion portion extending from an operation portion;

a pulling member provided so as to correspond to a bending direction, the pulling member including an end fixed at a predetermined position on a distal end side of the bending portion, the end being moved toward a proximal end upon the pulling member being pulled, thereby bending the bending portion;

a rotating body on which another end of the pulling member is fixed at a predetermined position;

a bending operation apparatus provided at the operation portion, the bending operation apparatus being operated to bend the bending portion; a drive section that generates a drive force for moving the pulling member; and a drive force transmission section that transmits the drive force to the rotating body corresponding to the operation of the bending operation apparatus to provide a drive force transmission state to rotate the rotating body.

A third embodiment of the present appendices will be described with reference to FIGS. 38 to 41.

Figure 38:
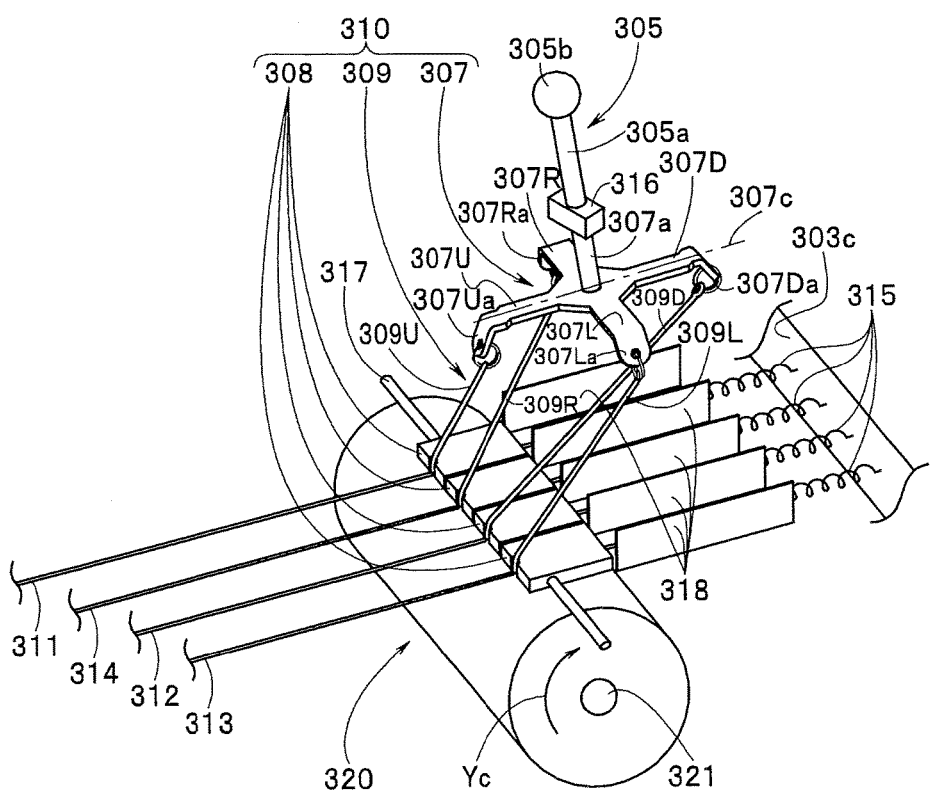
Figure 39:
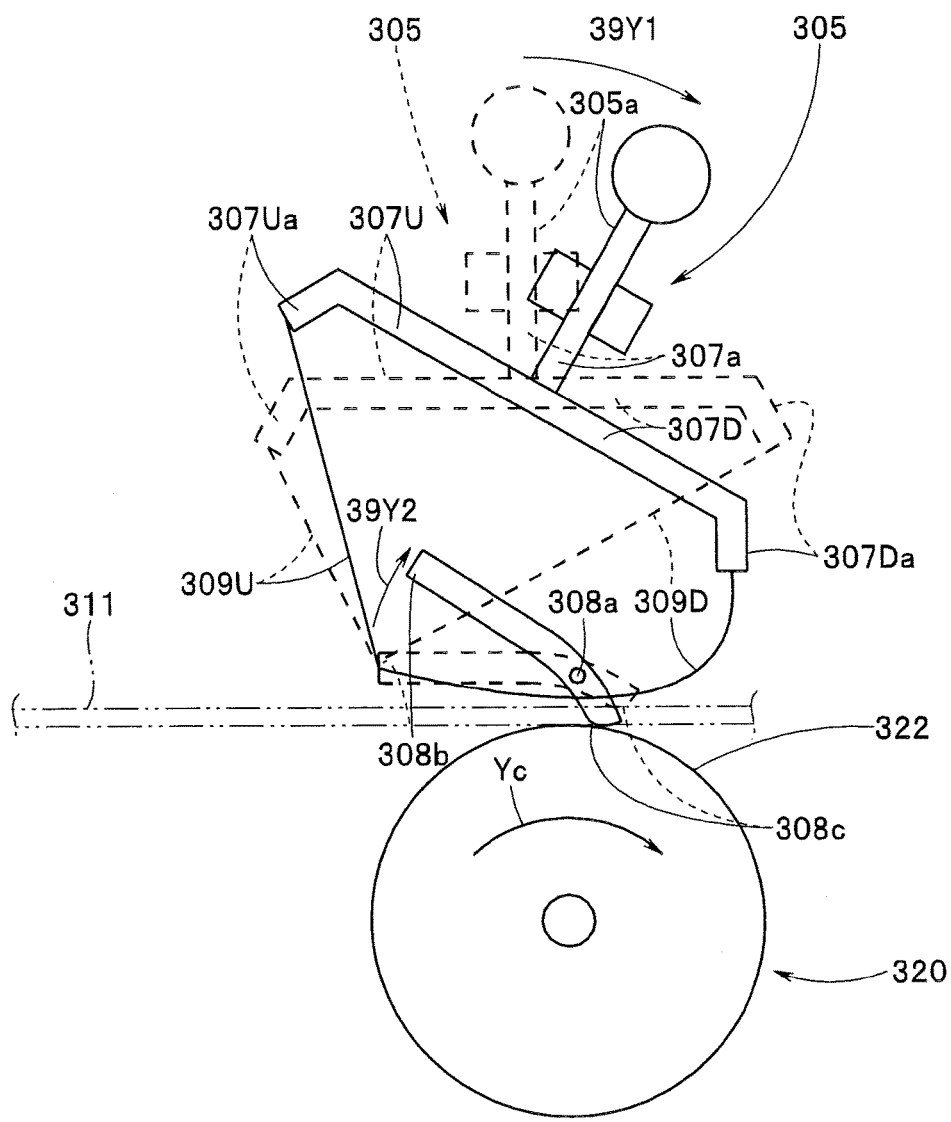

As illustrated in FIGS. 38 and 39, inside an operation portion 303, a shaft portion 305a of a manipulator 305, a drive force transmission section 310, bending wires 311, 312, 313 and 314, which are pulling members, and a pulley 320 are mainly provided.

The pulley 320, which is included in a drive section, is a rotating body. The pulley 320 is disposed inside the operation portion 303, and is rotated clockwise as indicated by arrow Yc in the Figure. A pulley shaft 321 of the pulley 320 is arranged sideways in a positional relationship in which the pulley shaft 321 is substantially immediately below a shaft portion 305a of the manipulator 305 and perpendicular to a longitudinal axis of the operation portion 303. An outer peripheral face 322 of the pulley 320 provides a pulling member moving surface. The pulley 320 transmits a rotation drive force of the pulley 320 to the bending wires 311, 312, 313 and 314 that are in contact with the outer peripheral face 322.

As illustrated in FIG. 38, when the manipulator 305 is, for example, at an upright position, the pulley shaft 321 of the pulley 320 is arranged in the vicinity of an extension of a center axis of the shaft portion 305a.

The pulley 320 illustrated in FIGS. 38 and 39 is rotated by a motor (not illustrated), which is included in a drive apparatus. In the present embodiment, a motor shaft of the motor is arranged in parallel to the longitudinal axis of the operation portion 303. A motor-side bevel wheel (not illustrated) is provided on the motor shaft, and on the pulley shaft 321, a pulley-side bevel wheel (not illustrated), which engages with the motor-side bevel wheel, is provided.

Then, the pulley 320 enters a state of rotating clockwise as a result of rotation of the motor shaft being transmitted from the motor-side bevel wheel to the pulley-side bevel wheel.

The bending wires 311, 312, 313 and 314, which are wires corresponding to four bending directions of a bending portion 302b, are an up bending wire 311, a down bending wire 312, a left bending wire 313 and a right bending wire 314.

One end of each bending wire 311, 312, 313 or 314 is fixed at a predetermined position on the distal end side of the bending portion 302b. On the other hand, the other end of each bending wire 311, 312, 313 or 314 is fixed to the one end side of a coil spring 315. The coil spring 315 is a slack removal mechanism and has a predetermined spring constant. The coil springs 315 are provided one by one for the respective bending wires 311, 312, 313 and 314. The other ends of the coil springs 315 corresponding to the respective bending wires 311, 312, 313 and 314 are fixed in alignment to a partition wall 303c provided inside the operation portion 303.

The respective bending wires 311, 312, 313 and 314 are introduced to the inside of the operation portion 303, and then subjected to change in respective running routes by, for example, a plurality of guide rollers 319 and pass in the vicinity of the outer peripheral face 322 on the manipulator 305 side of the pulley 320 in a positional relationship in which the bending wires 311, 312, 313 and 314 are perpendicular to the pulley shaft 321. When the bending portion 302b is in a straightened state, the respective bending wires 311, 312, 313 and 314 are tightened with a predetermined tensile force, and are located close to or abut against the outer peripheral face 322.

When the bending portion 302b is in a straightened state, each coil spring 315 is expanded within an elasticity range. Then, when the bending portion 302b is bent upward as indicated by dashed lines in FIG. 38, the coil spring 315 with the up bending wire 311 fixed thereto contracts relative to the original expanded state within the elasticity range. The coil spring 315 with the down bending wire 312, which is opposed to the up bending wire 311, fixed thereto further expands relative to the original expanded state within the elasticity range. On the other hand, the coil spring 315 with the left bending wire 313 fixed thereto and the coil spring 315 with the right bending wire 314 fixed thereto are in a state that is substantially the same as the original expanded state.

The drive force transmission section 310 includes a suspension frame 307, pressing plates 308, and operation input transmission wires 309U, 309D, 309L and 309R.

As illustrated in FIG. 39, the suspension frame 307 includes four frames 307U, 307D, 307L and 307R and is formed in a substantial cruciform. The four frames 307U, 307D, 307L and 307R correspond to bending directions of the bending portion 302b, i.e., upward, downward, leftward and rightward, respectively. The suspension frame 307 includes a frame shaft 307a, which is a center shaft portion, provided in a standing manner. The shaft portion 305a of the manipulator 305 and the frame shaft 307a of the suspension frame 307 are coaxially attached and fixed to each other via a universal joint 316.

The universal joint 316 is pivotally disposed on a non-illustrated frame provided inside the operation portion 303. The suspension frame 307 configured as described above swings with tilting of the manipulator 305.

The up frame 307U and the down frame 307D are arranged in a straight line across the frame shaft 307a. An up operation input transmission wire attachment portion 7Ua is provided at an end portion of the up frame 307U. A down operation input transmission wire attachment portion 7Da is provided at an end portion of the down frame 307D. On the other hand, the left frame 307L and the right frame 307R are perpendicular to an up/down frame center line 307c and arranged in a straight line across the frame shaft 307a. A left operation input transmission wire attachment portion 307La is provided at an end portion of the left frame 307L. A right operation input transmission wire attachment portion 307Ra is provided at an end portion of the right frame 307R.

The pressing plates 308 are members for pressing the respective bending wires 311, 312, 313 and 314 against the outer peripheral face 322 of the pulley 320. The pressing plates 308 are provided one by one for the four bending wires 311, 312, 313 and 314. The four pressing plates 308 are pivotally disposed on a pressing plate shaft 317 fixed to a non-illustrated frame provided inside the operation portion 303. The pressing plate shaft 317 is arranged in parallel to the pulley shaft 321.

The pressing plate 308 is, for example, a plate member of a metal. Each pressing plate 308 includes a shaft hole 308a, a joining portion 308b and a contact surface 308c. The shaft hole 308a is formed at a predetermined position between the joining portion 308b and the contact surface 308c. The shaft hole 308a is a through hole through which the pressing plate shaft 317 is inserted.

In the respective joining portions 308b, distal ends that are one ends of the respective operation input transmission wires 309U, 309D, 309L and 309R are fixedly provided. A proximal end that is the other end of the up operation input transmission wire 309U is attached to the up operation input transmission wire attachment portion 307Ua. Likewise, the other end portion of the down operation input transmission wire 309D is attached to the down operation input transmission wire attachment portion 307Da, the other end portion of the left operation input transmission wire 309L is attached to the left operation input transmission wire attachment portion 307La, and the other end portion of the right operation input transmission wire 309R is attached to the right operation input transmission wire attachment portion 307Ra.

The contact surfaces 308c are arranged so as to face the outer peripheral face 322 across the respective bending wires 311, 312, 313 and 314 that pass in the vicinity of the outer peripheral face 322.

With these configurations, for example, an operator tilts the manipulator 305, whereby the suspension frame 307 swings. For example, if the operator tilts the manipulator 305 in the arrow Yu direction, the up operation input transmission wire 309U corresponding to a direction of the swinging from among the operation input transmission wires 309U, 309D, 309L and 309R is pulled.

When the up operation input transmission wire 309U is pulled, the pressing plate 308 with the distal end of the wire 309U fixed thereto is rotated about the pressing plate shaft 317. With the rotation of the pressing plate 308, the relevant contact surface 308c comes into contact with the up bending wire 311. Subsequently, as an angle of the tilting of the manipulator 305 increases, the contact surface 308c presses the up bending wire 311 against the outer peripheral face 322.

If the up bending wire 311 is pressed against the outer peripheral face 322 of the pulley 320 by the contact surface 308c, frictional resistance is generated between the outer peripheral face 322 and the up bending wire 311. With the generation of the frictional resistance, a rotation drive force of the pulley 320 is transmitted to the up bending wire 311 via the outer peripheral face 322.

As a result, the up bending wire 311 is moved in a direction of the rotation of the pulley 320 according to a magnitude of the frictional resistance. In other words, the rotation drive force transmitted from the outer peripheral face 322 of the pulley 320 to the up bending wire 311 starts pulling of the up bending wire 311, whereby the bending portion 302b bends.

As the angle of tilting of the manipulator 305 increases, the pressing force of the contact surface 308c pressing the up bending wire 311 against the outer peripheral face 322 increases, whereby the bending portion 302b further bends. Then, as the angle of tilting of the manipulator 305 reaches a predetermined angle, the tilting of the manipulator 305 is halted. Here, if the operator continues increasing the amount of operation strength put on the manipulator 305, the pressing force of the contact surface 308c pressing the up bending wire 311 against the outer peripheral face 322 increases. As a result, the up bending wire 311 is further pulled by the rotation drive force transmitted from the outer peripheral face 322, whereby the bending portion 302b bends upward at a maximal bending angle.

In the present embodiment, the operation strength amount for tilting the manipulator 305 increases as the bending angle of the bending portion 302b increases after the bending wire 311, 312, 313 or 314 is brought into contact with the outer peripheral face 322 by the corresponding contact surface 308c. In other words, an amount of the contact surface 308c pressing the bending wire 311, 312, 313, or 314 against the outer peripheral face 322 increases with an increase in amount of strength for operating the manipulator 305.

Then, in the present embodiment, a maximum amount of strength for operating the manipulator 305, that is, an amount of strength for performing a tilting operation to bend the bending portion 302b maximally is set to a predetermined value. The value is a strength amount that is smaller than an operation strength amount for directly pulling the bending wire 311, 312, 313 or 314 by tilting the manipulator 305.

Note that the tilting operation strength amount can be set to a desired value by arbitrarily setting lengths of the respective frames 307U, 307D, 307L and 307R, lengths of the pressing plates 308, positions of the shaft holes 308a and stiffness of the operation input transmission wires 309U, 309D, 309L and 309R.

Also, the operation input transmission wires 309U, 309D, 309L and 309R, the suspension frame 307 and the pressing plate 308 each have predetermined stiffness. As a result, as described above, when the manipulator 305 reaches the predetermined tilting angle, the manipulator 305 is halted without being further tilted.

Also, the operation input transmission wires 309U, 309D, 309L and 309R are tightened with a predetermined tensile force. As a result, when the manipulator 305 is tilted, an operation input transmission wire according to a direction of the tilting from among the operation input transmission wires 309U, 309D, 309L and 309R is instantly pulled. Then, the respective operation input transmission wires 309U, 309D, 309L and 309R are joined to the respective wire attachment portions 307Ua, 307Da, 307La and 307Ra of the suspension frame 307 and also to the joining portions 308b of the respective pressing plates 308 directly or with respective running routes changed by non-illustrated guide rollers.

Reference numeral 318 denotes a partition plate. The partition plates 318 are provided to prevent contact between the coil springs 315 arranged adjacent to one another and contact between the bending wires 311, 312, 313 and 314 connected to the respective coil springs 315. Although the illustration is omitted, a configuration in which partition members that prevent contact between the pressing plates 308 are provided among the respective pressing plates 308 or a configuration in which the partition plates 318 are provided with respective pressing plate partition portions may be employed.

Here, an operation to bend the bending portion 302b of the endoscope 301 configured as described above will be described.

When an operator inserts the insertion portion 302 to a body from, for example, an oral cavity, the operator drives the motor inside the operation portion 303 to rotate the pulley 320. The operator starts inserting the insertion portion 302 into the body while observing an endoscopic image displayed on a screen of a non-illustrated observation apparatus.

Figure 40:
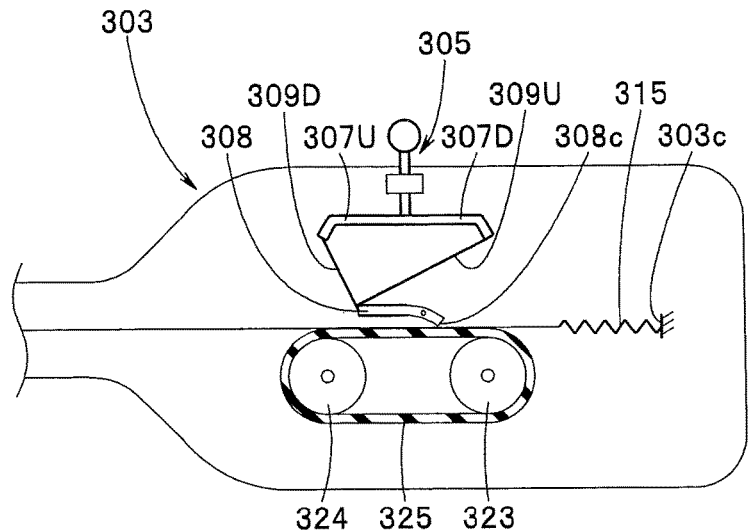

Next, in order to, for example, bend the bending portion 302b upward, as illustrated in FIG. 40, the operator tilts the manipulator 305 in the arrow 40Y1 direction. Then, the manipulator 305 and the suspension frame 307 integrally move in a same direction.

As a result, the down operation input transmission wire attachment portion 307Da of the suspension frame 307 moves toward the pulley 320. On the other hand, the up operation input transmission wire attachment portion 307Ua moves in a direction away from the pulley 320. Then, from among the operation input transmission wires 309U, 309D, 309L and 309R tightened with the predetermined tensile force, the up operation input transmission wire 309U corresponding to the tilting operation is gradually pulled, and the down operation input transmission wire 309D is gradually slackened.

With the pulling of the up operation input transmission wire 309U, as described above, the corresponding pressing plate 308 is rotated in the arrow 40Y2 direction about the shaft hole 308a, whereby the contact surface 308c comes into contact with the up bending wire 311. Subsequently, as a result of the manipulator 305 being tilted, the pressing plate 308 is further rotated in the same direction by the pulling of the up operation input transmission wire 309U. As a result, the contact surface 308c presses the up bending wire 311 against the outer peripheral face 322 of the rotating pulley 320. An amount of the pressing force at this time corresponds to an amount of operation strength for tilting the manipulator 305.

Upon the up bending wire 311 coming into contact with the outer peripheral face 322 of the pulley 320, friction occurs between the outer peripheral face 322 and the up bending wire 311. The up bending wire 311 is moved in the direction of the rotation of the pulley 320 by the generated frictional resistance, whereby the bending portion 302b bends upward. At this time, an amount of movement of the up bending wire 311 is proportional to frictional resistance generated between the up bending wire 311 and the contact surface 308c, in other words, is proportional to the force of pressing the outer peripheral face 322.

Then, if the operator further tilts the manipulator 305 in the 40Y1 direction, the pressing force applied from the contact surface 308c to the up bending wire 311 increases and thus, the up bending wire 311 is further pulled, whereby the bending portion 302b further bends upward. On the other hand, if the operator holds the position of the titled manipulator 305, the bending portion 302b is held in the state of bending at that bending angle.

Also, during titling of the manipulator 305 in the 40Y1 direction being continued, if the distal end portion 302a abuts, e.g., a wall of a lumen, the bending operation of the bending portion 302b is interrupted by the wall. In this case, for example, it may become impossible to pull the up bending wire 311. In the endoscope 301 according to the present embodiment, during a tilting operation to increase a bending angle of the bending portion 302b, an amount of operation strength put on the manipulator 305 increases as the bending angle increases.

Accordingly, during a manipulator operation, if an endoscopic image displayed on a screen of a display apparatus has no change despite an increase in amount of operation strength to operate the manipulator 305, a surgeon can see a trouble in the bending portion such as the distal end portion 2a of the insertion portion 302 abutting against, e.g., a wall of a lumen.

As described above, with the endoscope 301 according to the present embodiment, the manipulator 305 provided at the operation portion 303 is tilted, whereby the drive force transmission section 310 is swung without the bending wires 311, 312, 313 and 314 being directly pulled. Upon the drive force transmission section 310 being swung, the corresponding pressing plate 308 is rotated about the pressing plate shaft 317 and thereby presses the bending wire 311, 312, 313 or 314 corresponding to the instruction to tilt the manipulator 305 against the outer peripheral face 322 of the pulley 320. As a result, the pressed bending wire 311, 312, 313 or 314 is moved in a direction of the rotation of the pulley 320 by frictional resistance generated at this time and thereby bends the bending portion 302b.

In this configuration, an amount of tilting operation strength on the manipulator 305 is set in advance to be smaller than an amount of strength for directly pulling the bending wire 311, 312, 313 or 314 by tilting the manipulator 305. Thus, a bending operation of the bending portion 302b can easily be performed by tilting the manipulator 305 provided at the operation portion 303.

Note that the bending portion 302b bent by tilting the manipulator 305 restores to a straightened state by an elastic repellent force the bending portion 302b has, by returning the manipulator 305 to an upright position.

Figure 41:
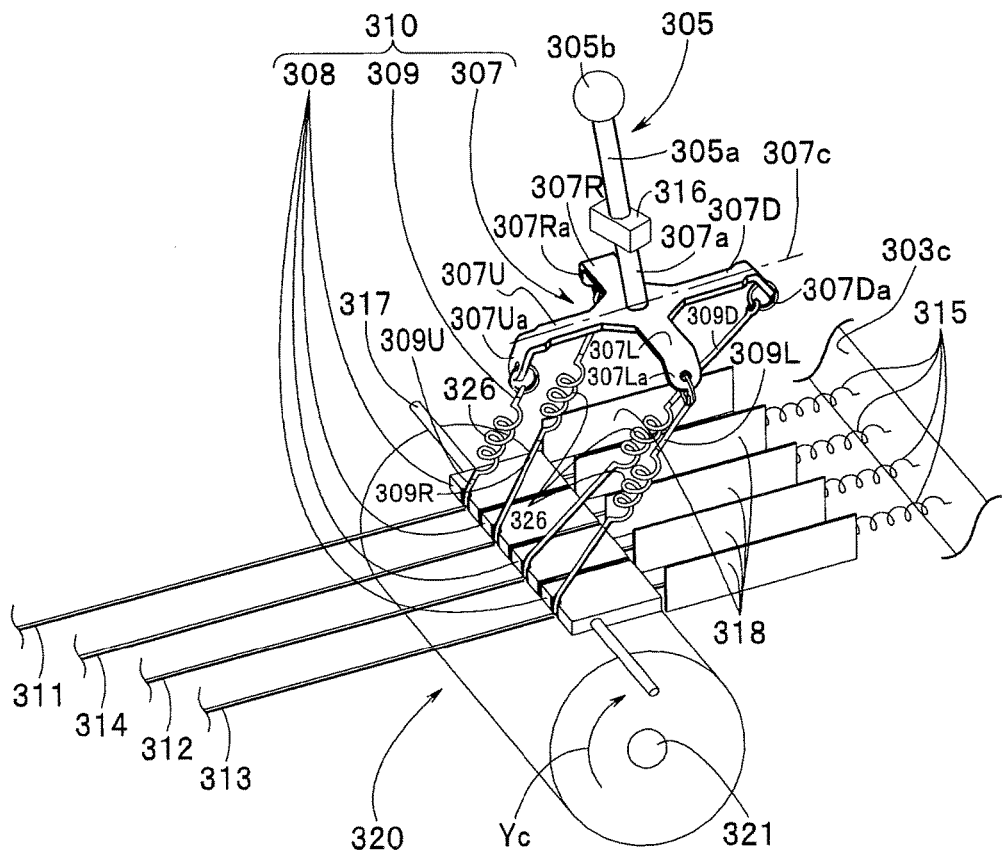
FIG. 41 is a diagram illustrating a configuration in which a coil spring is provided partway of each operation input transmission wire.

Also, in the above-described embodiment, it is assumed that the outer peripheral face 322 provides a pulling member moving surface of the pulley 320. However, the pulling member moving surface is not limited to the outer peripheral face 322 of the pulley 320, and a surface of a belt 325 illustrated in FIG. 41 may be used as a pulling member moving surface. As illustrated in FIG. 41, inside the operation portion 303, for example, a drive pulley 323, a driven pulley 324 and a belt 325 looped around the pulleys 323 and 324 to serve as a rotating body are provided. This configuration enables operations and effects similar to the above to be provided by pressing the bending wire 311, 312, 313 or 314 against the surface of the belt 325 by the contact surface 308c of the pressing plate 308.

Figure 42:
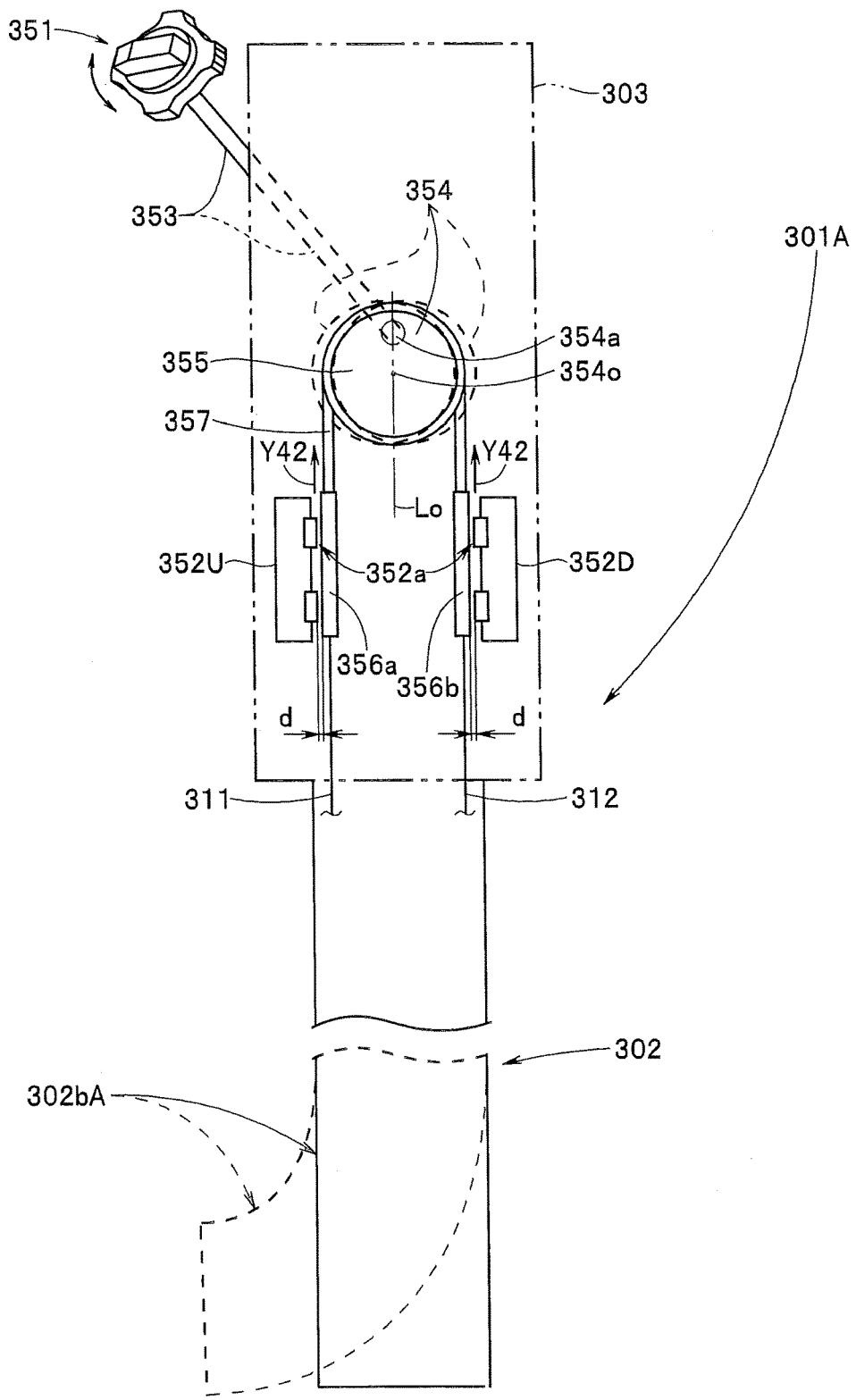
FIGS. 42 and 43 relate to a fourth embodiment of the appendices.

Also, in the above-described embodiment, when the manipulator 305 reaches a predetermined tilting angle, the tilting operation is halted. However, as illustrated in FIG. 42, for example, coil springs 326 for tilting operation having a predetermined spring constant may be provided in respective positions partway of the operation input transmission wires 309U, 309D, 309L and 309R.

With this configuration, during an operation to tilt the manipulator 305, after the manipulator 305 reaches a predetermined tilting angle, the manipulator 305 can continuously be tilted without the tilting operation being halted. At this time, the relevant coil spring 326 for tilting operation expands with the tilting of the manipulator 305. As a result, the amount of operation strength for operating the manipulator 305 increases. In other words, as a result of the coil springs 326 for tilting operation being provided in the respective positions partway of the operation input transmission wires 309U, 309D, 309L and 309R, a configuration in which as an angle of titling of the manipulator 305 increases, the tilting operation strength amount and the pressing force amount increase can be provided.

A fourth embodiment of the present appendices will be described with reference to FIGS. 43 and 44.

Figure 43:
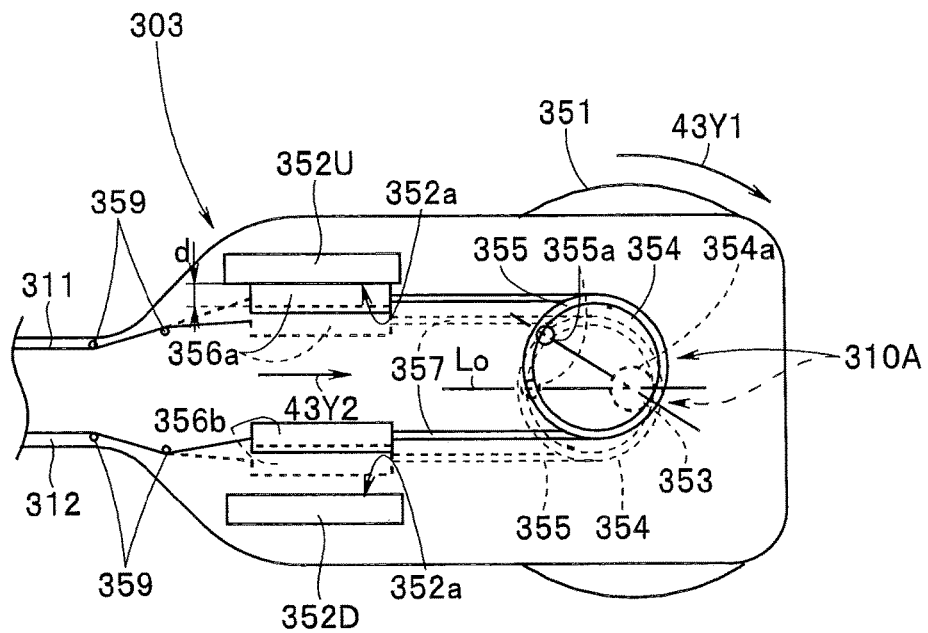
Figure 44:
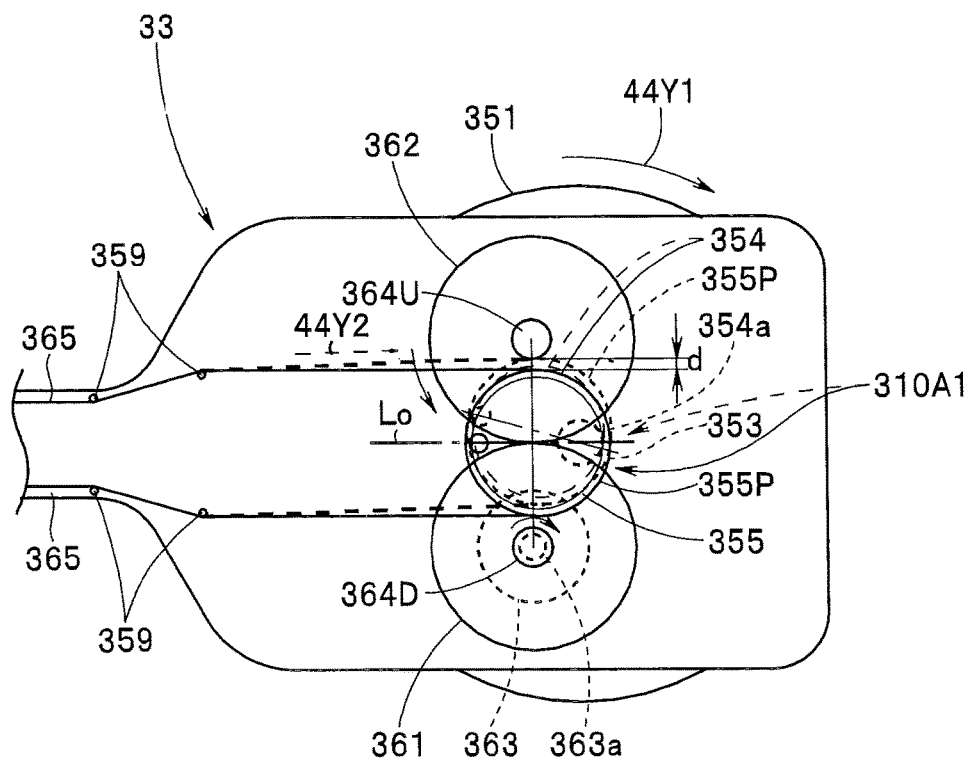
FIG. 44 is a diagram illustrating another example configuration of a drive section.

FIG. 43 is a diagram illustrating an endoscope including an operation dial, which provides a bending operation apparatus, at an operation portion, and FIG. 44 is a diagram illustrating a relationship among the operation dial, a drive force transmission section and an ultrasound motor.

As illustrated in FIG. 43, an endoscope 301A according to the present embodiment includes an operation dial 351, which is what is called a bending operation knob, instead of the manipulator 305. Then, the operation portion 303 includes a pair of ultrasound motors 352 as a drive section, instead of the pulley 320. Then, as illustrated in FIG. 44, a drive force transmission section 310A includes a shaft body 353, a fixing plate 354, a sprocket 355 and sliding members 356.

In the present embodiment, a bending portion 302bA bends in two directions, i.e., upward and downward. The rest of the configuration is similar to that of the above-described third embodiment, and members that are the same as those of the third embodiment are provided with reference numerals that are the same as those of the third embodiment and a description thereof will be omitted.

The operation dial 351 is a bending operation apparatus that can be rotated. An instruction for bending operation is provided by rotating the operation dial 351 clockwise or counterclockwise about an axis. The bending portion 302bA bends upward or downward by a desired angle by rotating the operation dial 351. The operation dial 351 is provided at a side face of the operation portion 303 so that the operation dial 351 can be made to pivot via, e.g. a thumb.

Inside the operation portion 303, the shaft body 353, the fixing plate 354, the sprocket 355, the pair of sliding members 356, bending wires 311 and 312 and the pair of ultrasound motors 352U and 352D are mainly provided. The ultrasound motors 352U and 352D are drive apparatuses. Each ultrasound motor 352 includes a vibrating surface 352a, which is a pulling member moving surface that generates ultrasound vibration. The respective vibrating surfaces 352a of the ultrasound motors 352U and 352D generate a straight advancement drive force for making the later-described sliding members 356a and 356b advance straight, respectively, in the arrow Y43 direction.

The shaft body 353 is, for example, a round rod that is made of a metal and has predetermined stiffness. One end face of the shaft body 353 is fixed integrally to a non-illustrated back face of the operation dial 351. As a result, the shaft body 353 rotates upon the operation dial 351 being rotated.

The fixing plate 354 is configured by a pair of, for example, circular plates that are made of a metal and have predetermined stiffness. The fixing plate 354 serves as both a holding plate that holds the sprocket 355 and an attachment plate to which the other end face of the shaft body 353 is fixed integrally.

The other end face of the shaft body 353 is fixed at a position that is different from a center 354o of one of the circular plates of the fixing plate 354, that is, an eccentric position on a shaft body fixing portion 354a. In the present embodiment, the shaft body fixing portion 354a is provided in a direction opposite to the insertion portion 302 across the center 354o.

With this configuration, the operation dial 351 is rotated, whereby the shaft body 353 rotates integrally with the operation dial 351. Then, with this rotation, the fixing plate 354 pivots about the shaft body fixing portion 354a together with the sprocket 355 as indicated by dashed lines. In other words, the fixing plate 354 swings upward and downward in the Figure as indicated by dashed lines across a reference line Lo parallel to a longitudinal axis of the operation portion that passes the center 354o.

A center of the sprocket 355 is coaxial to a center of the fixing plate 354. The sprocket 355 is a rotating body. The sprocket 355 is pivotally arranged between the pair of circular plates included in the fixing plate 354. A chain 357 engages with the sprocket 355. One end side of the chain 357 is attached to the proximal end side of the first sliding member 356a, and the other end side is attached to the proximal end side of the second sliding member 356b. A proximal end portion of the up bending wire 311 is fixed to the distal end side of the first sliding member 356a, and a proximal end portion of the down bending wire 312 is fixed to the distal end side of the second sliding member 356b.

The respective bending wires 311 and 312 are introduced to the inside of the operation portion 303, and then respective running routes of the bending wires 311 and 312 are changed by a plurality of guide rollers (reference numeral 359 in FIG. 44). In the present embodiment, the up bending wire 311 and the down bending wire 312 are arranged so as to run inside the operation portion 303 in a positional relationship in which the up bending wire 311 and the down bending wire 312 are parallel to each other.

The respective bending wires 311 and 312 are tightened with a predetermined tensile force when the bending portion 302b is in a straightened state indicated by solid lines. Here, as illustrated in FIG. 43, a predetermined clearance d is formed between the vibrating surface 352a of the first ultrasound motor 352U and the first sliding member 356a, and also between the vibrating surface 352a of the second ultrasound motor 352D and the second sliding member 356b.

The vibrating surface 352a of the first ultrasound motor 352U and the vibrating surface 352a of the second ultrasound motor 352D are arranged to face each other.

An operation of the endoscope 301A having the above-described configuration will be described.

In the endoscope 301A, when an operator bends the bending portion 302b, for example, upward, the operator rotates the operation dial 351 in the arrow 44Y1 direction in FIG. 44. Then, the shaft body 353 rotates integrally with the operation dial 351, whereby the fixing plate 354 and the sprocket 355 rotate about the shaft body fixing portion 354a.

The chain 357 engages with the sprocket 355. Then, the sliding members 356a and 356b are fixed to the chain 357. Accordingly, upon the sprocket 355 rotating about the shaft body fixing portion 354a, the first sliding member 356a moves toward the first ultrasound motor 352U. At this time, the second sliding member 356b moves away from the second ultrasound motor 352D. In other words, a space between the first sliding member 356a and the vibrating surface 352a of the first ultrasound motor 352U gradually decreases from a dimension d and a space between the second sliding member 356a and the vibrating surface 352a of the second ultrasound motor 352D increases relative to the dimension d.

Then, as a result of the first sliding member 356a abutting against the vibrating surface 352a, a straight advance drive force from the vibrating surface 352a is transmitted to the first sliding member 356a. The first sliding member 356a moves in the arrow 44Y2 direction according to a magnitude of a pressing force of the first sliding member 356a being pressed against the vibrating surface 352a. With the movement of the first sliding member 356a, the up bending wire 311 is pulled, whereby the bending portion 302bA starts bending upward.

Then, when an amount of rotation of the rotation operation dial 351 reaches a maximum angle set in advance, the up bending wire 311 is pulled maximally by the straight advance drive force transmitted from the vibrating surface 352a. At this time, the bending portion 302bA bends upward at a maximum bending angle.

In the present embodiment, as a result of the operation dial 351 being rotated, the space between the first sliding member 356a and the vibrating surface 352a and the space between the second sliding member 356a and the vibrating surface 352a are changed. In other words, upon the operation dial 351 being rotated, positions where the sliding members 356a and 356b run are changed.

An amount of operation strength for rotating the operation dial 351 gradually increases with an increase in rotation operation amount after the first sliding member 356a is brought into contact with the vibrating surface 352a of the first ultrasound motor 352U and also after the second sliding member 356b is brought into contact with the vibrating surface 352a of the first ultrasound motor 352D. Also, as the amount of operation strength for rotating the operation dial 351 increases, the pressing force of pressing the first sliding member 356a against the vibrating surface 352a and a pressing force of pressing the second sliding member 356b against the vibrating surface 352a increase.

Then, in the present embodiment, a maximum amount of operation strength for rotating the operation dial 351 is set in advance to be smaller than a predetermined value, that is, an amount of strength for directly pulling the bending wire 311 or 312 by operating the operation dial 351.

Note that the amount of operation strength for rotation can be set to a desired value by arbitrarily setting, e.g., a diameter dimension of the operation dial 351, a diameter dimension of the fixing plate 354, a diameter dimension of the sprocket 355 and a position of the shaft body fixing portion 354a.

Here, a bending operation of the bending portion 302bA of the endoscope 301A configured as described above will be described.

When an operator inserts the insertion portion 302 to a body from, for example, an oral cavity, the operator drives the pair of ultrasound motors 352U and 352D to vibrate the vibrating surfaces 352a. Then, the operator starts insertion of the insertion portion 302 into the body while observing an endoscopic image displayed on a screen of a non-illustrated observation apparatus.

Next, in order to, for example, bend the bending portion 302b upward, the operator rotates the operation dial 351 as described above to bring the first sliding member 356a into contact with the vibrating surface 352a of the first ultrasound motor 352U. Then, the first sliding member 356a is moved by the straight advance drive force of the vibrating surface 352a, whereby the up bending wire 311 is pulled in the arrow 44Y2 direction. As a result, the bending portion 302b bends upward. Note that the up bending wire 311 moves in proportion to the pressing force of the first sliding member 356a pressed against the vibrating surface 352a.

Here, if the operator further rotates the operation dial 351, the pressing force increases. Then, as described above, the first sliding member 356a is further moved by the straight advance drive force of the vibrating surface 352a. As a result, the up bending wire 311 is further pulled, whereby a bending angle of the bending portion 302b increases. On the other hand, if the operator holds a rotational position of the operation dial 351, the bending portion 302b is held in a state of bending at a bending angle corresponding to the rotational position of the operation dial 351.

Also, during continuation of the rotation of the operation dial 351 in the arrow Y44Y1 direction, if the distal end portion 302a abuts against a wall of a lumen, the bending operation of the bending portion 302b is interrupted by the wall. Here, for example, it may become impossible to pull the up bending wire 311. In the endoscope 301A according to the present embodiment, during a rotation operation to increase the bending angle of the bending portion 302bA, an amount of rotation operation strength put on the operation dial 351 increases as the bending angle becomes larger.

Accordingly, during the operator operating the operation dial, if an endoscopic image displayed on a screen of a display apparatus does not change despite an increase in amount of rotation operation strength to operate the operation dial 351, the operator can see trouble in the bending portion such as the distal end portion 2a of the insertion portion 302 abutting against a wall of a lumen.

As described above, with the endoscope 301A according to the present embodiment, the operation dial 351 provided at the operation portion 303 is rotated, whereby one of the sliding members 356a and 356b is made to abut against the vibrating surface 352a of the ultrasound motor 352U or 352D without directly pulling the bending wire 311 or 312. Then, the one of the sliding members 356a and 356b is pressed against the vibrating surface 352a, whereby the one of the sliding member 356a and 356b is moved by a straight advance drive force of the vibrating surface 352a. Then, the bending wire 311 or 312 corresponding to the moved sliding member 356a or 356b is pulled, whereby the bending portion 302b bends.

In this configuration, an amount of rotation operation strength on the operation dial 351 is set in advance to be smaller than an amount of strength for directly pulling the bending wire 311 or 312 by operating the operation dial 351. Thus, a bending operation of the bending portion 302b can easily be performed by rotating the operation dial 351 provided at the operation portion 303.

Also, a configuration in which an amount of rotation operation strength on the operation dial 351 is set in advance to be smaller than an amount of strength for directly pulling the bending wire 311 or 312 by operating the operation dial 351 and as a rotation operation to increase a bending angle of the bending portion 302bA is performed, the rotation operation strength amount and the pressing force amount increase is provided. As a result, during a rotation operation to bend the bending portion 302bA, an operator senses a change in stress on the relevant bending wire 311 or 312 from an endoscopic image displayed on the display apparatus and a change in amount of rotation operation strength, enabling prevention of a trouble due to an abnormality in the bending of the bending portion 302b.

Note that the bending portion 302bA bent by rotating the operation dial 351 restores to a straightened state by an elastic repellent force the bending portion 302bA has, by reversely rotating the operation dial 351 to return to an original position.

Also, where the bending portion bends in four directions, i.e., upward, downward, leftward and rightward, the operation dial 351, the ultrasound motor 352 and the drive force transmission section 310A described above are used for leftward/rightward bending, and another set is provided in the operation portion 303.

In the above description, the sliding member 356a or 356b is pressed against the vibrating surface 352a of the ultrasound motor 352U or 352D by rotating the operation dial 351 without directly pulling the bending wire 311 or 312. Then, the bending wire 311 or 312 is moved by a straight advance drive force of the relevant vibrating surface 352a to the sliding member 356a or 356b and thereby starts being pulled. However, the pulling member moving surfaces are not limited to the vibrating surfaces 352a of the ultrasound motors 352U and 352D and may be rotating bodies illustrated in FIG. 45. The rotating bodies are outer peripheral faces of rollers 364U and 64D that each rotate in a predetermined direction.

Figure 45:
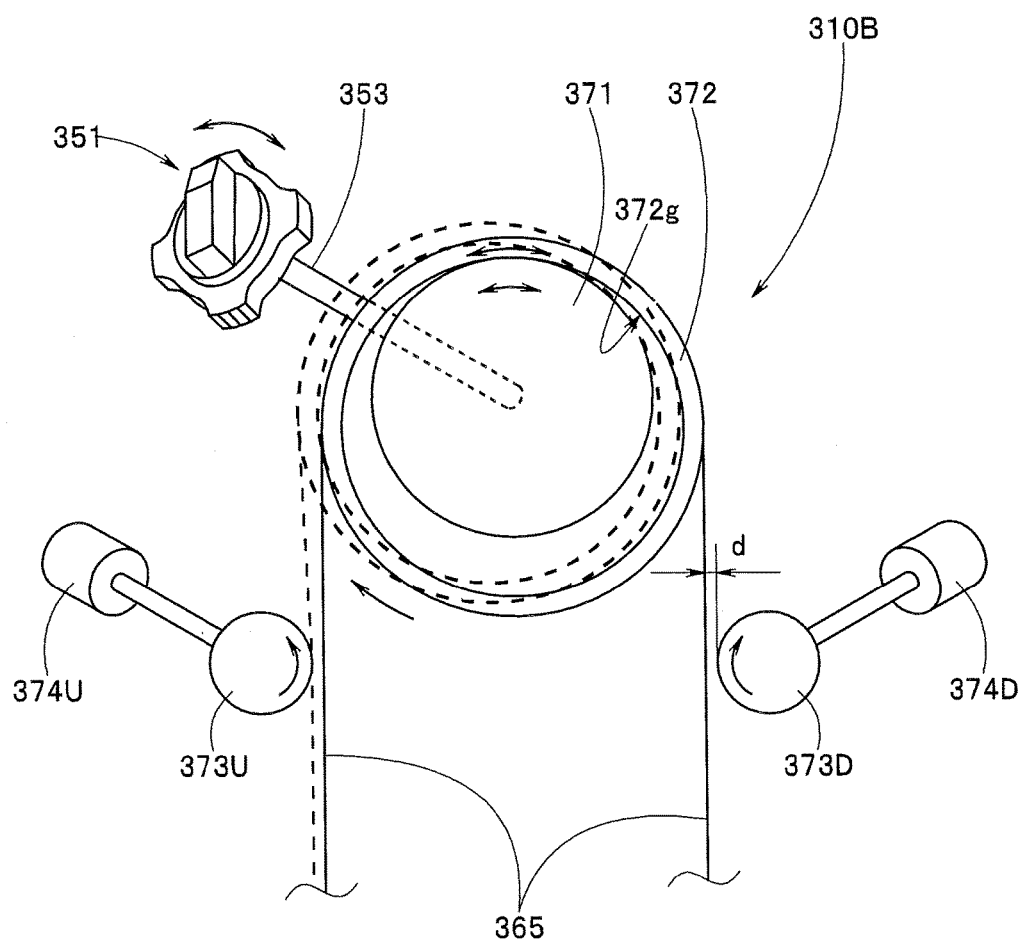
FIG. 45 is a diagram illustrating another example configuration of a drive force transmission section.

Reference numeral 361 illustrated in FIG. 45 denotes a first spur wheel, reference numeral 362 denotes a second spur wheel, reference numeral 363 denotes a drive motor and reference numeral 363a denotes a motor shaft.

The motor shaft 363a is fixed to the first spur wheel 361. In other words, the first spur wheel 361 is a drive gear wheel. The first spur wheel 361 and the second spur wheel 362 engage with each other. Accordingly, the second spur wheel 362 is a driven gear wheel that upon rotation of the first spur wheel 361 being transmitted thereto, rotates in a direction opposite to the first spur wheel 361.

The down roller 364D is coaxially fixed integrally to the first spur wheel 361. The up roller 364U is coaxially fixed integrally to the second spur wheel 362. As a result, upon the drive motor 363 being driven, the down roller 364D rotates clockwise and the up roller 364U rotates counterclockwise in the Figure.

In the present embodiment, a pulley 355P is pivotally attached to a fixing plate 354 instead of the sprocket 355. A bending wire 365 is wound around an outer peripheral face of the pulley 355P. One end of the bending wire 365 is fixed at a predetermined position on the distal end side of the bending portion 302bA. The other end of the bending wire 365 is fixed at a predetermined position on the distal end side of the bending portion 302bA. The bending wire 365 is tightened with a predetermined tensile force when the bending portion 302bA is in a straightened state. Then, a predetermined space d is formed between the up roller 364U and the bending wire 365 and also between the down roller 364D and the bending wire 365.

In other words, in the present embodiment, a drive section includes the rotating rollers 364U and 364D. Then, a drive force transmission section 310A1 includes a shaft body 353, a fixing plate 354, a pulley 355P and a bending wire 365.

With this configuration, with rotation of the operation dial 351, a position where the bending wire 365 runs is changed. Then, upon an operator rotating the operation dial 351 in the arrow 45Y1 direction, as indicated by dashed lines, the pulley 355P is moved toward the up roller 364U to press the bending wire 365 against an outer peripheral face of the up roller 364U. Then, a rotation drive force of the up roller 364U is transmitted to the bending wire 365, whereby the bending wire 365 is pulled in the arrow 45Y2 direction indicated by a dashed line, whereby the bending portion 302bA bends upward.

As described above, the operation dial 351 is rotated to make a positional change to press a part on one side of the bending wire 365 wound around the pulley 355P against the roller 364U and move a part on the other side of the bending wire 365 away from the roller 364D without directly pulling the bending wire 365. As a result, the part on the one side of the bending wire 365 pressed against the roller 364U is moved by the rotation drive force of the roller 364U, enabling provision of operations and effects similar to those of the above-described embodiment.

Note that in FIG. 46, a drive force transmission section 310B includes a shaft body 353, an external gear wheel 371 including a teeth portion at an outer peripheral of a round plate, an internal gear wheel-equipped pulley 372 having a ring shape and including a teeth portion engaging with the teeth portion, at an inner peripheral face thereof, and a bending wire 365.

In this configuration, rollers 373U and 373D are rotated in respective predetermined directions by respective drive motors 374U and 374D.

As with the above, the bending wire 365 is wound around an outer peripheral face of the internal gear wheel-equipped pulley 372. The shaft body 353 is fixed integrally to a center portion of the external gear wheel 371. An outer diameter dimension of the external gear wheel 371 is smaller than an internal diameter of a gear wheel 372g of the internal gear wheel-equipped pulley 372. Where the bending wire 365 is tightened with a predetermined tensile force, respective one parts of the external gear wheel 371 and the gear wheel 372g of the internal gear wheel-equipped pulley 372 engage with each other and respective the other remaining parts come off from each other, that is, engagement with play is provided.

With this configuration, upon the operation dial 351 being rotated, the shaft body 353 rotates integrally with the operation dial 351. As a result of the rotation of the shaft body 353, the external gear wheel 371 rotates, the internal gear wheel-equipped pulley 372 swings by the amount of the play as indicated by dashed lines.

Then, the part on the one side of the bending wire 365 wound around the outer peripheral face of the internal gear wheel-equipped pulley 372 is pressed against the outer peripheral face of the up roller 373U as indicated by a dashed line. On the other hand, the part on the other side of the bending wire 365 moves away from the down roller 373D. In other words, a position where the bending wire 365 runs is changed.

As a result, the part on the one side of the bending wire 365 pressed against the roller 373U is moved by a rotation drive force of the roller 373U, enabling provision of operations and effects similar to those of the above-described embodiment.

Note that in this configuration, each drive section may be an ultrasound linear motor instead of a motor 374 and a roller 373. Also, each drive section may use a roller-shaped magnet instead of a roller 373. For the magnet, a MagTran (registered trademark) is favorable, and the bending wire to be moved is configured to enable contactless drive transmission.

Also, in the above-described embodiment, it is assumed that an insertion apparatus is an endoscope, which is a medical device. However, the medical devices are not limited to endoscopes, and may be, for example, overtubes including a bending portion through which an endoscope is inserted or treatment instruments including a bending portion.

The third and fourth embodiments of the present appendices described in detail above can provide a configuration as follows.

(14) An insertion apparatus comprising:
a bending portion provided on a distal end side of an insertion portion extending from an operation portion, the bending portion being bendable in a plurality of directions;
pulling members provided so as to correspond to the plurality of bending directions, each pulling member including an end fixed at a predetermined position on a distal end side of the bending portion, the end being moved toward a proximal end upon the pulling member being pulled, thereby bending the bending portion;
a bending operation apparatus provided at the operation portion, the bending operation apparatus being operated to bend the bending portion; a drive section including a pulling member moving surface that moves any of the pulling members; and
a drive force transmission section that is moved upon the bending operation apparatus being operated, presses the pulling member corresponding to the operation of the bending operation apparatus against the pulling member moving surface to transmit a drive force of the pulling member moving surface to the pulling member.

(15) The insertion apparatus according to appendix 14, wherein the drive force transmission section includes:
a suspension frame attached and fixed to a rod-like manipulator that is tilted to bend the bending portion, via a universal joint pivotally disposed in a frame provided inside the operation portion;
operation input transmission wires each including a distal end and a proximal end, each proximal end being attached to a wire attachment portion provided at an end portion of a respective one of a plurality of frames included in the suspension frame; and
a plurality of pressing plates each including a joining portion with a distal end of the respective operation input transmission wire fixed thereto, a shaft hole through which a shaft fixed to the frame provided in the operation portion is inserted to be arranged, and a contact surface arranged so as to face the pulling member moving surface of the drive section across a predetermined pulling member from among the plurality of the pulling members.

(16) The insertion apparatus according to appendix 15, wherein the drive section includes a rotating body including a pulling member moving surface that generates a drive force, the rotating body being rotated in a predetermined direction by a drive motor.

(17) The insertion apparatus according to appendix 14, wherein the drive force transmission section includes:
a shaft portion coaxially fixed to an operation dial that is rotated clockwise or counterclockwise to bend the bending portion, the shaft portion rotating integrally with the operation dial;
a rotating plate with the pulling members arranged on an outer peripheral face thereof; and
a fixing plate with the rotating plate pivotally attached thereto and another end of the shaft portion fixed integrally to a position that is different from a center of rotation of the rotating plate.

(18) The insertion apparatus according to appendix 14, wherein the drive force transmission section includes:
a shaft portion coaxially fixed to an operation dial that is rotated clockwise or counterclockwise to bend the bending portion, the shaft portion rotating integrally with the operation dial;

a ring-shaped, internal gear wheel-equipped pulley with an internal gear wheel provided integrally to a rotating plate with the pulling members arranged on an outer peripheral face thereof; and an external gear wheel including an external gear wheel that engages with the internal gear wheel, the external gear wheel having an external diameter that is smaller than an internal diameter of the internal gear wheel-equipped pulley, another end of the shaft portion being fixed integrally to a center of rotation of the external gear wheel.

(19) The insertion apparatus according to appendix 4 or 18, wherein the drive section includes a pulling member moving surface that generates a straight advance drive force, and is an ultrasound motor that generates ultrasound vibration travelling in a predetermined direction.

(20) The insertion apparatus according to appendix 17 or 18, wherein the drive section includes a pulling member moving surface that generates a rotation drive force, and is a rotating body to be rotated in a predetermined direction by a drive motor.

Note that the present invention is not limited only to the above-described embodiments and various modifications are possible without departing from the spirit of the invention.

What is claimed is:

1. An endoscope comprising:
   an elongated insertion portion configured to be inserted into a subject, wherein the elongated insertion portion comprises a bendable portion configured to be bent in a first bending direction;
   a manipulator configured to be manually moved in a first direction by a first operation of an operator;
   a sensor configured to perform detection of a movement of the manipulator caused to be moved in the first direction by the first operation of the operator and to output a first operation input instruction signal corresponding to the movement in the first direction detected;
   a controller configured to generate a first drive signal based on the first operation input instruction signal output by the sensor;
   a first motor configured to generate a first drive force based on the first drive signal generated by the controller;
   a first pulley configured to be rotated by the first drive force;
   a first bending wire attached to the bendable portion and to the first pulley, wherein the first bending wire is configured to be pulled by the first pulley that is rotated by the first drive force generated by the first motor, to bend the bendable portion in the first bending direction; and
   a haptic feedback section comprising:
      a first transmission wire comprising a first elastic member,
      wherein a first part of the first transmission wire is joined directly to the first bending wire at a point between the bendable portion and the first pulley,
      wherein a second part of the first transmission wire is joined directly to the manipulator,
      wherein the first transmission wire is arranged to transmit forces directly between the first bending wire and the manipulator,
      wherein the haptic feedback section is further configured so that:
         in a state in which the first bending wire is not pulled by the first drive force to bend the bendable portion, the first transmission wire is tightened with a first predetermined tensile force with the first elastic member being in a first predetermined expanded state, and
      wherein in a state in which the first bending wire is pulled by the first drive force to bend the bendable portion in the first bending direction and a first reactive force is applied to the bendable portion as the bendable portion abuts against an object that prevents the first bending wire from moving to further bend the bendable portion in the first direction, and the manipulator is further moved by the first operation of the operator to further expand the first elastic member, a first load for moving the manipulator is transmitted from the first elastic member to the manipulator via the second part of the first transmission wire to provide the operator with a first haptic sensation representative of the first reactive force.

2. The insertion apparatus according to claim 1,
   wherein the bendable portion of the elongated insertion portion is configured to be bent in a second bending direction,
   wherein the manipulator is configured to be moved in a second direction by a second operation of the operator,
   wherein the sensor is configured to perform detection of the movement of the manipulator caused to be moved in the second direction by the second operation of the operator and to output a second operation input instruction signal corresponding to the movement in the second direction detected,
   wherein the controller is configured to generate a second drive signal based on the second operation input instruction signal output by the sensor,
   wherein the insertion apparatus further comprises:
      a second motor configured to generate a second drive force based on the second drive signal generated by the controller;
      a second pulley configured to be rotated by the second drive force; and
      a second bending wire attached to the bendable portion and to the second pulley, wherein the second bending wire is configured to pulled by the second pulley that is rotated by the second drive force generated by the second motor, to bend the bendable portion in the second bending direction, and
   wherein the haptic section further comprises:
      a second transmission wire comprising a second elastic member,
      wherein a first part of the second transmission wire is joined to the second bending wire or to the second pulley,
      wherein a second part of the second transmission wire is joined to the manipulator,
      wherein in a state in which the second bending wire is not pulled by the second drive force to bend the bendable portion, the second transmission wire is tightened with a second predetermined tensile force with the second elastic member being in a second predetermined expanded state, and
      wherein in a state in which the second bending wire is pulled by the second drive force to bend the bendable portion in the second bending direction and a second reactive force is applied to the bendable portion as the bendable portion abuts the object, and the manipulator is further moved to by the second operation of the operator to thereby further expand the second elastic member, a second load for moving the manipulator is transmitted from the second elastic member to the manipulator via the second part of the second transmission wire to provide the operator with a second haptic sensation.

3. The insertion apparatus according to claim 1,
wherein the manipulator comprises a shaft configured to be tilted in the first direction by the first operation of the operator, and
wherein the sensor is configured to perform detection of an amount of tilting of the shaft as the movement of the manipulator caused to be moved in the first direction by the first operation of the operator.

4. The insertion apparatus according to claim 1,
wherein the manipulator comprises a knob configured to be rotated in the first direction by the first operation of the operator, and
wherein the sensor is configured to perform detection of an angle of rotation of the knob as the movement of the manipulator caused to be moved in the first direction by the first operation of the operator.

5. The insertion apparatus according to claim 1,
wherein the first motor is configured to:
generate a rotation torque to rotate the first pulley to bend the bendable portion in the first bending direction; and
passively make reverse rotation when a rotation torque generated at the pulley by the first reactive force becomes larger than the rotation torque generated by the first motor,
wherein the reverse rotation further expands the first elastic member whereby the first load for moving the manipulator is transmitted from the first elastic member to the manipulator via the second part of the first transmission wire to provide the operator with the first haptic sensation.

* * * * *